US010434292B2

(12) United States Patent
Joe et al.

(10) Patent No.: US 10,434,292 B2
(45) Date of Patent: Oct. 8, 2019

(54) METHOD AND DEVICES FOR FLOW OCCLUSION DURING DEVICE EXCHANGES

(71) Applicant: ACCESS CLOSURE, Inc., Santa Clara, CA (US)

(72) Inventors: Wesley Chung Joe, Fremont, CA (US); Ronald Hundertmark, San Mateo, CA (US); Ali Hassan, Mountain View, CA (US); Richard Domingo Yazbeck, Los Altos, CA (US)

(73) Assignee: ACCESS CLOSURE, Santa Clara, CA (US)

( * ) Notice: Subject to any disclaimer, the term of this patent is extended or adjusted under 35 U.S.C. 154(b) by 867 days.

(21) Appl. No.: 14/542,315

(22) Filed: Nov. 14, 2014

(65) Prior Publication Data

US 2015/0133892 A1 May 14, 2015
US 2018/0193611 A9 Jul. 12, 2018

Related U.S. Application Data

(63) Continuation-in-part of application No. 13/531,227, filed on Jun. 22, 2012, now abandoned.
(Continued)

(51) Int. Cl.
*A61F 2/02* (2006.01)
*A61M 25/10* (2013.01)
(Continued)

(52) U.S. Cl.
CPC ........ *A61M 25/1018* (2013.01); *A61M 25/09* (2013.01); *A61M 25/10185* (2013.11);
(Continued)

(58) Field of Classification Search
CPC ........ A61M 25/1018; A61M 25/10185; A61M 25/09; A61M 25/002; A61M 2025/09175;
(Continued)

(56) References Cited

U.S. PATENT DOCUMENTS 3,648,572 A * 3/1972 Fischer ..................... F02F 1/10
123/193.3
3,911,927 A 10/1975 Rich et al.
(Continued)

FOREIGN PATENT DOCUMENTS

WO 9826833 A1 6/1998
WO 2008048568 A2 4/2008
(Continued)

OTHER PUBLICATIONS

Abbott Vascular, LOC Guide Wire Extension, 2009, 3 pages.
(Continued)

*Primary Examiner* — Amy R Weisberg
(74) *Attorney, Agent, or Firm* — Nada J. Ardeleanu

(57) ABSTRACT

A method of reducing the risk of clinical sequelae to catheter induced vascular injuries may include introducing a guide wire into a vascular sheath residing in a blood vessel, proximally retracting the vascular sheath while leaving the wire in place, and observing indicia of the presence or absence of a vascular injury caused to the blood vessel by the vascular sheath or a procedural catheter previously advanced through the vascular sheath. If indicia of a vascular injury are observed, the method may further involve proximally retracting the guide wire to position the inflatable balloon adjacent the injury and inflating the balloon to reduce blood flow past the injury, while leaving the guide wire in place to provide subsequent access to the injury. The inflatable balloon can be inflated and deflated through a valve positioned at the proximal end of the guide wire.

30 Claims, 47 Drawing Sheets

Related U.S. Application Data

(60) Provisional application No. 61/540,994, filed on Sep. 29, 2011, provisional application No. 61/501,125, filed on Jun. 24, 2011.

(51) Int. Cl.
*A61M 25/09* (2006.01)
*A61M 25/00* (2006.01)

(52) U.S. Cl.
CPC . *A61M 25/002* (2013.01); *A61M 2025/09008* (2013.01); *A61M 2025/09083* (2013.01); *A61M 2025/09125* (2013.01); *A61M 2025/09175* (2013.01)

(58) Field of Classification Search
CPC ......... A61M 2025/09125; A61M 2025/09008; A61M 2025/09083
USPC .................................. 606/159; 604/536–537
See application file for complete search history.

(56) References Cited

U.S. PATENT DOCUMENTS

| | | | |
|---|---|---|---|
| 3,982,544 A | 9/1976 | Dyck | |
| 4,116,201 A * | 9/1978 | Shah | A61M 25/1018 128/207.15 |
| 4,143,853 A * | 3/1979 | Abramson | A61M 39/26 137/515.7 |
| 4,205,683 A | 6/1980 | O'Neill | |
| 4,333,452 A | 6/1982 | Au | |
| 4,469,017 A * | 9/1984 | Hanlon | F16J 15/008 277/558 |
| 4,809,710 A * | 3/1989 | Williamson | A61B 5/036 600/561 |
| 4,846,174 A | 7/1989 | Willard et al. | |
| 4,886,067 A | 12/1989 | Palermo | |
| 4,998,923 A | 3/1991 | Samson et al. | |
| 5,045,061 A | 9/1991 | Seifert et al. | |
| 5,125,895 A | 6/1992 | Buchbinder et al. | |
| 5,133,364 A | 7/1992 | Palermo et al. | |
| 5,152,777 A * | 10/1992 | Goldberg | A61F 2/01 606/200 |
| 5,167,239 A | 12/1992 | Cohen et al. | |
| 5,169,386 A * | 12/1992 | Becker | A61F 2/04 600/435 |
| 5,207,229 A * | 5/1993 | Winters | A61M 25/0075 600/434 |
| 5,209,727 A | 5/1993 | Radisch, Jr. et al. | |
| 5,226,879 A * | 7/1993 | Ensminger | A61M 39/0208 604/256 |
| 5,234,003 A * | 8/1993 | Hall | A61M 25/09 600/434 |
| 5,263,931 A * | 11/1993 | Miller | A61B 1/00082 604/103.1 |
| 5,338,301 A | 8/1994 | Diaz | |
| 5,339,833 A | 8/1994 | Berthiaume et al. | |
| 5,370,685 A | 12/1994 | Stevens | |
| 5,484,409 A | 1/1996 | Atkinson et al. | |
| 5,520,645 A | 5/1996 | Imran et al. | |
| 5,527,292 A | 6/1996 | Adams et al. | |
| 5,536,252 A | 7/1996 | Imran et al. | |
| 5,549,554 A | 8/1996 | Miraki | |
| 5,609,627 A | 3/1997 | Goicoechea et al. | |
| 5,623,957 A * | 4/1997 | Lekholm | A61M 5/14216 137/246 |
| 5,779,668 A | 7/1998 | Grabenkort | |
| 5,779,688 A | 7/1998 | Imran et al. | |
| 5,807,318 A * | 9/1998 | St. Goar | A61M 1/3659 604/508 |
| 5,843,046 A * | 12/1998 | Motisi | A61M 39/0606 604/256 |
| 5,916,196 A | 6/1999 | Andrea et al. | |
| 6,050,972 A | 4/2000 | Zadno-Azizi et al. | |
| 6,090,083 A | 7/2000 | Sell et al. | |
| 6,176,844 B1 | 1/2001 | Lee | |
| 6,193,706 B1 | 2/2001 | Thorud et al. | |
| 6,235,050 B1 | 5/2001 | Quiachon et al. | |
| 6,283,950 B1 * | 9/2001 | Appling | A61M 25/0075 600/585 |
| 6,302,898 B1 | 10/2001 | Edwards et al. | |
| 6,322,577 B1 * | 11/2001 | McInnes | A61M 25/104 604/96.01 |
| 6,325,777 B1 | 12/2001 | Zadno-Azizi | |
| 6,451,043 B1 | 9/2002 | McInnes et al. | |
| 6,602,207 B1 | 8/2003 | Mam et al. | |
| 6,786,888 B1 | 9/2004 | Zadno-Azizi | |
| 6,923,822 B2 | 8/2005 | Crawford et al. | |
| 6,958,059 B2 * | 10/2005 | Zadno-Azizi | A61B 17/12109 604/103.01 |
| 7,063,714 B2 | 6/2006 | Dorros et al. | |
| 7,169,161 B2 | 1/2007 | Bonnette et al. | |
| 7,316,704 B2 | 1/2008 | Bagaoisan et al. | |
| 7,331,979 B2 | 2/2008 | Khosravi et al. | |
| 7,335,220 B2 | 2/2008 | Khosravi et al. | |
| 7,359,601 B2 * | 4/2008 | Loeb | A61B 18/22 385/116 |
| 7,713,227 B2 | 5/2010 | Wholey et al. | |
| 7,806,856 B2 | 10/2010 | Bagaoisan et al. | |
| 7,993,367 B2 | 8/2011 | Bagaoisan et al. | |
| 8,029,533 B2 | 10/2011 | Bagaoisan et al. | |
| 8,038,672 B2 * | 10/2011 | Malecki | A61B 17/0057 606/41 |
| 8,157,766 B2 * | 4/2012 | Bonnette | A61M 25/0133 600/585 |
| 8,394,069 B2 * | 3/2013 | Matusch | A61M 5/1782 604/222 |
| 8,394,122 B2 | 3/2013 | Bagaoisan et al. | |
| 8,491,648 B2 | 7/2013 | Hassan et al. | |
| 8,617,204 B2 | 12/2013 | Khosravi et al. | |
| 8,795,709 B2 | 8/2014 | Sawhney et al. | |
| 8,852,230 B2 | 10/2014 | Sawhney et al. | |
| 9,272,132 B2 * | 3/2016 | Laufer | A61B 18/12 |
| 9,532,785 B2 | 1/2017 | Hassan et al. | |
| 9,982,510 B2 * | 5/2018 | Vick, Jr. | E21B 33/1208 |
| 2002/0062131 A1 * | 5/2002 | Gallo, Sr. | A61B 18/1445 606/167 |
| 2002/0072730 A1 | 6/2002 | McGill et al. | |
| 2002/0091355 A1 | 7/2002 | Hayden | |
| 2002/0133124 A1 * | 9/2002 | Leinsing | A61M 39/26 604/256 |
| 2002/0173817 A1 * | 11/2002 | Kletschka | A61B 17/22032 606/194 |
| 2002/0198594 A1 | 12/2002 | Schreck | |
| 2003/0060802 A1 | 3/2003 | Omaleki et al. | |
| 2003/0098164 A1 * | 5/2003 | Hirth | E21B 43/10 166/382 |
| 2004/0010248 A1 * | 1/2004 | Appling | A61B 18/24 606/15 |
| 2004/0249342 A1 * | 12/2004 | Khosravi | A61B 17/00491 604/96.01 |
| 2005/0033346 A1 | 2/2005 | Sater | |
| 2005/0124939 A1 | 6/2005 | Konstantino | |
| 2005/0182437 A1 * | 8/2005 | Bonnette | A61M 25/09 606/194 |
| 2006/0217755 A1 * | 9/2006 | Eversull | A61B 17/3439 606/191 |
| 2006/0253072 A1 | 11/2006 | Pai et al. | |
| 2006/0258987 A1 * | 11/2006 | Lentz | A61M 25/0054 604/164.01 |
| 2007/0083187 A1 * | 4/2007 | Eversull | A61M 25/10 604/508 |
| 2007/0167876 A1 | 7/2007 | Euteneuer et al. | |
| 2007/0231366 A1 | 10/2007 | Sawhney et al. | |
| 2008/0082122 A1 | 4/2008 | Khosravi et al. | |
| 2008/0172118 A1 * | 7/2008 | Johnson | A61M 25/10 607/126 |
| 2009/0030409 A1 * | 1/2009 | Goldfarb | A61M 25/01 606/14 |
| 2009/0088793 A1 | 4/2009 | Bagaoisan et al. | |
| 2009/0254110 A1 | 10/2009 | Bagaoisan et al. | |

(56) References Cited

U.S. PATENT DOCUMENTS

| | | | |
|---|---|---|---|
| 2009/0318798 A1* | 12/2009 | Singh | A61B 1/012 600/424 |
| 2010/0159117 A1 | 6/2010 | Griffin et al. | |
| 2010/0168789 A1 | 7/2010 | Bagaoisan et al. | |
| 2010/0274085 A1* | 10/2010 | Mugan | A61B 17/22032 600/115 |
| 2010/0274280 A1 | 10/2010 | Sawhney et al. | |
| 2010/0280546 A1 | 11/2010 | Campbell et al. | |
| 2011/0009888 A1 | 1/2011 | Shturman | |
| 2011/0062275 A1* | 3/2011 | Westphal | B65H 54/543 242/486.2 |
| 2011/0118546 A1 | 5/2011 | Dillon et al. | |
| 2011/0118759 A1 | 5/2011 | Teichman et al. | |
| 2011/0290246 A1* | 12/2011 | Zachar | A61L 29/085 128/200.26 |
| 2011/0319922 A1* | 12/2011 | Kitagawa | A61M 25/09 606/192 |
| 2013/0046376 A1 | 2/2013 | Hassan et al. | |
| 2013/0060318 A1 | 3/2013 | Hassan et al. | |
| 2014/0100646 A1 | 4/2014 | Hassan et al. | |

FOREIGN PATENT DOCUMENTS

| | | |
|---|---|---|
| WO | 2009086512 A2 | 7/2009 |
| WO | 2012178073 A1 | 12/2012 |

OTHER PUBLICATIONS

Covidien, Steerable Guide Wires Precision With Every Turn, 2009, 6 pages.

Extended European Search Report for Application No. EP13845971.4, dated May 10, 2016, 8 pages.

Final Office Action in related U.S. Appl. No. 13/531,227, dated Jul. 29, 2013, 14 pages.

Final Office Action in related U.S. Appl. No. 13/531,227, dated Mar. 12, 2015, 37 pages.

Final Office Action dated Sep. 18, 2015 for U.S. Appl. No. 13/889,842, 10 pages.

International Preliminary Report on Patentability and Written Opinion for PCT/US2012/043832 dated Dec. 24, 2013, 9 pages.

International Search Report and Written Opinion for Application No. PCT/US2015/060516, dated Feb. 18, 2016, 13 pages.

International Search Report and Written Opinion for PCT/US2012/043832 dated Sep. 24, 2012, 10 pages.

International Search Report for Application No. PCT/US2013/063725, dated Jan. 3, 2014, 8 pages.

Non Final Office Action in related U.S. Appl. No. 13/531,227, dated Jul. 17, 2014, 29 pages.

Non-Final Office Action dated Aug. 27, 2015 for U.S. Appl. No. 13/531,227, 40 pages.

Notice of Allowance in U.S. Appl. No. 13/668,585 dated May 1, 2013, 12 pages.

Office Action in corresponding Chinese Patent Application No. 2013-80052855 dated Apr. 5, 2016, 25 pages.

Office Action in U.S. Appl. No. 13/668,585 dated Feb. 15, 2013, 5 pages.

Office Action dated May 1, 2013 for U.S. Appl. No. 13/531,227, 19 pages.

Scheinert D., et al., "Treatment of Catheter-Induced Iliac Artery Injuries With Self-Expanding Endografts," Journal of Endovascular Therapy, 2000; vol. 7 (3), pp. 213-220.

Supplemental European Search Report for European Application No. 12801817.3 dated Feb. 2, 2015, 6 pages.

Yamagami T., et al., "A Case of Iatrogenic Subclavian Artery Injury Successfully Treated with Endovascular Procedures," Annals of Vascular Diseases, 2011, vol. 4 (1), pp. 53-55.

\* cited by examiner

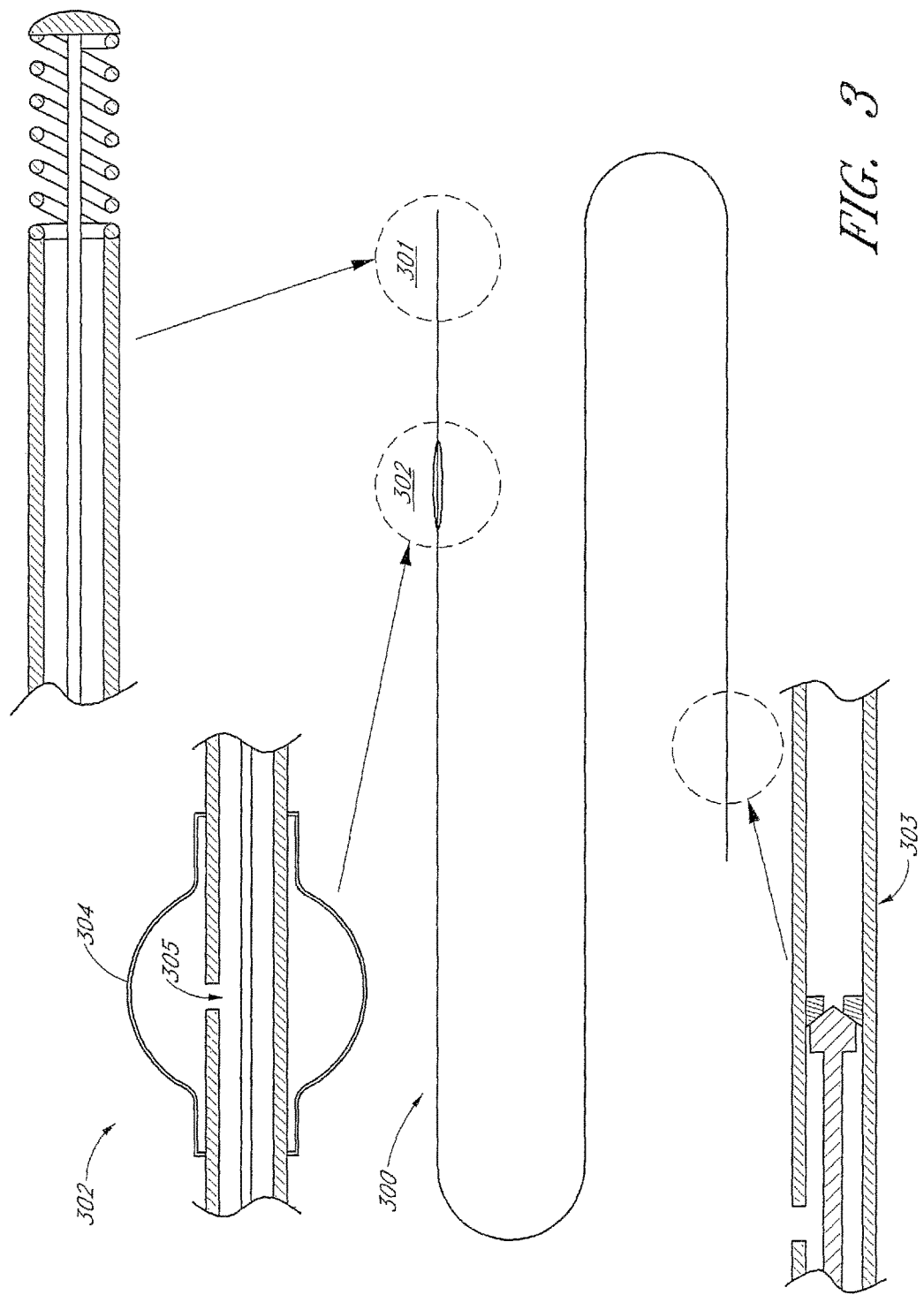

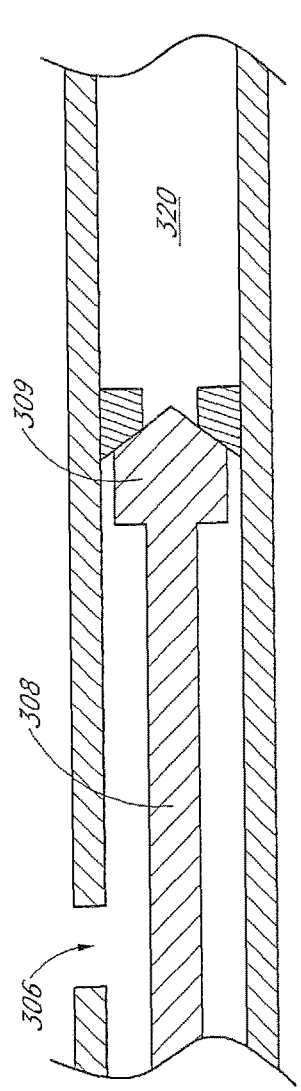
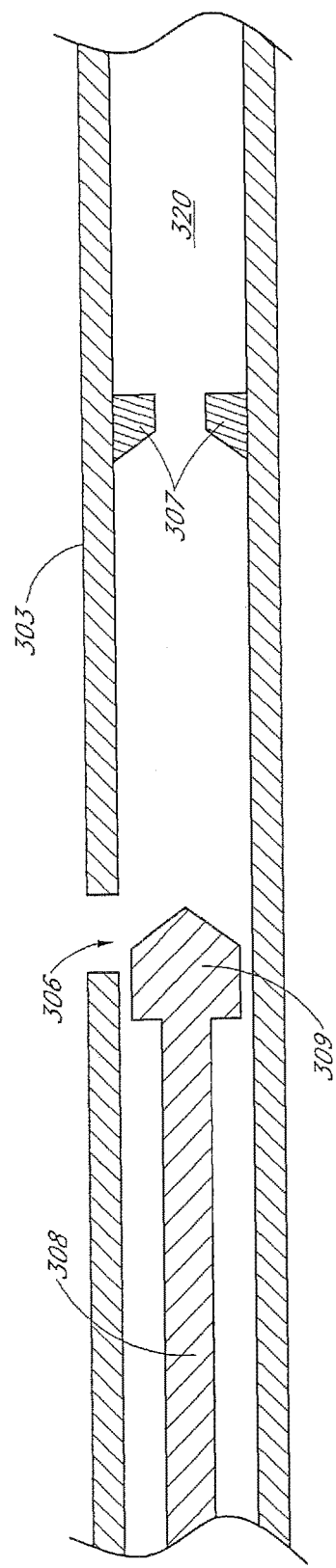

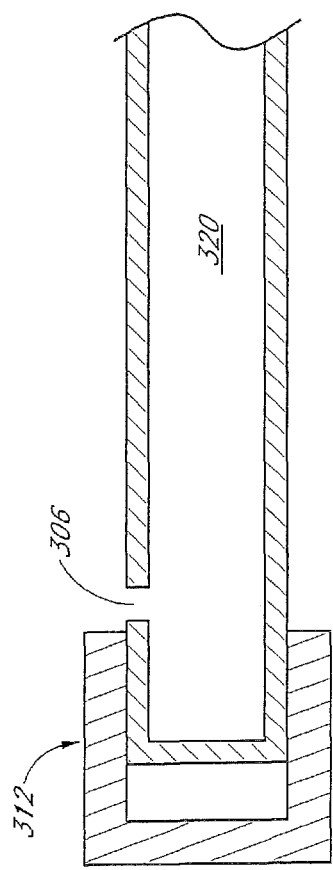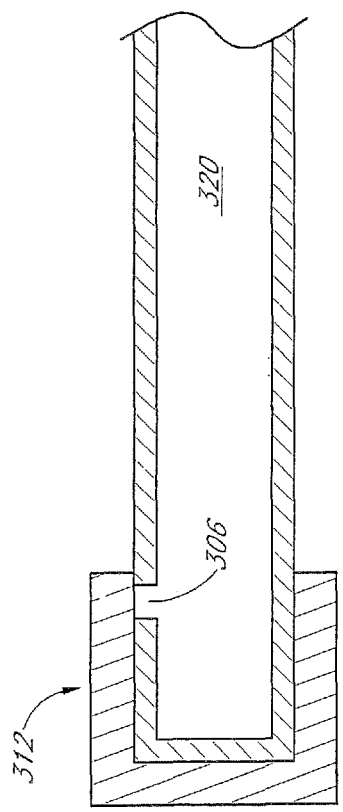

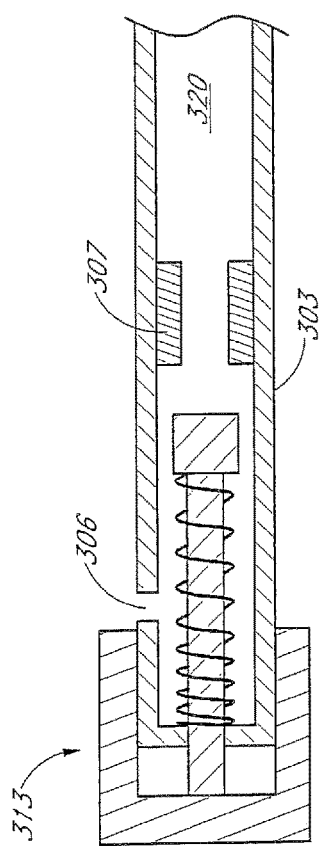
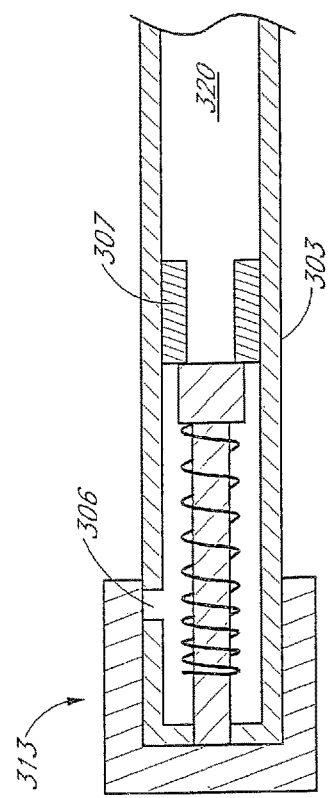
FIG. 7A
FIG. 7B

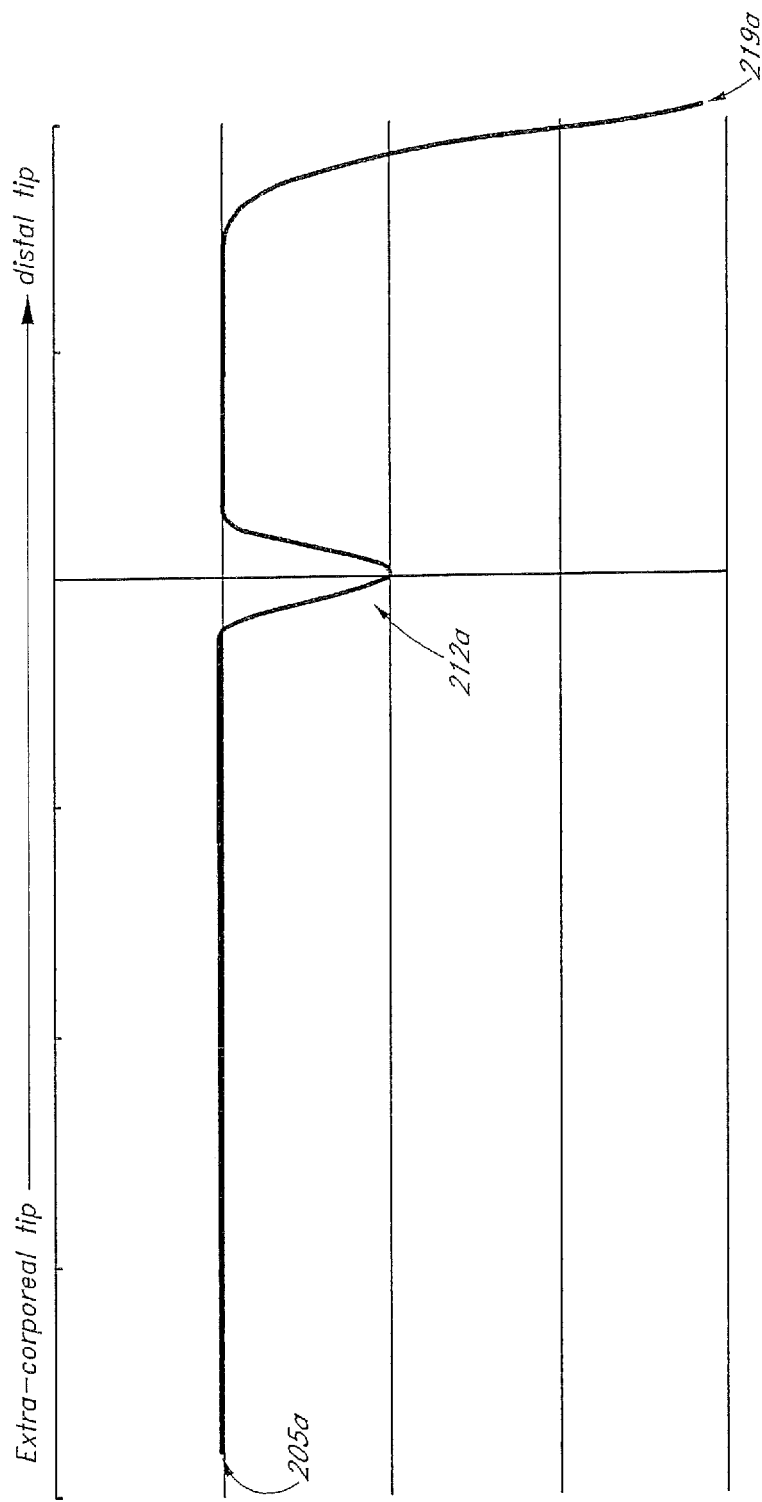

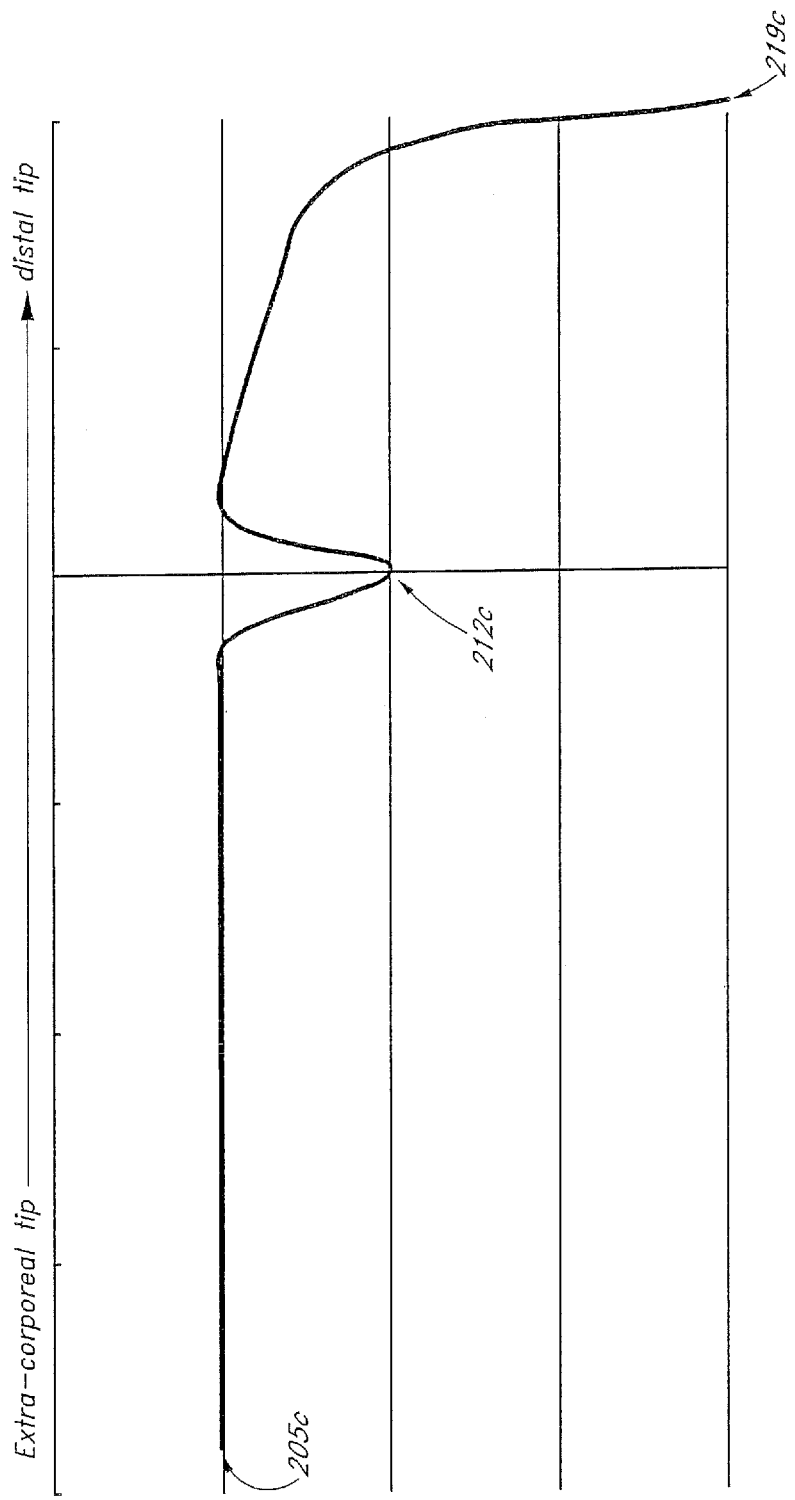

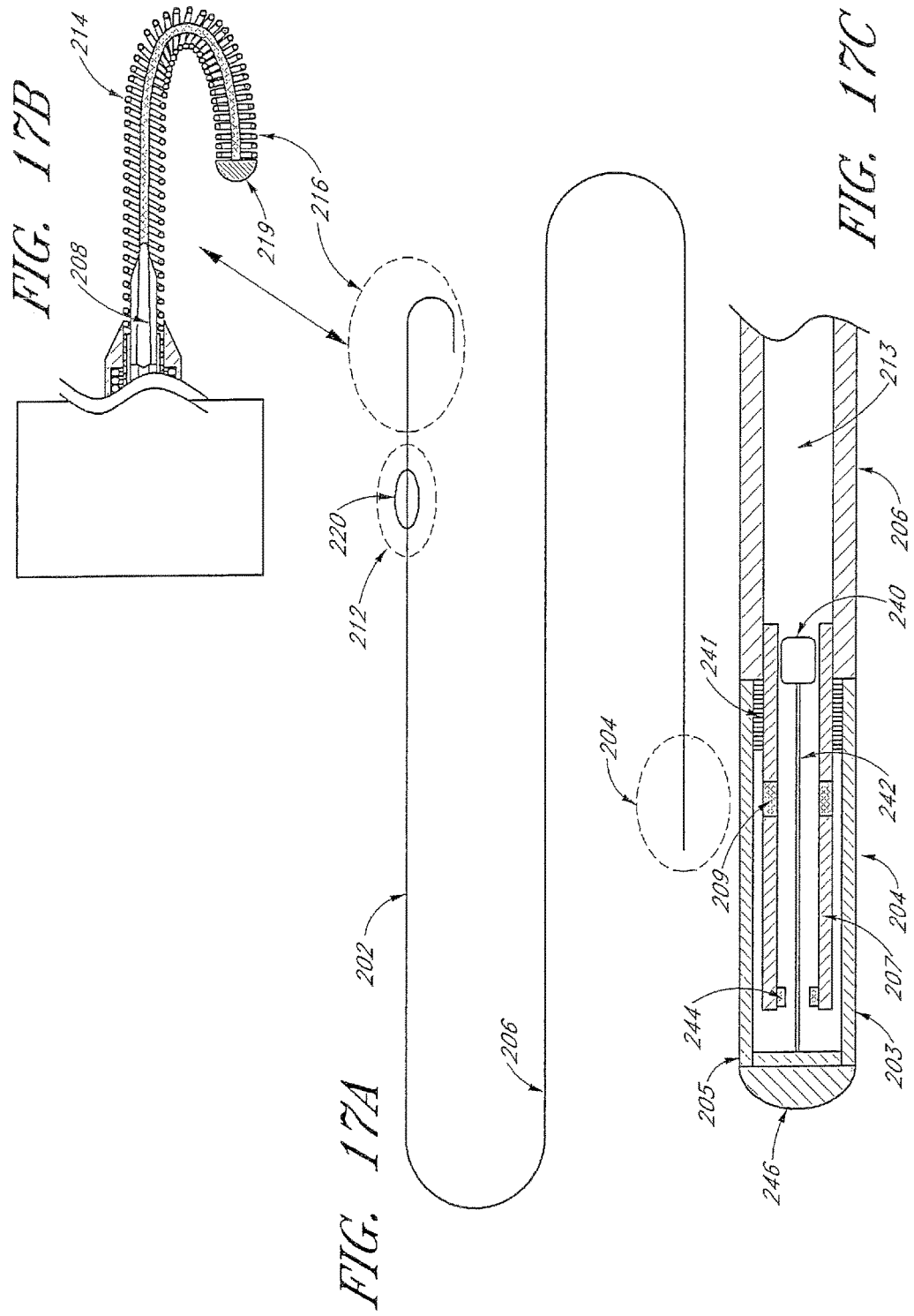

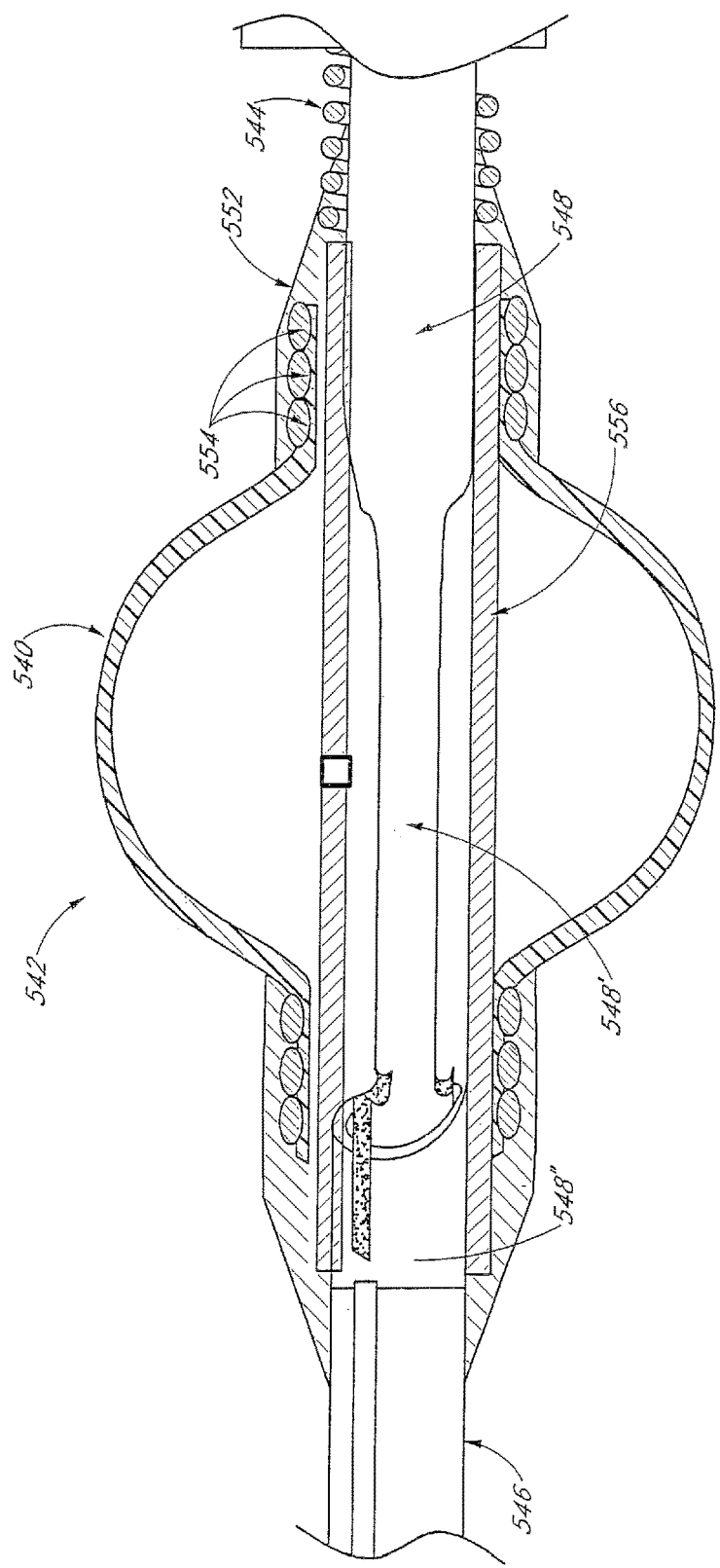

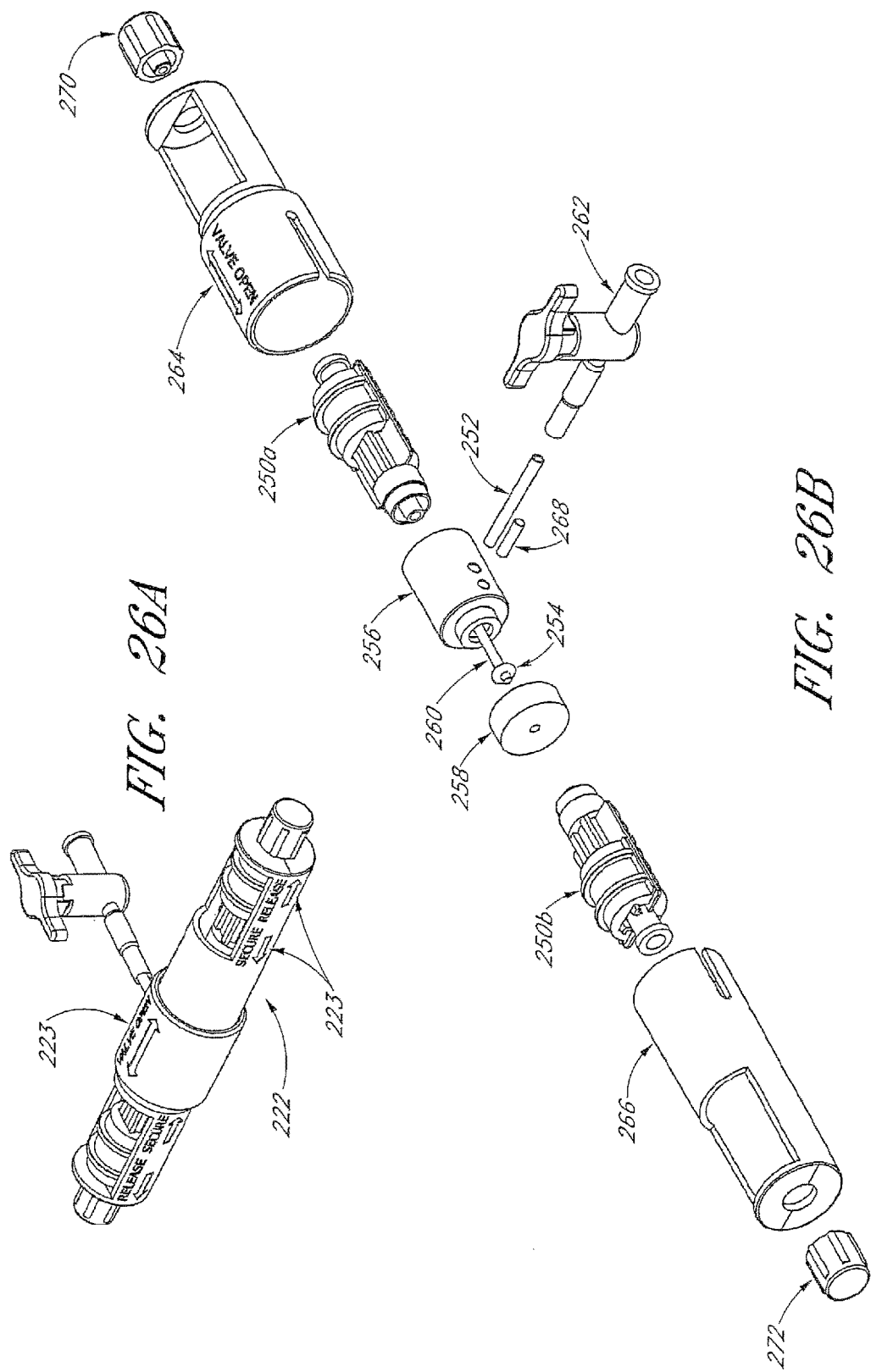

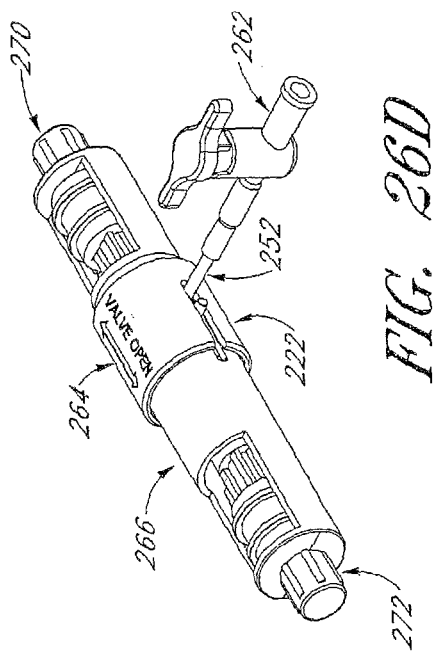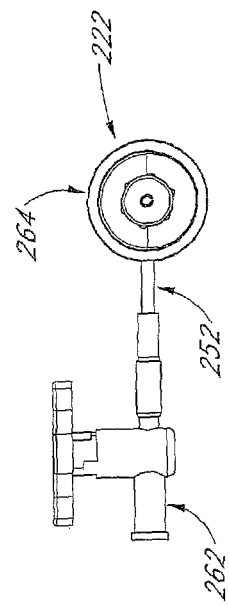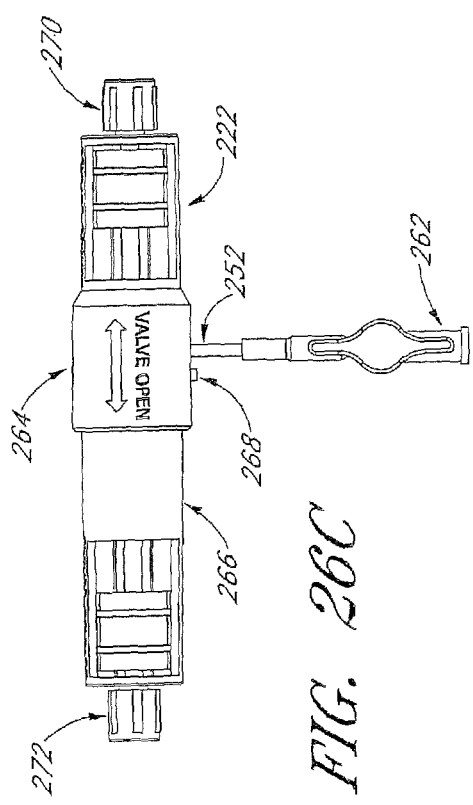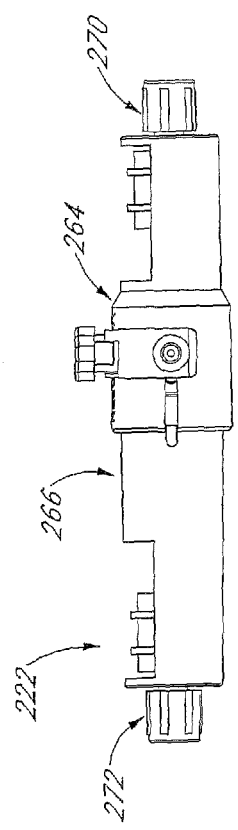
FIG. 26D
FIG. 26F
FIG. 26C
FIG. 26E

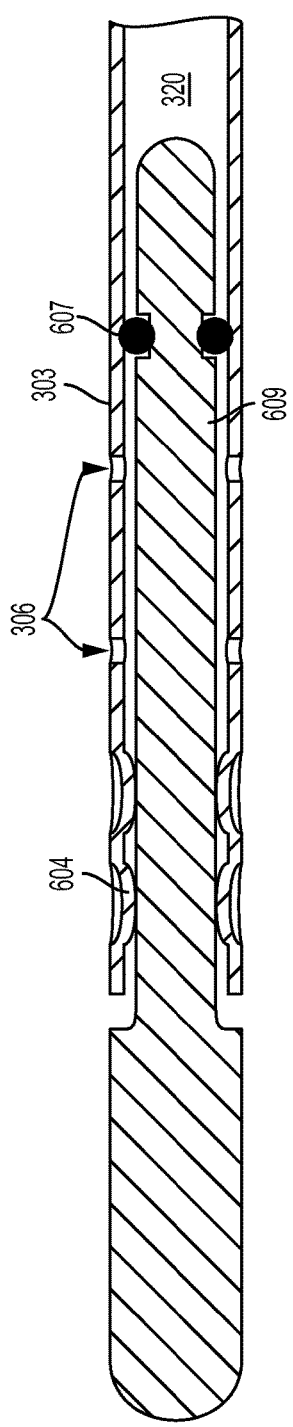
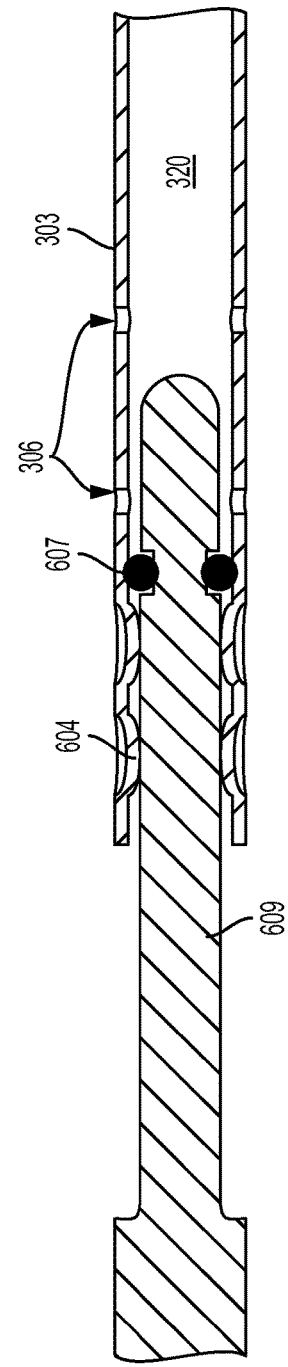
FIG. 32A
FIG. 32B

METHOD AND DEVICES FOR FLOW OCCLUSION DURING DEVICE EXCHANGES

CROSS-REFERENCE TO RELATED APPLICATIONS

This application is a continuation-in-part of U.S. patent application Ser. No. 13/531,227, entitled "Method And Devices For Flow Occlusion During Device Exchanges," filed on Jun. 22, 2012, which claims priority to U.S. Provisional Patent Application Ser. Nos. 61/501,125, entitled "Methods, Devices, and Systems for Flow Occlusion During Device Exchanges," filed on Jun. 24, 2011; and 61/540,994, entitled "Method and Devices for Flow Occlusion During Device Exchanges," filed on Sep. 29, 2011. This application is related to U.S. patent application Ser. No. 11/112,877, entitled "Apparatus and Methods for Sealing a Puncture in Tissue," filed on Apr. 22, 2005, and now issued as U.S. Pat. No. 8,002,742. The full disclosures of these references are hereby incorporated by reference.

FIELD

The field of the present application pertains to medical devices, and more particularly, to methods and systems for maintaining vascular access and/or minimizing bleeding, for example, during and after catheter-based interventions, for example, in the settings of device exchanges, vascular access closure, and the management of vascular complications.

BACKGROUND

Catheter-based medical procedures using large diameter (or "large bore") vascular access sheaths are becoming increasingly more common. Two examples of such large bore catheterization procedures that are gaining rapid popularity are Transcatheter Aortic Valve Implantation ("TAVI") and EndoVascular abdominal Aortic aneurysm Repair ("EVAR"). Although these procedures may often be effective at treating the condition addressed, they often cause injury to the blood vessel in which the large bore vascular access catheter is inserted to gain access for performing the procedure. In fact, vascular injury requiring treatment occurs in as many as 30-40% of large bore vascular procedures, according to some sources. Injury to the blood vessel may include perforation, rupture and/or dissection, which causes blood to flow out of the artery ("extravascular bleeding"), often requiring emergency surgery to repair the damaged blood vessel wall. If not properly treated, such a vascular injury may lead to anemia, hypotension or even death.

Vascular injury during large bore intravascular procedures is typically caused by the vascular access sheath itself and/or one or more instruments passed through the sheath to perform the procedure. Larger diameter vascular access sheaths are required in a number of catheter-based procedures, such as those mentioned above, where relatively large catheters/instruments must be passed through the sheath. Several other factors may increase the risk of vascular injury, including occlusive disease of the access vessel(s) and tortuosity/angulation of the access vessel(s). Another vascular injury caused by large bore intravascular procedures that can be challenging is the access site itself. Typically, large bore catheterizations create a significantly large arteriotomy, due to a disproportionately large ratio of the diameter of the vascular access catheter to the diameter of the artery in which it is placed. Large arteriotomies may require special management and multiple steps during closure. This may lead to significant blood loss while access closure is attempted.

Several techniques have been attempted to reduce the incidence of vascular injury in large bore vascular access procedures. For example, preoperative imaging of the blood vessel to be accessed, in the form of CT and MR angiography, may provide the physician with an idea of the anatomy of the vessel. If a particular vessel appears on imaging studies to be relatively tortuous or small, possible adjunctive maneuvers to prevent arterial dissection include pre-dilatation angioplasty of the iliofemoral vessels prior to large bore sheath placement, utilization of smaller access sheaths when possible, stiffer wires to aid in sheath placement and/or use of hydrophobic sheaths. In another attempt at preventing vessel injury, sheath placement may be performed under fluoroscopic guidance, and advancement may be halted when resistance is encountered. Despite the availability of these techniques, vascular injury requiring treatment still occurs in a large percentage of large bore vascular procedures.

Vascular injuries caused by intravascular procedures are generally quite difficult to diagnose and treat. When an arterial dissection occurs, it often remains undetected until the catheterization procedure is completed and the vascular access sheath is removed. For example, upon removal of the access sheath, large segments of the dissected vessel wall may be released within the vessel. The dissected vessel wall may lead to a breach in the artery wall, a flow-limiting stenosis, or distal embolization. Perforation or rupture of the iliofemoral artery segment may occur from persistent attempts to place large access sheaths in iliac arteries that are too small, too diseased, and/or too tortuous. Here too, a perforation may be likely to remain silent until sheath withdrawal.

Generally, vascular perforations and dissections caused by large bore vascular procedures allow very little time for the interventionalist to react. Frequently, these vascular injuries are associated with serious clinical sequelae, such as massive internal (retroperitoneal) bleeding, abrupt vessel closure, vital organ injuries, and emergency surgeries. In some cases, an interventionalist may first attempt to repair a vascular injury using an endovascular approach. First, the injury site may be controlled/stabilized with a balloon catheter, in an attempt to seal off the breached vessel wall and/or regain hemodynamic stability in the presence of appropriate resuscitation and transfusion of the patient by the anesthesiologist. Subsequently, endovascular treatment solutions may be attempted, for example if wire access is maintained through the true lumen. This may involve placement of one or more balloons, stents, or covered stents across the dissection/perforation. If the hemorrhage is controlled with these maneuvers and the patient is hemodynamically stabilized, significant reduction in morbidity and mortality may be realized. If attempts at endovascular repair of the vessel fail, emergency surgery is typically performed.

Presently, vascular injuries and complications occurring during and after large bore intravascular procedures are managed using a contralateral balloon occlusion technique ("CBOT"). CBOT involves accessing the contralateral femoral artery (the femoral artery opposite the one in which the large bore vascular access sheath is placed) with a separate access sheath, and then advancing and maneuvering a series of different guidewires, sheaths and catheters into the injured (ipsilateral) femoral or iliofemoral artery to treat the injury. Eventually, a (pre-sized) standard balloon catheter is advanced into the injured artery, and the balloon is inflated to reduce blood flow into the area of injury, thus stabilizing the injury until a repair procedure can be performed. Typically, CBOT involves at least the following steps: (1) Place a catheter within the contralateral iliofemoral artery (this catheter may already be in place for use in injecting contrast during the intravascular procedure); (2) Advance a thin, hydrophilic guidewire through the catheter and into the vascular access sheath located in the ipsilateral iliofemoral artery; (3) Remove the first catheter from the contralateral iliofemoral artery; (4) Advance a second, longer catheter over the guidewire and into the vascular access sheath; (5) Remove the thin, hydrophilic guidewire; (6) Advance a second, stiffer guidewire through the catheter into the vascular access sheath; (7) In some cases, an addition step at this point may involve increasing the size of the arteriotomy on the contralateral side to accommodate one or more balloon catheter and/or treatment devices for treating arterial trauma on the ipsilateral side; (8) Advance a balloon catheter over the stiffer guidewire into the damaged artery; (9) Inflate the balloon on the catheter to occlude the artery; (10) Advance one or more treatment devices, such as a stent delivery device, to the site of injury and repair the injury.

As this description suggests, the current CBOT technique requires many steps and exchanges of guidewire and catheters, most of which need to be carefully guided into a vascular access catheter in the opposite (ipsilateral) iliofemoral artery. Thus, the procedure is quite challenging and cumbersome. Although considered the standard of care in the management of vascular complications, the CBOT technique may not provide immediate stabilization of an injured segment, may lack ipsilateral device control, and/or may not provide ready access for additional therapeutics such as stents, other balloons and the like.

Therefore, in the management of vascular injuries and complications stemming from large bore intravascular procedures, it would be useful to provide a solution for minimizing blood loss and bridging the time to treatment (for example, an endovascular or surgical procedure) while maintaining an access pathway for delivering one or more treatment devices (balloon catheters, stents, etc.) to the injury site. It would also be desirable to provide blood flow occlusion during vascular closure after femoral artery catheterization. Ideally, a device for blood flow occlusion would be compatible with commonly available blood vessel closure devices and techniques, to facilitate blood flow occlusion during closure and occlusion device removal after closure. At least some of these objectives will be met by the embodiments described herein.

SUMMARY

Example embodiments described herein have several features, no single one of which is indispensable or solely responsible for their desirable attributes. Without limiting the scope of the claims, some of the advantageous features of some embodiments will now be summarized.

The present application is directed generally to medical devices, and more particularly, to methods and devices for maintaining vascular access and/or minimizing bleeding during percutaneous interventions.

For example, the methods and devices described herein may allow for simultaneous blood flow occlusion and device exchanges in the iliofemoral segment. In addition or alternatively, the methods and devices may maintain percutaneous vascular access while allowing for simultaneous flow occlusion and device exchanges. Optionally, the methods and devices may be utilized through the same (ipsilateral) interventional access site. The methods and devices may also be compatible with commonly available balloon/stent, and/or vascular closure systems.

In one aspect, a method of reducing the risk of clinical sequelae to catheter induced vascular injuries may involve: introducing a guide wire into a vascular sheath residing in a blood vessel, the guide wire having a distal end and an inflatable balloon at least 5 cm proximal of the distal end; proximally retracting the vascular sheath while leaving the wire in place; and observing indicia of the presence or absence of a vascular injury caused to the blood vessel by the vascular sheath or a procedural catheter previously advanced through the vascular sheath. If indicia of a vascular injury are observed, the method may further include proximally retracting the guide wire to position the inflatable balloon adjacent the injury and inflating the balloon to reduce blood flow past the injury, while leaving the guide wire in place to provide subsequent access to the injury.

In some embodiments, prior to the introducing step, the vascular sheath may be used for performing an intravascular procedure, such as but not limited to implantation of an aortic valve (TAVI/TAVR) and abdominal aortic aneurysm repair (EVAR). In some embodiments, observing indicia may involve observing contrast injected into the blood vessel using a radiographic imaging device. In some embodiments, the vascular sheath may have an external diameter at least about 80 percent as large as an internal diameter of the blood vessel. In some embodiments, the vascular sheath may be disposed in a femoral artery, the inflatable balloon may be at least 15 cm proximal of the distal end, and introducing the guide wire may involve advancing a tip of the wire into an aorta.

In some embodiments, inflating the balloon may involve inflating at a location of the vascular injury. Alternatively, inflating the balloon may involve inflating at a location upstream of the vascular injury. In some embodiments, the method may further include: removing the vascular sheath from the blood vessel; forming at least a partial seal at a puncture site in the blood vessel through which the vascular sheath was removed from the blood vessel; deflating the inflatable balloon of the guide wire; and removing the guide wire from the blood vessel through the seal at the puncture site, where the seal closes around a small hole left in the seal when the guide wire is removed. In some embodiment, the method may further involve introducing a vascular repair device over the guide wire and repairing the vascular injury using the vascular repair device. In some embodiments, the vascular repair device may include a stent deployment catheter, and repairing the vascular injury comprises placing a stent in the blood vessel.

In another aspect, a method of treating a patient may include: advancing a guide wire into a vascular sheath following an intravascular procedure, the guide wire comprising a distal end and a radially expandable structure spaced at least 5 cm proximally of the distal end; proximally withdrawing the sheath; evaluating the presence of a vascular injury caused by the sheath or a device introduced through the sheath; and if a vascular injury is observed, repositioning the guide wire and expanding the radially expandable structure to stabilize the injury. In some embodiments, the vascular sheath may be located in an iliofemoral artery, and advancing the guide wire may involve advancing the wire through into the vascular sheath from outside the body.

In one embodiment, the intravascular procedure includes implantation of an aortic valve. In another embodiment, the intravascular procedure includes an abdominal aortic aneurysm repair. In some embodiments, expanding the radially expandable structure may involve inflating a balloon. In some embodiments, expanding the radially expandable structure to stabilize the injury may involve reducing blood flow in an area around the vascular injury.

In another aspect, a method of treating a patient may involve introducing a guide wire into a blood vessel, the guide wire comprising a distal end and an inflatable balloon spaced at least 5 cm proximally of the balloon, introducing an index procedure catheter over the wire, and conducting an index procedure proximally of the balloon. In some embodiments, the index procedure may include implantation of an aortic valve. In some embodiments, the index procedure may include an abdominal aortic aneurysm repair.

In another aspect, a method of reducing the risk of clinical sequelae to catheter induced vascular injuries may include introducing a guide wire into a vessel, the guide wire having a distal end and a radially enlargeable structure at least 5 cm proximal of the distal end, advancing a procedure catheter along the wire, and performing a procedure with the procedure catheter, such that if the procedure catheter or an access sheath used introduce the procedure catheter produces a vascular injury, the guide wire can be advanced or retracted to position the radially enlargeable structure adjacent the injury, and the structure can be radially enlarged to control the injury while leaving the guide wire in place to provide subsequent access to the injury. In one embodiment, the procedure catheter may be an over the wire catheter. In one embodiment, the procedure catheter may be a rapid exchange catheter. In one embodiment, the procedure may be a heart valve repair. In one embodiment, the procedure may be a heart valve replacement. In one embodiment, the procedure may be implantation of an abdominal aortic aneurysm graft.

In some embodiments, if a vascular injury is not observed, the guide wire may be advanced or retracted without radially enlarging the radially enlargeable structure. In some embodiments, the radially enlargeable structure may be an inflatable balloon. Some embodiments may further include the step of evaluating the presence of a vascular perforation using Doppler ultrasound. Some embodiments may further include the step of evaluating the presence of a vascular perforation using contrast injection. In some embodiments, a vascular perforation is observed, the radially enlargeable structure is enlarged to control the injury, and a repair catheter is advanced along the guide wire. In some embodiments, the repair catheter may include a stent delivery catheter. In some embodiments, the repair catheter may include a graft delivery catheter. In some embodiments, a vascular injury is observed, the radially enlargeable structure is enlarged to control the injury, and the injury is thereafter surgically repaired.

In another aspect, a method of treating a catheter induced vascular injury may involve: advancing an inflatable balloon of a guide wire through a vascular sheath disposed in an iliofemoral artery, where the vascular sheath was used to perform a catheter based intravascular procedure; retracting the vascular sheath proximally; assessing the artery for injury; repositioning the guide wire within the artery; inflating the balloon to occlude the artery; removing an inflation device from the guide wire, wherein the balloon remains inflated after the inflation device is removed; advancing a vascular repair device over a proximal end of the guide wire; performing a repair procedure on the artery, using the repair device; removing the repair device over the guide wire; deflating the balloon using the inflation device; and removing the guide wire from the artery.

In some embodiments, prior to the advancing step, the vascular sheath is used for performing an intravascular procedure, such as but not limited to implantation of an aortic valve or abdominal aortic aneurysm repair. In some embodiments, observing indicia involves observing contrast injected into the artery using a radiographic imaging device. In some embodiments, the vascular sheath may be disposed in a femoral artery, the inflatable balloon may be at least 15 cm proximal of a distal end of the guide wire, and advancing the guide wire may involve advancing a tip of the wire into an aorta. In some embodiments, inflating the balloon may involve inflating at a location of the vascular injury. In some embodiments, inflating the balloon may involve inflating at a location upstream of the vascular injury.

In another aspect, a vascular guide wire may include: an elongate tubular body having a proximal end, a distal end and a lumen extending longitudinally through at least part of the body, which may include a proximal portion, a flexible distal tip that is at least about 15 cm long and is more flexible than the proximal portion, and a transition portion between the proximal and distal portions. The guide wire may further include an inflatable balloon disposed on the transition portion and in communication with the lumen and a valve on the proximal portion of the elongate body configured to couple with an inflation device to allow for inflation and deflation of the balloon.

In some embodiments, the valve may include an axially movable occluder, positioned within the lumen, and the valve may be configured to lock inflation fluid inside the lumen when in a closed position, to allow the inflation device to be removed, thus leaving a hubless proximal end over which one or more devices may be advanced. In some embodiments, the occluder may be movable between a proximal position and a distal position, and the valve may be closed when the occluder is in the distal position. In some embodiments, the distal tip may include a proximal section having a first flexibility and a J-tip at the distal end of the elongate body having a second flexibility that is greater than the first flexibility. In some embodiments, the proximal section may have a length of at least about 15 cm, and the J-tip may have a length of at least about 5 cm. In some embodiments, the distal tip may have a length of at least about 20 cm. In some embodiments, the distal tip may have a length approximately equal to an average length of an iliofemoral artery.

In some embodiments, the proximal portion may include a tube with a spiral cut along a portion of its length nearer its distal end, and the spiral cut may have decreasing spacing toward the distal end. In some embodiments, the distal tip may include a core wire wrapped in a coil, and the core wire may extend through the transition portion and into the proximal portion. Optionally, some embodiments may further include a coating over the spiral cut to prevent fluid from passing out of the lumen through the cut.

In another aspect, a vascular guide wire may include an elongate tubular body having a proximal end, a distal end, and a lumen extending longitudinally through at least part of the body. The elongate body may include a proximal section having a first average stiffness, a transition section having a second average stiffness that is less than the first stiffness, and a distal tip having a length of at least about 15 cm and a third average stiffness that is less than the second stiffness. The guide wire may further include an expandable member disposed on the transition section, wherein the expandable member is expandable via fluid advanced through the central lumen of the elongate body.

In some embodiments, the distal tip may have approximately the same stiffness as the transition section immediately adjacent a distal end of the transition section and may become significantly more flexible toward the distal end of the elongate body. In some embodiments, the guide wire may also include a valve within the tubular body. In some embodiments, the valve may include a locking feature for locking in an inflated configuration to maintain the expandable member in an expanded configuration even after an inflation device is removed from the wire. In some embodiments, the distal tip may include a preformed J-tip such that a curved sidewall of the J-tip rather than the distal end of the elongate body is the leading structure during normal transvascular advance.

Optionally, the guide wire may also include at least one radiopaque marker for indicating a position of the expandable member. In some embodiments, the expandable member may be an inflatable balloon. In some embodiments, the distal tip may have a length of at least about 20 cm. In some embodiments, the distal tip may have a length approximately equal to an average length of an iliofemoral artery. In some embodiments, the proximal end of the elongate body may be hubless, such that at least one additional device may be passed over the proximal end while the guide wire device is in the patient with the expandable member in an expanded configuration.

In another aspect, a vascular guide wire system may include a guide wire device and an inflation device. The guide wire device may include an elongate tubular body having a proximal portion, a flexible distal tip that is at least about 15 cm long and is more flexible than the proximal portion, a transition portion between the proximal and distal portions, and a lumen extending longitudinally through at least part of the body. The guide wire device may also include an inflatable balloon disposed on the transition portion and in communication with the lumen and a valve on the proximal portion of the elongate body. The inflation device may be configured to couple with the elongate body to open and close the valve and allow for inflation of the inflatable balloon.

In some embodiments, the valve may include an axially movable occluder, positioned within the lumen, and the valve may be configured to lock inflation fluid inside the lumen when in a closed position, to allow the inflation device to be removed, thus leaving a hubless proximal end of the elongate body, over which one or more devices may be advanced. Optionally, some embodiments of the system may further include an inflation medium injection device, such as but not limited to a pump. In some embodiment, the distal tip of the guide wire device may be a J-tip and may have a length of at least about 20 cm. In some embodiments, the proximal end of the elongate body may be hubless. In some embodiments, the distal tip of the guide wire device may include a core wire wrapped in a coil, and the core wire may extend through the transition portion and into the proximal portion.

In another embodiment, the valve provided to lock inflation fluid inside the lumen when in a closed position, can comprise a microvalve assembly. The microvalve assembly can be provided such that it allows the inflatable balloon to be inflated while the valve is in the open position, and upon closing the valve it locks the inflation fluid inside the lumen. The microvalve can be provided with a profile small enough such that the vascular guide wire or elongate body can continue to function as a guide wire. To deflate the balloon, the valve can be re-opened.

In yet another embodiment, the valve can comprise a micro O-ring that can be constrained on each end by a pair of small sleeves. A movable wire, or piston element, can be integrated with a frictional element and handle that when shifted into the lumen of the guide wire in a distal direction can act as a sealing mechanism. The O-ring can be stationary and the action of the piston shifting into the inner diameter of the O-ring sealing member can cause it to seal and provide a closed state. Shifting the handle of the piston in a proximal direction, partially withdrawing the piston from the lumen of the guide wire can open the valve by removing the piston from the O-ring inner diameter. Alternatively, the O-ring can be attached at the end of the piston and movable together with the piston to block the inflation port or fill ports.

These and other aspects and embodiments of the invention will be described below in further detail, in relation to the attached drawings.

BRIEF DESCRIPTION OF THE DRAWINGS

FIG. 3 is a side view of an exemplary guide wire balloon device, along with close-up, cross-sectional views of a distal tip, balloon section and valve section of the device, according to one embodiment;

FIGS. 4A and 4B are cross-sectional side views of an alternative embodiment of a valve section (fluid regulator/valve), shown in a valve-closed configuration (FIG. 4A) and a valve-open configuration (FIG. 4B), which may be included in a guide wire device, such as the guide wire device shown in FIG. 3;

FIGS. 6A and 6B are cross-sectional side views of an alternative embodiment of a valve section (fluid regulator/valve), shown in a valve-open configuration (FIG. 6A) and a valve-closed configuration (FIG. 6B), which may be included in a guide wire device, such as the guide wire device shown in FIG. 3;

FIGS. 7A and 7B are cross-sectional side views of an alternative embodiment of a valve section (fluid regulator/valve), shown in a valve-open configuration (FIG. 7A) and a valve-closed configuration (FIG. 7B), which may be included in a guide wire device, such as the guide wire device shown in FIG. 3;

FIGS. 9A-9L illustrate alternative stiffness characteristics of the individual segments of a guide wire device, according to various alternative embodiments;

FIG. 17A is a side view of a guide wire device such as that shown in FIG. 15;

FIG. 17B is a side, cross-sectional view of the distal tip of the guide wire device of FIG. 17A;

FIGS. 17C and 17D are side, cross-sectional views of the valve section of the guide wire device of FIG. 17A, shown in a valve-closed configuration (FIG. 17C) and a valve-open configuration (FIG. 17D);

FIGS. 18-25 are side, cross-sectional views of balloon sections of guide wire devices, according to various alternative embodiments;

FIG. 26A is a perspective view of an inflation device for use with a guide wire balloon device, according to one embodiment;

FIG. 26B is an exploded view of the inflation device of FIG. 26A;

FIGS. 26C-26F are top, perspective, side and end-on views, respectively, of the inflation device of FIG. 26A;

FIGS. 32A and 32B are cross-sectional side views of another alternative embodiment of a valve section (fluid regulator/valve), shown in a valve-closed configuration (FIG. 32A) and a valve-open configuration (FIG. 32B), which may be included in a guide wire device.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1A:
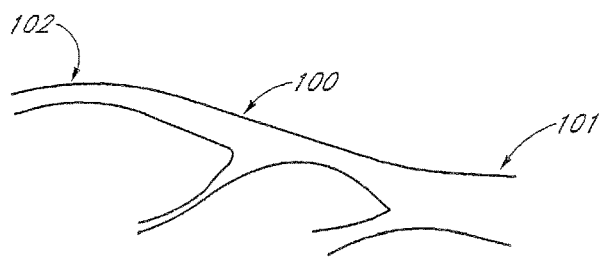
FIGS. 1A-1E are diagrammatic illustrations of a femoral artery, iliofemoral segment and aorta portion, showing an exemplary method for controlling blood flow during vascular access closure, according to one embodiment.

Referring now to FIGS. 1A-1E, one embodiment of a method for controlling bleeding during vascular closure, for example after femoral artery catheterization, is illustrated. FIG. 1A shows a segment of an arterial pathway, including the iliofemoral artery 100, the femoral artery 102, and the aorta 101. (This and other anatomical drawings are not drawn to scale and are not necessarily anatomically correct but are provided for descriptive, exemplary purposes.) Many of the descriptions herein discuss accessing and treating an iliofemoral artery (or "iliofemoral segement"), which is a length of an artery extending from a portion of a femoral artery to a portion of an iliac artery. These descriptions are for exemplary purposes only, and in various embodiments, other blood vessels may be accessed and/or treated, such as but not limited to femoral arteries, iliac arteries, aortas and the like. For example, using various devices and methods described below, a guide wire balloon catheter device may be advanced into a femoral artery, a distal tip of the device may be passed into the aorta, and the device may then be used to occlude flow within, and provide access to, an iliofemoral artery. Thus, the descriptions below should not be interpreted to limit the scope of the invention to a particular blood vessel.

Figure 1B:
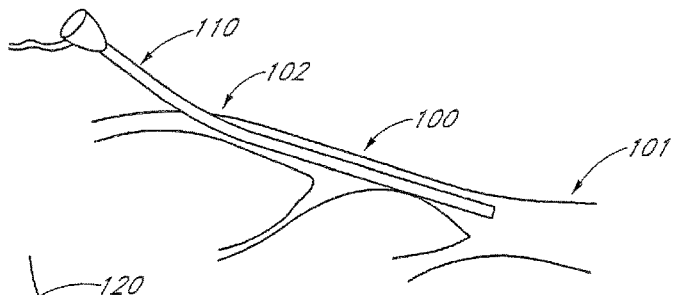

FIG. 1B shows a vascular access sheath 110 inserted through a vascular access site in the femoral artery 102 and extending through the iliofemoral segment 100 for conducting any suitable diagnostic and/or therapeutic catheterization procedure. The sheath 110 may have a diameter of 14F, 16F, 18F or the like in some embodiments, or may be smaller or larger in alternative embodiments. Generally, the sheath 110 may be any suitable sheath for performing an intravascular procedure and is placed in the iliofemoral artery 100 to perform the procedure (i.e., prior to the introduction and use of the guide wire device described herein.) The sheath 110 may be introduced in a retrograde orientation, as shown, or alternatively, in some procedures, the sheath 110 and/or other devices herein may be introduced antegrade relative to the patient's blood flow, as appropriate for a given application.

Figure 1C:
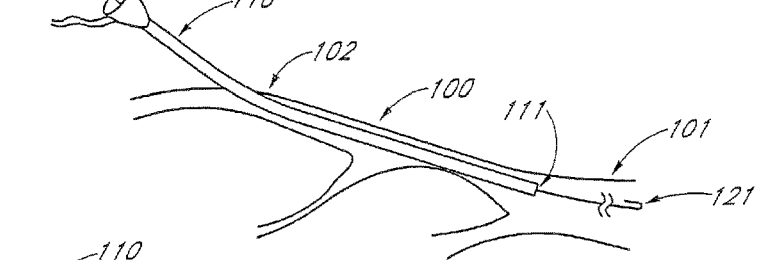

Referring now to FIG. 1C, upon completion of the catheter-based procedure, and before sheath withdrawal, a guide wire balloon device 120 or system (for example, any of the embodiments described elsewhere herein or in the applications incorporated by reference herein) may be inserted into the sheath 110 such that a tip 121 of the guide wire device 120, for example, a floppy "J tip," is positioned past the distal tip 111 of the sheath 110 inside the aorta 101. The guide wire balloon device 120 may be described herein as an "guide wire," "guide wire balloon catheter," "guide wire device" or the like. As described further elsewhere herein, the guide wire device 120 may have a cross-sectional size that allows the sheath 110 to be inserted, withdrawn and/or exchanged over the guide wire shaft (and/or allow secondary devices to be advanced over the device 120). Thus, the sheath 110 may be withdrawn (partially or completely) proximally and/or advanced distally over the guide wire device 120 to adjust positioning of the sheath 110 relative to the device 120.

Figure 1D:
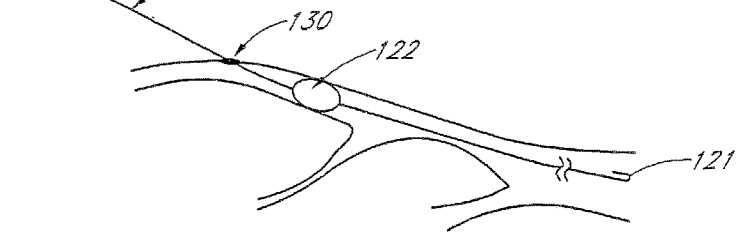

As illustrated in FIG. 1D, in a next step, the sheath 110 may be retracted/withdrawn relative to the guide wire device 120, while maintaining the device 120 in position, to expose a balloon 122 or other expandable member on the guide wire device 120. The balloon 122 may be positioned and inflated at a desired occlusion site before, during, or after complete withdrawal of the sheath, as shown in FIG. 1D.

With continuing reference to FIG. 1D, after the sheath 110 has been removed from the femoral artery, the vascular access site may be closed, for example, with a suture/sealant combination 130, advanced about or otherwise in cooperation with the guide wire device 120 at the site of arteriotomy. Exemplary closure devices and methods that may be delivered over or otherwise in conjunction with the guide wire device 120 (or any of the embodiments herein) are disclosed in U.S. Pat. Nos. 7,316,704, 7,331,979, 7,335,220 and 7,806,856, and U.S. Patent Application Publication Nos. 2007/0231366, 2008/0082122, 2009/0088793, 2009/0254110, 2010/0168789, 2010/0274280 and 2010/0280546. The entire disclosures of these references are expressly incorporated by reference herein.

Figure 1E:
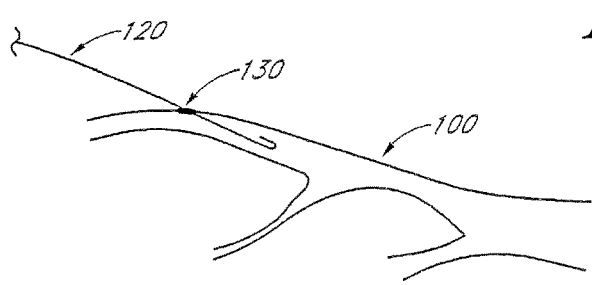

As shown in FIG. 1E, next the balloon 122 may be deflated, and the guide wire device 120 may be withdrawn through the closed arteriotomy. In these embodiments, the sealant 130 may be capable of closing the hole left by the guide wire device 120 after withdrawal.

Figure 2A:
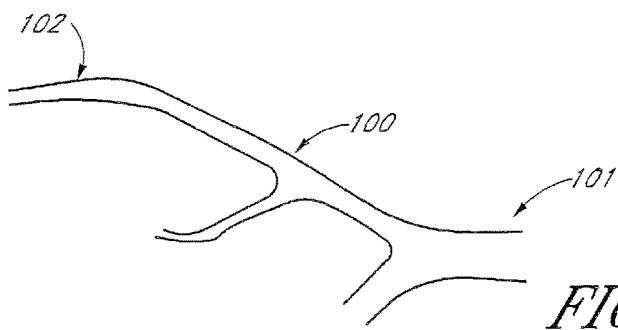
FIGS. 2A-2I are diagrammatic illustrations of a femoral artery, iliofemoral segment and aorta portion, showing an exemplary method for stabilizing vascular injuries and managing blood flow during interventions to treat vascular injuries, according to one embodiment.
Figure 2B:
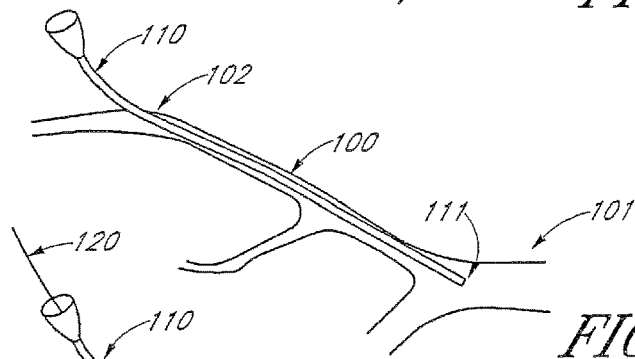
Figure 2C:
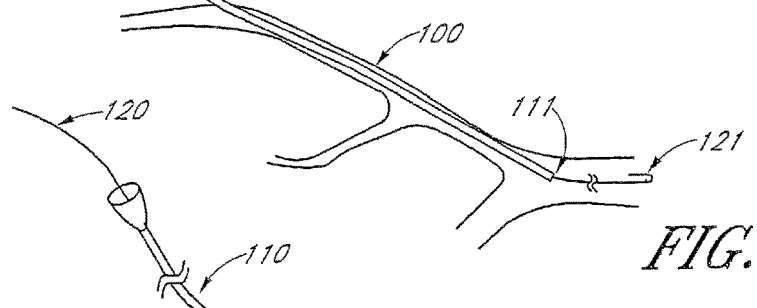

Referring now to FIGS. 2A-2I, another method is provided for managing vascular complications and/or controlling bleeding during or after trans-femoral catheterization. FIG. 2A again illustrates the femoral artery 102, iliofemoral artery 100 (or "iliofemoral segment") and a small portion of the aorta 101. As shown in FIG. 2B, the method may initially include inserting a vascular access sheath 110 (or "procedure sheath") into the femoral artery 102 and advancing its distal end 111 into the iliofemoral segment 100 for conducting a catheterization procedure, similar to the previous embodiment. In most embodiments, the vascular access sheath 110 will be used for performing one or more intravascular or transvascular procedures, such as but not limited to EVAR or TAVI (also called transvascular aortic valve replacement, or "TAVR"). Next, as illustrated in FIG. 2C, upon completion of the procedure, and before withdrawing the vascular access sheath 110, a guide wire balloon device 120 (for example, any of the embodiments described elsewhere herein or in the applications incorporated by reference herein) may be inserted into the procedure sheath 110, such that a tip 121 of the guide wire device 120 is positioned past the sheath tip 111 inside the aorta 101 (or other body lumen).

Figure 2D:
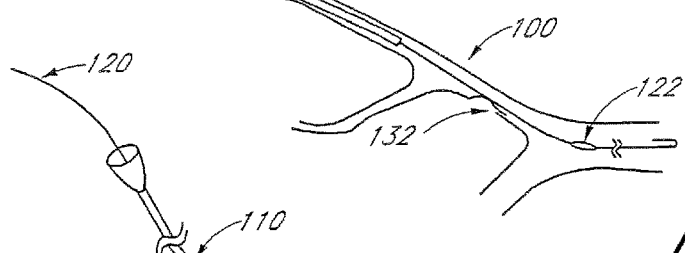
Figure 2E:
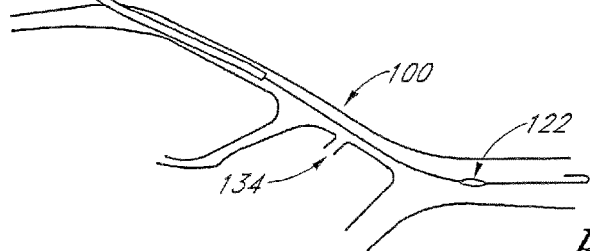
Figure 2F:
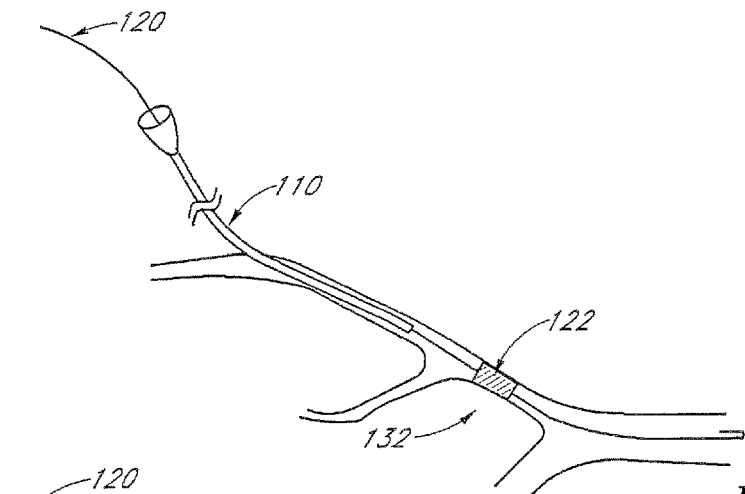

Referring to FIGS. 2D and 2E, the sheath 110 may then be withdrawn, for example, under angiographic guidance, while maintaining the position of the guide wire device 120 in the iliofemoral artery 100. If sheath withdrawal uncovers a vascular injury, such as dissections 132 (shown in FIG. 2D) or perforations 134 (shown in FIG. 2E), expedient catheter management of the injury is possible by the guide wire device 120, which is positioned in the true lumen of the vessel 100. As shown in FIG. 2F, as a first step, the balloon 122 may be positioned at the location of the vascular injury 132 and inflated, in an effort to stabilize the vessel wall at the site of injury, and/or to bridge the complication for further treatment options.

Figure 2G:
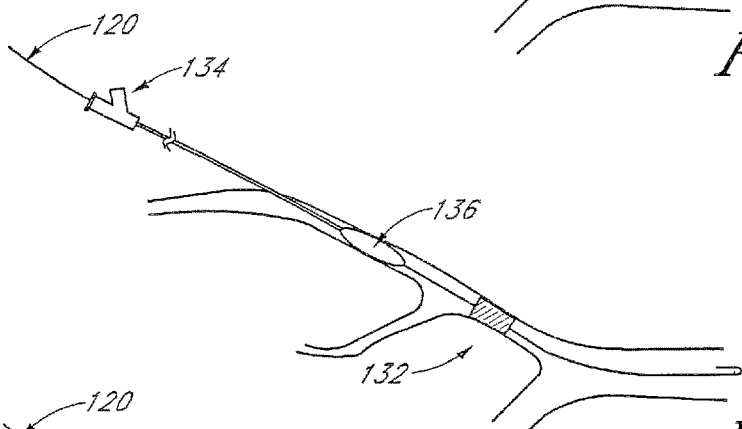

With reference to FIG. 2G, the guide wire device 120 may provide a path for ipsilateral insertion of a treatment device, such as a catheter 134 with a balloon 136 and possibly a stent mounted on the balloon 136, for treating the vascular injury 132. In most or all embodiments, the guide wire device 120 may be "hubless," meaning that once an inflation device (not shown) is removed from the device 120, one or more instruments may be passed over the proximal end of the guide wire device 120 without having to remove or navigate over a proximal hub. This hubless feature provides a significant advantage in ease of use for passing one or more additional devices to the area of the vascular injury. In other embodiments, alternative or additional treatment devices may be advanced over guide wire device 120, such as but not limited to any suitable catheter device, such as balloon expandable devices, stent delivery devices, graft delivery devices, radiofrequency or other energy delivery devices or the like. Under such scenarios, the device(s) 134 may be inserted into the target vessel over the guide wire device 120 while the injury is stabilized and bleeding is minimized by the expanded balloon 122, as shown in FIG. 2G.

Figure 2H:
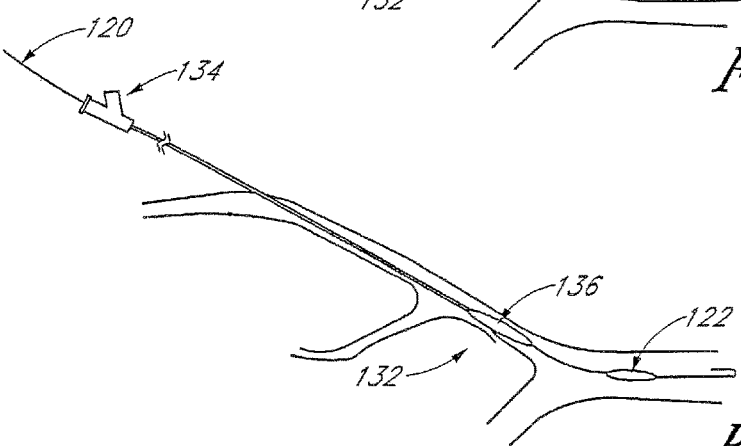
Figure 2I:
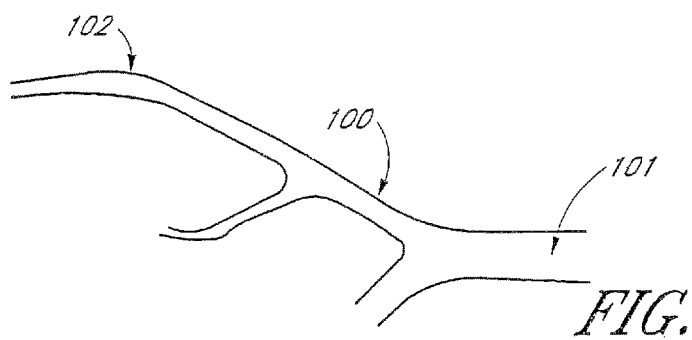

Referring now to FIG. 2H, to facilitate positioning of a treatment device 134, the balloon 122 of the guide wire device 120 may be deflated and moved as desired within the vessel, for example, to an upstream location, as shown. Optionally, the tip 121 may be positioned past the iliofemoral segment 100 in the aorta 101 at anytime during the procedure, for example, in order to prevent tip-related injury. In such procedures, the floppy tip 121, which may include the entire length distal to the balloon 122, may be sufficiently long to extend into the aorta when the balloon 122 is positioned in the iliofemoral segment 100. For example, in various embodiments, the tip 121 may be at least longer than the average length of the iliofemoral segment 100, such as at least about 15 cm, more preferably at least about 20 cm, and even more preferably between about 20 cm and about 25 cm.

In the embodiments described above, the guide wire device 120 and therapeutic device(s) 134 are advanced to the injury site through vasculature on the same side of the patient's body that the procedural vascular access sheath 110 was placed. For the purposes of this application, this side of the patient is referred to as the ipsilateral side of a patient. In other words, in this application, "ipsilateral" refers to the side of the patient's body on which the main access was achieved for performing a given endovascular procedure. For example, the "ipsilateral femoral artery" or "ipsilateral iliofemoral artery" will generally be the artery in which a vascular access sheath 110 (or any other access device) is placed for advancing instruments to perform the intravascular procedure (TAVI, EVAR, etc.). "Contralateral" refers to the opposite side of the patient, relative to the procedure access side. In this regard, "ipsilateral" and "contralateral" relate to the side on which access is gained to perform the main procedure and do not relate to where the physician stands to perform the procedure. In any case, various embodiments of the methods and devices described herein may be used exclusively via an ipsilateral approach, exclusively via a contralateral approach, or interchangeably via an ipsilateral or contralateral approach.

The method just described in relation to FIGS. 2A-2I may have a number of advantages over the prior art contralateral balloon occlusion technique (CBOT). One advantage, for example, is that the guide wire balloon device 120 will typically be located very close to the vascular injury 132, 134 when the vascular sheath 110 is withdrawn. Thus, the balloon 122 may be inflated quickly within the iliofemoral artery 100, aorta 101 or femoral after 102, perhaps after minor positional adjustments, to quickly occlude the vessel and stabilize the injury 132, 134 while treatment options are being assessed and prepared. Another potential advantage of the method described above is that only one combined guide wire balloon device 120 is needed to stop blood flow/stabilize the injury 132, 134 and to provide a path along which treatment device(s) 134 may be advanced into the vessel. In other words, the method does not require multiple different guidewires, guide catheters, introducer sheaths and the like, nor does it require difficult threading of a guidewire into a contralaterally placed sheath. In general, therefore, the described method may be easier and quicker to perform, thus facilitating a quicker and more effective vascular repair.

FIG. 3 illustrates one embodiment of a guide wire device 300 for performing the various procedures described herein, such as occluding an artery to stop blood flow past a vascular injury and to provide a path for delivering one or more treatment devices to the injury site. Generally, the guide wire device 300 may include a hollow guide wire body having a central lumen 320, an occlusion balloon 302 (or other expandable member) attached to or otherwise carried on a distal end of the guide wire 300 adjacent a distal tip of the guide wire 300, and a hubless extracorporeal or proximal end 303 including a valve with an inflation port 306 in communication with the lumen 320 and a balloon inflation port 305.

The guide wire device 300 may have dimensions and/or characteristics similar to conventional guide wires. For example, the guide wire device 300 may allow for introduction of other devices, such as catheters or other tubular devices carrying therapeutic and/or diagnostic elements (for example stents, covered stents, stent-grafts, balloons, etc.) In certain embodiments, the guide wire device 300 (including the balloon 302 in a collapsed state) may be sized to be received in and/or to occlude an arterial or other body lumen, for example, sized between about 3 mm and about 15 mm in some embodiments and in other embodiments as large as about 30-40 mm. The guide wire device 300 may also have a sufficient working length to allow introduction of other devices over the guide wire shaft.

The entire length or the distal end of the guide wire device may be made of compliant material that provides a flexible shape and/or accommodates the distal end conforming to the target lumen geometry. Alternatively, the proximal end 303 may be rigid, semi-rigid, or simply stiffer than the distal end to facilitate advancement of the guide wire device 300 from the proximal end 303.

In some embodiments, the central lumen 320 of the guide wire 300 may communicate with the external surface or environment of the device through a series of valves (or other flow regulators) for example, within or on the proximal end 303 of the guide wire device 300.

In some embodiments, the deflated balloon 302 may have an overall low profile substantially similar to the guide wire shaft dimension, for example, such that at least the distal end has a substantially uniform diameter and/or the entire length of the guide wire device 300 has a substantially uniform diameter.

In certain embodiments, the proximal end 303 of the guide wire shaft may be attached to a detachable inflation unit for balloon 302 inflation/deflation. The inflation unit may be sealingly attached around or otherwise to the balloon shaft to provide inflation.

Some embodiments may include a fluid regulation system, for example, within the proximal end 303 of the guide wire shaft, that maintains inflation/deflation state during operation, for example, when the inflation unit has been utilized to inflate or deflate the balloon 302 and then removed. The fluid regulation system may include a plurality of fluid regulators that are serially installed in order to maintain the balloon 302 in an inflation state, for example, in case of failure of an individual fluid regulator (for example, as a result of balloon catheter manipulation). In one embodiment, the fluid regulator system may include an internal fluid regulator and an external fluid regulator, which are operatively coupled such that opening the internal fluid regulator may cause the external fluid regulator to open as well. The fluid regulation system may also include one or more mechanisms designed to automatically lock at least one fluid regulator. In certain embodiments, the fluid regulator system may also include one or more protective features to prevent or minimize accidental manipulation, kinking etc., which may adversely affect inflation or deflation status. For example, one or more protective sleeves, caps, segments of enhanced stiffness, locking mechanisms, etc. (not shown) may be provided.

In one embodiment, the guide wire shaft may be configured to accept parts that enable extension of the guide wire shaft. For example, a shaft extension mechanism may be connected to the fluid regulator system in an effort to simplify overall design.

In certain embodiments, the guide wire device 300 may be compatible with vascular closure devices, for example, utilizing sutures, clips, and other implants, etc. The guide wire device 300 may also include one or more radiographic markers, for example, on the distal end adjacent to the balloon 302, to aid radiographic positioning.

FIG. 3 shows an exemplary embodiment of a guide wire balloon device or system 300 that includes a guide wire shaft or other outer tubular member including a proximal end 303, a distal end terminating in a substantially non traumatic distal tip 301, and a balloon or other expandable member 302 carried on the distal end. The balloon 302 may be formed from a soft membrane 304, for example, to provide a compliant balloon. The balloon 302 communicates with an internal guide wire lumen 320 of the guide wire shaft, for example, via one or more inflation ports 305 in a side wall of the tubular member. Optionally, an internal wire may be provided within the guide wire shaft, for example, within the lumen 320, to stiffen, straighten, or otherwise support the distal end or the entire length of the guide wire shaft. The internal wire may be smaller than the lumen 320, as shown, for example, to accommodate fluid delivery through the lumen 320 around the internal wire. Optionally, the distal tip 301 may include a "J" tip and/or other features (not shown) beyond the balloon 302, similar to conventional guide wires, if desired.

The proximal (extra-corporeal) end 303 of the guide wire device 120 may be connected to an inflation device (not shown) for balloon inflation and deflation. In addition, the proximal end 303 may have an integrated flow regulator (valve) system designed to maintain balloon 302 inflation/deflation state, for example, when inflation device is disconnected, such as the embodiments described elsewhere herein and/or in the applications incorporated by reference herein.

Turning to FIGS. 4A and 4B, an exemplary embodiment of a fluid regulator (valve) system is shown that includes an internal piston 309 that may be directed to sealingly engage and disengage an internal valve 307 within the proximal end 303 of the guide wire shaft, for example, when piston shaft 308 is moved axially relative to the guide wire shaft. For example, as shown in FIG. 4A, the piston shaft 308 may be advanced distally until the piston 309 engages the valve 307 in a distal position. Thus, in the distal position, the lumen 320 of the guide wire shaft may be substantially sealed, for example, after delivering sufficient fluid into the lumen 320 to inflate the balloon 302. Conversely, as shown in FIG. 4B, the piston shaft 308 may be retracted proximally until the piston 309 reaches a proximal position proximal to an outlet or side port 306 in a side wall of the proximal end 303 of the tubular member. The internal lumen 320 may communicate with the external environment adjacent the proximal end 303 through the outlet 306 when the piston shaft 308 is retracted to the proximal position such that fluid may be delivered into or evacuated from the lumen 320, for example, to inflate or deflate the balloon 302 (not shown). Optionally, a low profile plunger (not shown) may be provided on the proximal end of the piston shaft 308 outside the proximal end of the guide wire shaft to facilitate actuation of the valve system. Alternatively, a cap (not shown) similar to other embodiments herein may be provided on the proximal end of the guide wire shaft that is coupled to the piston shaft 308. The cap may have a profile small enough to accommodate advancing supplementary devices (not shown) over the cap onto the guide wire shaft. For example, the proximal end of the guide wire shaft may be smaller than the adjacent length of the guide wire shaft such that the cap provides a substantially uniform outer diameter ("O.D.") on the guide wire device.

Figure 5A:
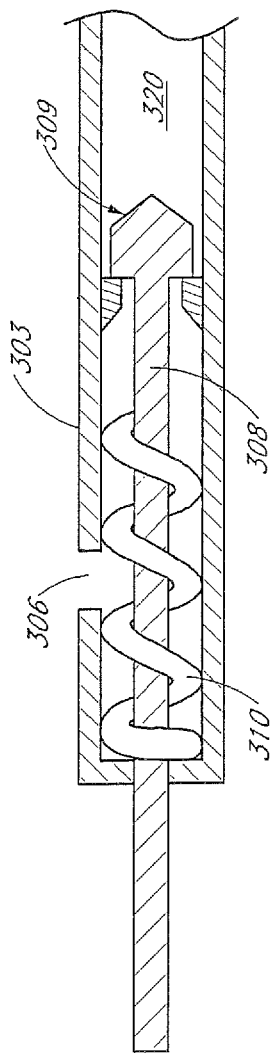
FIGS. 5A and 5B are cross-sectional side views of another alternative embodiment of a valve section (fluid regulator/valve), shown in a valve-closed configuration (FIG. 5A) and a valve-open configuration (FIG. 5B), which may be included in a guide wire device, such as the guide wire device shown in FIG. 3.
Figure 5B:
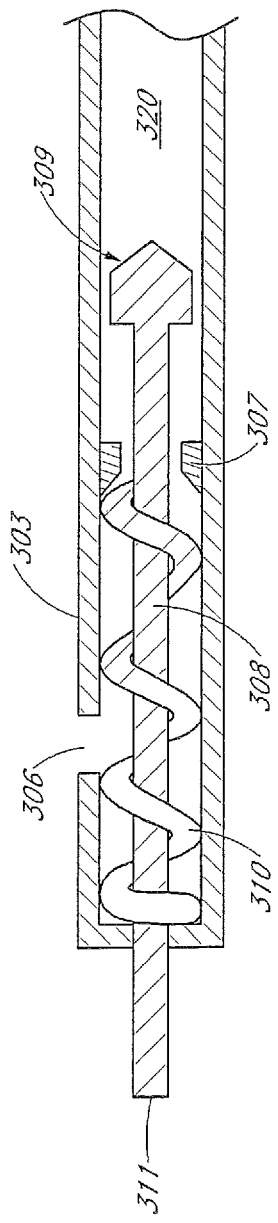

Turning to FIGS. 5A and 5B another embodiment of a fluid regulator (valve) system is shown that may be provided on the proximal end 303 of a guide wire device, such as device 300 described above. In this embodiment, the internal piston 308 is driven by a spring 310, for example, a tension spring, which, in a substantially relaxed or relatively lower energy position (FIG. 5A) maintains a substantially sealed and/or closed fluid regulator (valve) system. As shown in FIG. 5B, when the piston 308 is moved distally relative to the guide wire shaft, the internal valve 307 may be opened to allow communication between the internal lumen 320 and the external environment of the guide wire device through outlet or side port 306. When the piston shaft is advanced distally to open the valve 307, the spring 310 may be subjected to increased tension such that, when the piston shaft is released, the piston shaft may resiliently retract proximally to engage the piston 308 with the valve 307 to automatically seal the lumen 320, for example, after inflating or deflating the balloon (not shown), similar to the previous embodiments.

FIGS. 6A and 6B show yet another embodiment of a fluid regulator (valve) system that may be provided on a guide wire device, such as any of the embodiments herein, whereby an external cap 312 covers the outlet or side port 306 that communicates between the guide wire internal lumen 320 and the external environment of the guide wire device 300. The cap 312 may be moved relative to the outlet 306, for example, between a proximal position (shown in FIG. 6A) and a distal position (shown in FIG. 6B) to open and substantially seal the outlet 306, for example, to allow fluid to be delivered into and evacuated from the lumen 320, similar to the previous embodiments.

Turning to FIGS. 7A and 7B, still another embodiment of a fluid regulator (valve) system is shown that may be provided on a balloon guide wire device. Unlike the previous embodiments, the system includes an internal valve element 307 and an external valve element 306, which are operatively (serially) connected such that a single actuation step may open both valves (as shown in FIG. 7A) or close them (as shown in FIG. 7B). Such a combination of valves may assure that flow within wire's internal lumen 320 is controlled to maintain a desired balloon inflation state.

In certain embodiments, devices and methods described herein may be compatible with existing devices and workflow, for example, such that the guide wire device may be the last device to be removed from the target artery. Therapeutic device exchanges may be possible while vascular complications are stabilized endovascularly with a balloon. This may be especially significant, for example, if bleeding occurs at vascular segments that are inaccessible for manual compression (for example, the iliac artery, the proximal femoral artery, specific patient anatomy, etc.).

In certain clinical scenarios, there might be a need for the guide wire device to be introduced before or during sheath advancement, i.e. through devices with true wire lumens. Therefore, in some embodiments, the guide wire device may have a uniform diameter over the entire length including the inflatable segment and the distal tip.

The devices and methods described herein may also ensure that access to the true lumen of the target vessel is maintained, when vascular complications are anticipated, but before they are encountered.

In some embodiments, the devices and methods described herein may facilitate an ipsilateral approach, for example, for better device control and improved blood loss management.

In certain clinical scenarios, it may be necessary to obtain angiographic guidance during insertion/withdrawal/maneuver of the guide wire device. Therefore, the guide wire device could incorporate mechanisms allowing for contrast injection at or close to the distal tip of the device. Such mechanisms may include channels, valves, and orifices for contrast injection. Alternatively, a custom sheath could be used in conjunction with the guide wire device. Such a custom sheath may be sufficiently dimensioned for housing the guide wire device and allowing for simultaneous contrast flow. The custom sheath may be equipped with a contrast injection port and an extracorporeal valve that prevents contrast back-flow during injection.

In special clinical scenarios, it may also be useful to assess intravascular pressure, flow, temperature, general morphology, or other properties of the anatomy encountered, for example, to interrogate a special condition beyond angiography. In one embodiment, the guide wire device or system may include elements providing physiological or image data during operation. These elements may include one or more pressure, flow and/or temperature sensors, and/or ultrasound, light, infrared, or other imaging elements. Additionally, one or more features may be provided for assessing intravascular dimensions, including balloon inflation dimension and/or pressure, for example, for estimating vessel sizes, and/or for targeting a specific inflation threshold.

The devices and systems herein may also have characteristics that allow it to be integrated into a robotic vascular surgery environment, such as the DaVinci system, the Zeus System, the Sensei system, etc.

In special scenarios, additional treatment to a body lumen or other target segment may be needed beyond balloon inflation. In one embodiment, the system may provide capabilities of local drug or agent or energy delivery through the guide wire system, for example, more desirably through the balloon.

In special scenarios, it may also be useful to provide a source of therapeutic and/or diagnostic agents, for example, including one or more devices for injection of agents about the target treatment area. For example, the system may include a syringe, pump, or other source for intravascular injection of agents. Such guide wire devices may include an extracorporeal injection port in the proximal end, an injection channel or other lumen, and/or a distal agent release port located in proximity to the balloon.

In certain clinical scenarios, the best therapy option is endovascular stent implantation. The guide wire device may, thus, incorporate a stent delivery system that is readily available for treatment or in anticipation of vascular injuries.

The guide wire device may integrate additional lumens for introduction of therapeutic/diagnostic agents/devices. Alternatively, the guide wire system may be provided with a larger sheath that can be introduced over the wire, thereby forming a channel around the external surface of the wire.

In cases where prolonged flow occlusion is desired, it may be useful to provide simultaneous occlusion of a target region, and perfusion of distal regions. Therefore, the guide wire device or system may include tissue perfusion across the balloon occlusion area. Such features may include perfusion channels in the shaft or balloon, for example, with appropriate ports, valves, and/or flow drivers.

In special clinical scenarios, it may be useful to isolate a specified segment of a body lumen for diagnostic or treatment purposes. In one embodiment, the guide wire system can be combined with a standard balloon catheter to create a double-balloon catheter system that is capable of isolating a targeted vessel or other bodily passages.

In certain embodiments, the balloon may provide an anchoring mechanism for the guide wire device, for example, such that over-the-wire device insertion is facilitated.

In certain embodiments, the occlusion balloon may be conforming to the lumen shape, and may grow axially/longitudinally during inflation. The balloon could exhibit varying wall thicknesses to provide preferential inflation shape. For example, thinner sections inflate first followed by thicker sections as the thin walled portions contact the vessel wall. The balloon could be corrugated by thicker wall sections or Kevlar inflation restrictions to mitigate pressure on the vessel wall.

In some scenarios, balloon occlusion/inflation is required over long vascular segments. One embodiment could incorporate a device shaft with multiple balloon units that collectively cover a longer vascular segment. The balloon units could be collectively or individually connected to the same/multiple inflation system(s).

In certain clinical scenarios, balloon dilatation might be required. The guide wire balloon device could incorporate a balloon that fulfills occlusion and dilatation function.

In one embodiment, the guide wire device could be a closed system with balloon inflation agent stored inside a sealed tubing system. Collapse (or expansion) of the internal lumen of the tubing system would move the fluid into (or away) from the balloon thereby causing balloon inflation (or deflation). This embodiment foresees a tubing system that is not in communication with the external surface and has a pre-installed balloon inflation agent.

In special clinical scenarios, it may be desirable to have a system for facilitating device insertion through tortuous vascular segments. For example, it might be desirable to have a guide wire device or system that includes a flexible tip designed for retrograde insertion and a stiffer shaft proximal to the tip designed for facilitating over-the-wire device insertion through tortuous segments.

In certain clinical scenarios, vessel tortuosity may require straightening in order to ease device (sheath) insertion/retraction. The guide wire device could have a stiff shaft capable of non-traumatic straightening originally tortuous vessel. The stiffness could vary along the length. The distal section should be flexible and atraumatic.

In certain clinical scenarios, vessel tortuosity may require intravascular shape change of the distal tip. The proposed system may integrate steerability mechanisms that allow for temporary shape change of individual segments of the device.

Figure 8:
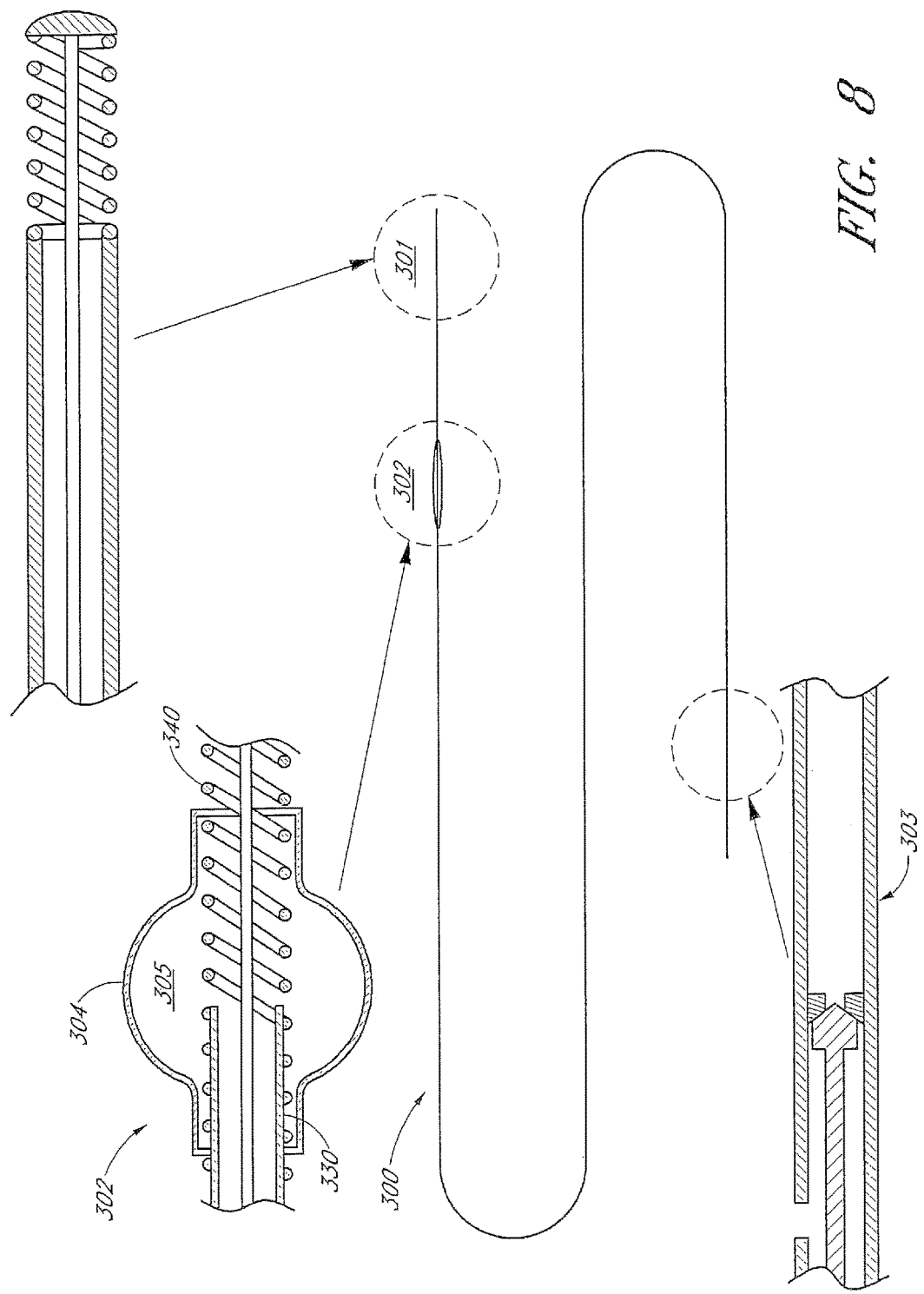
FIG. 8 is a side view of a guide wire balloon device, along with close-up, cross-sectional views of a distal tip, balloon section and valve section of the device, according to an alternative embodiment.
Figure 9B:
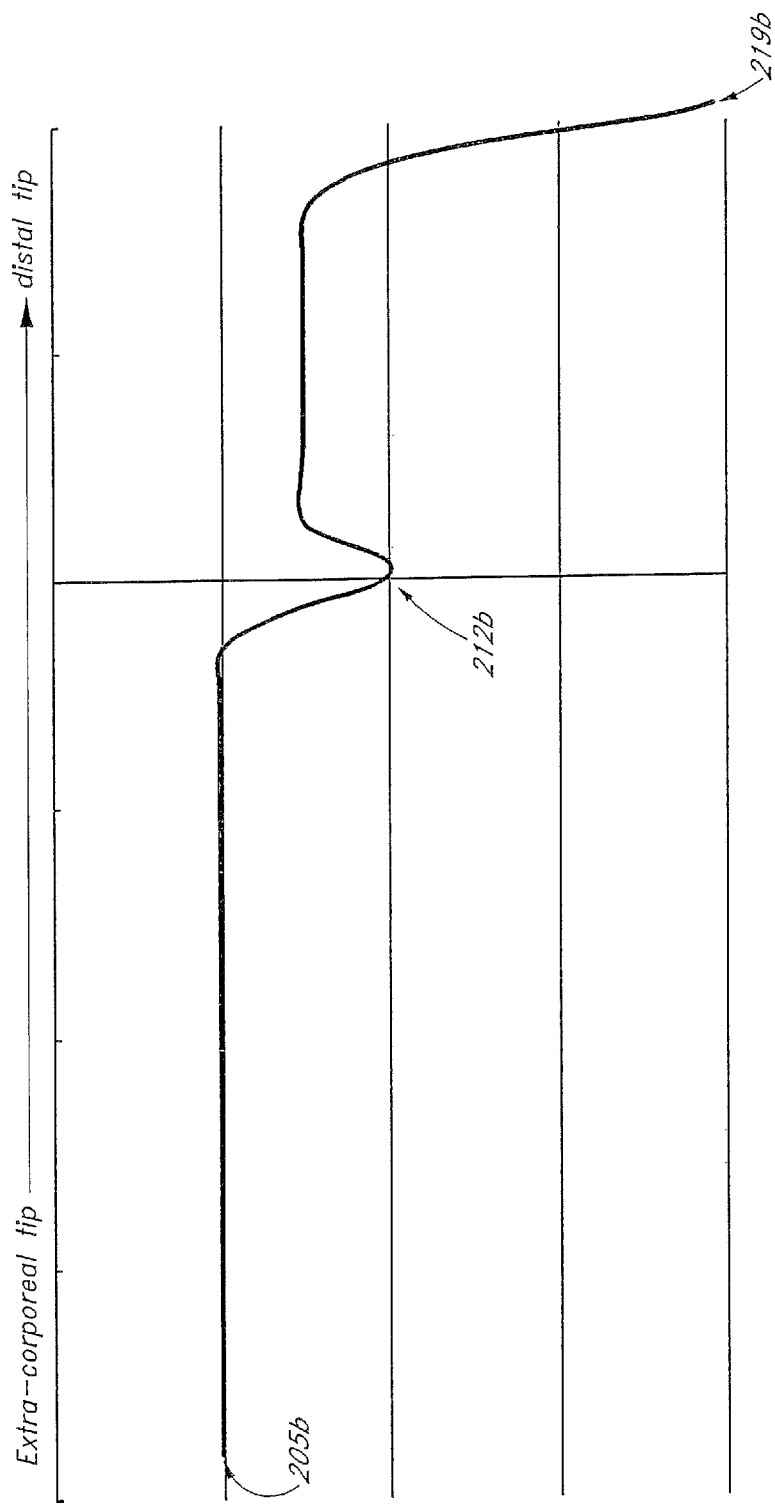
Figure 9D:
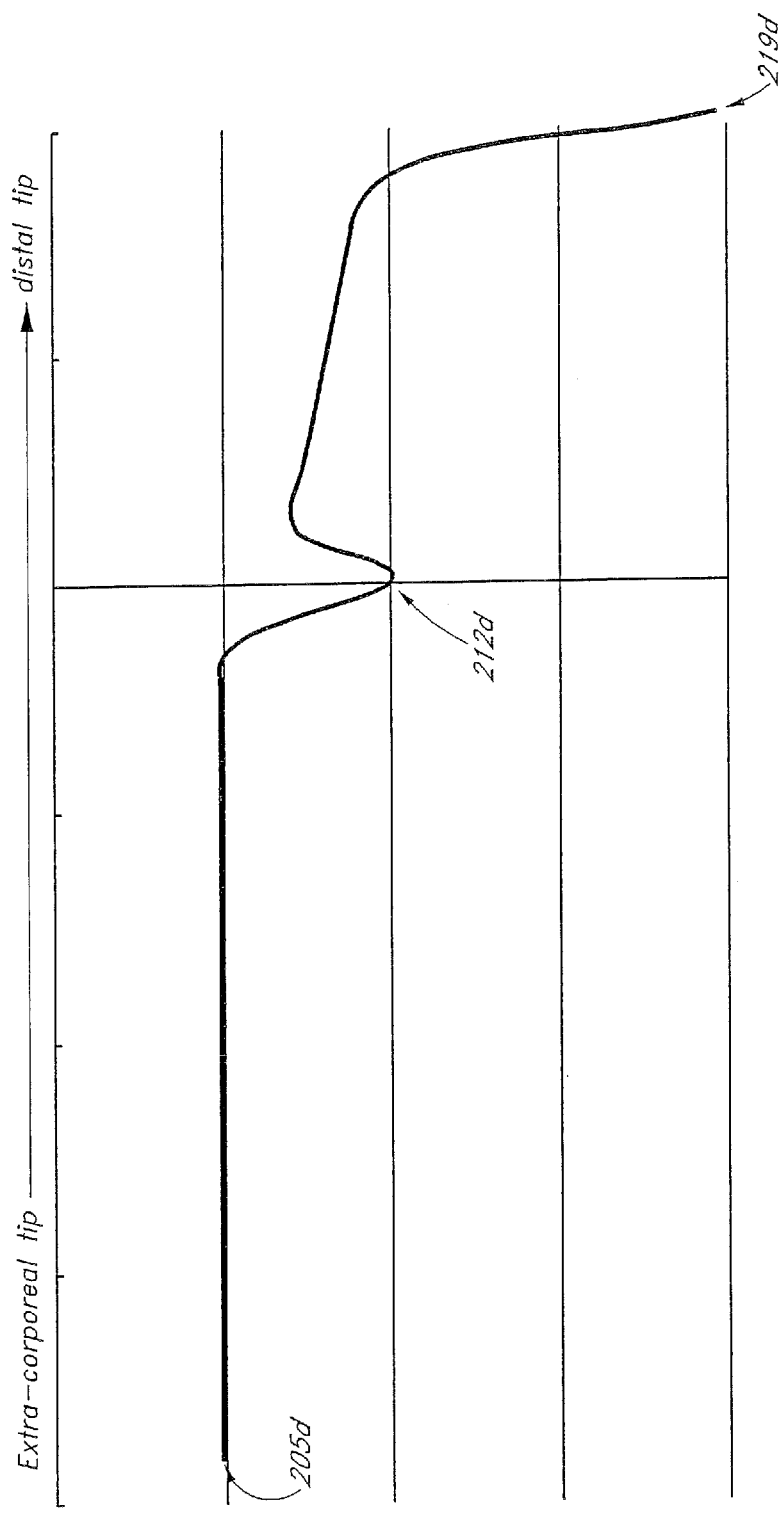
Figure 9E:
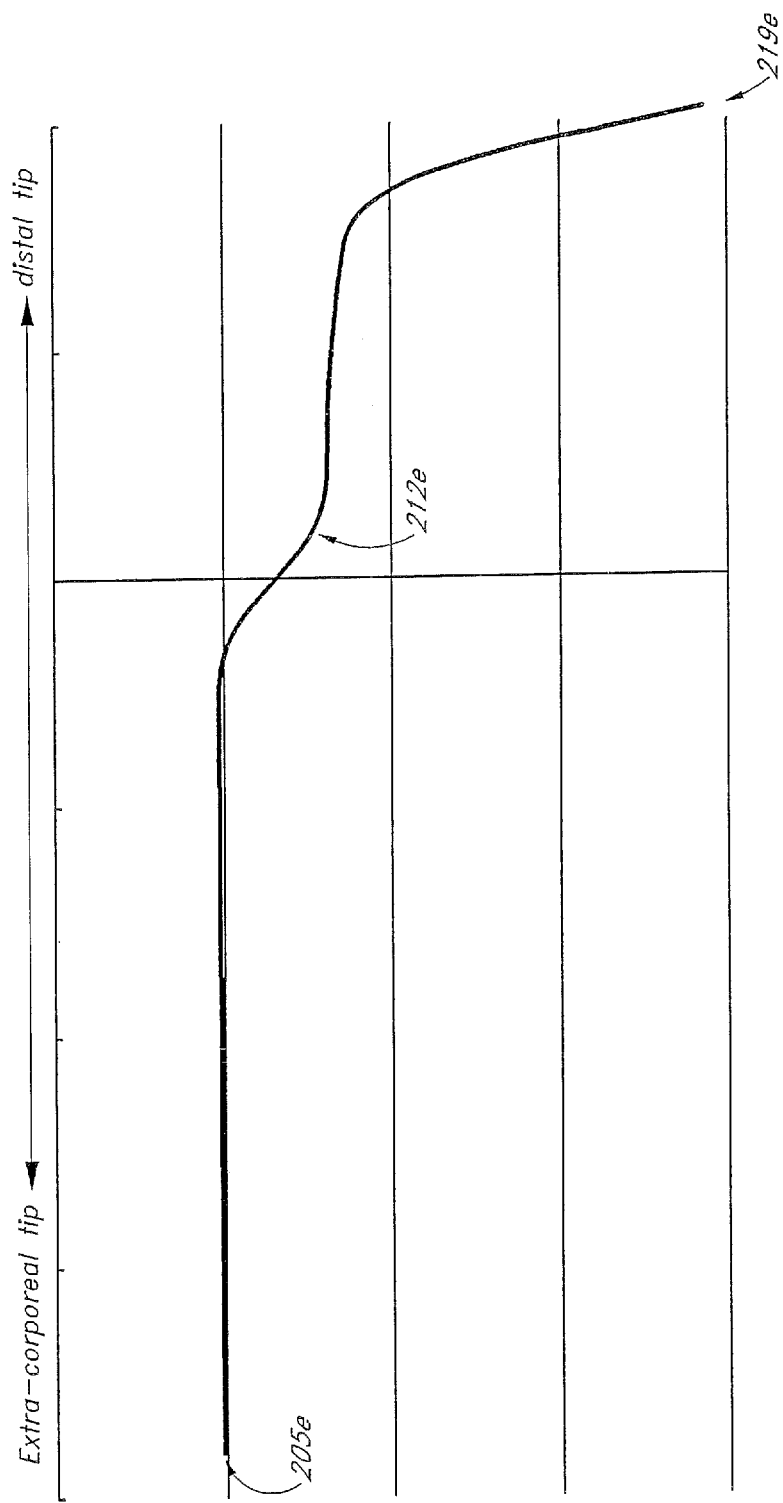
Figure 9F:
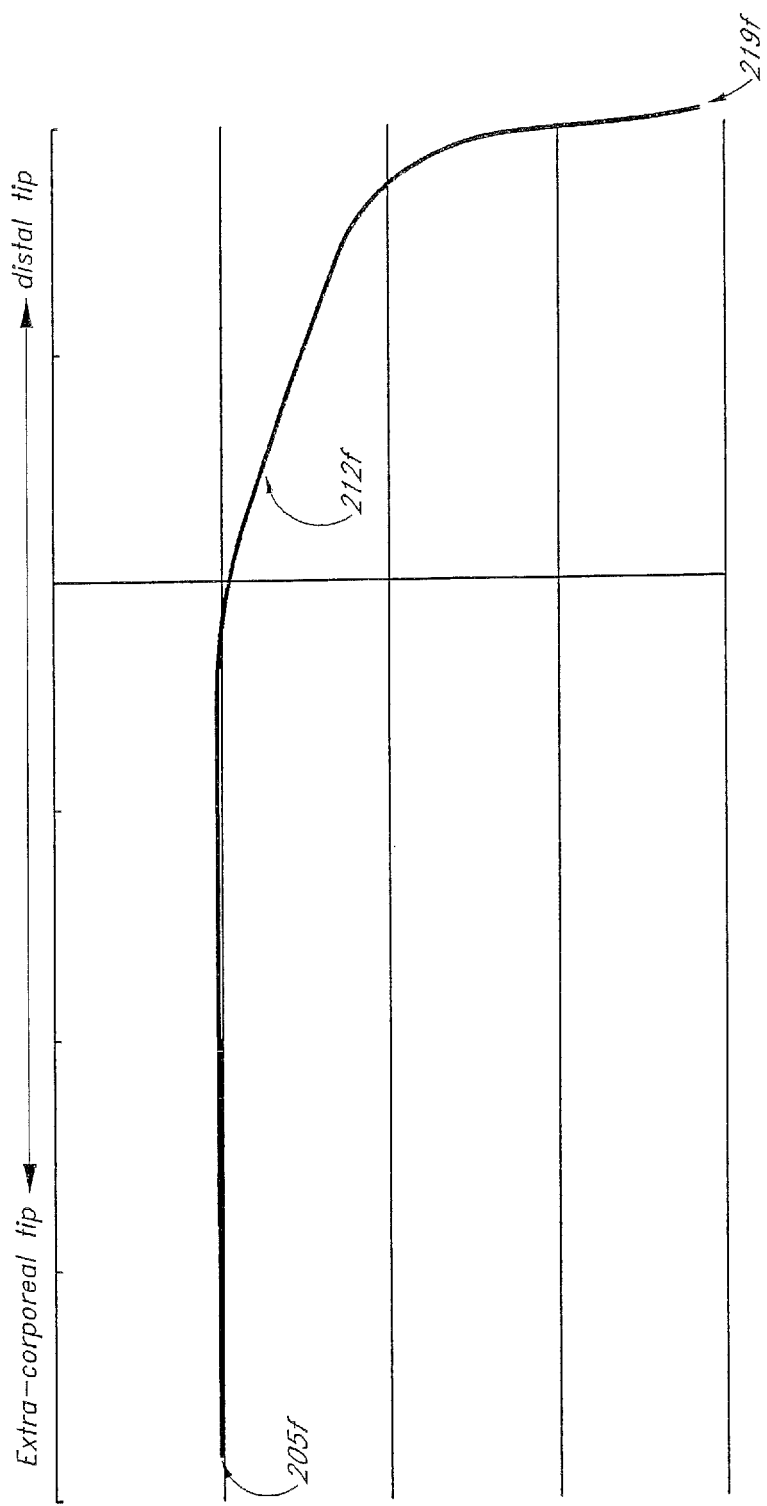
Figure 9G:
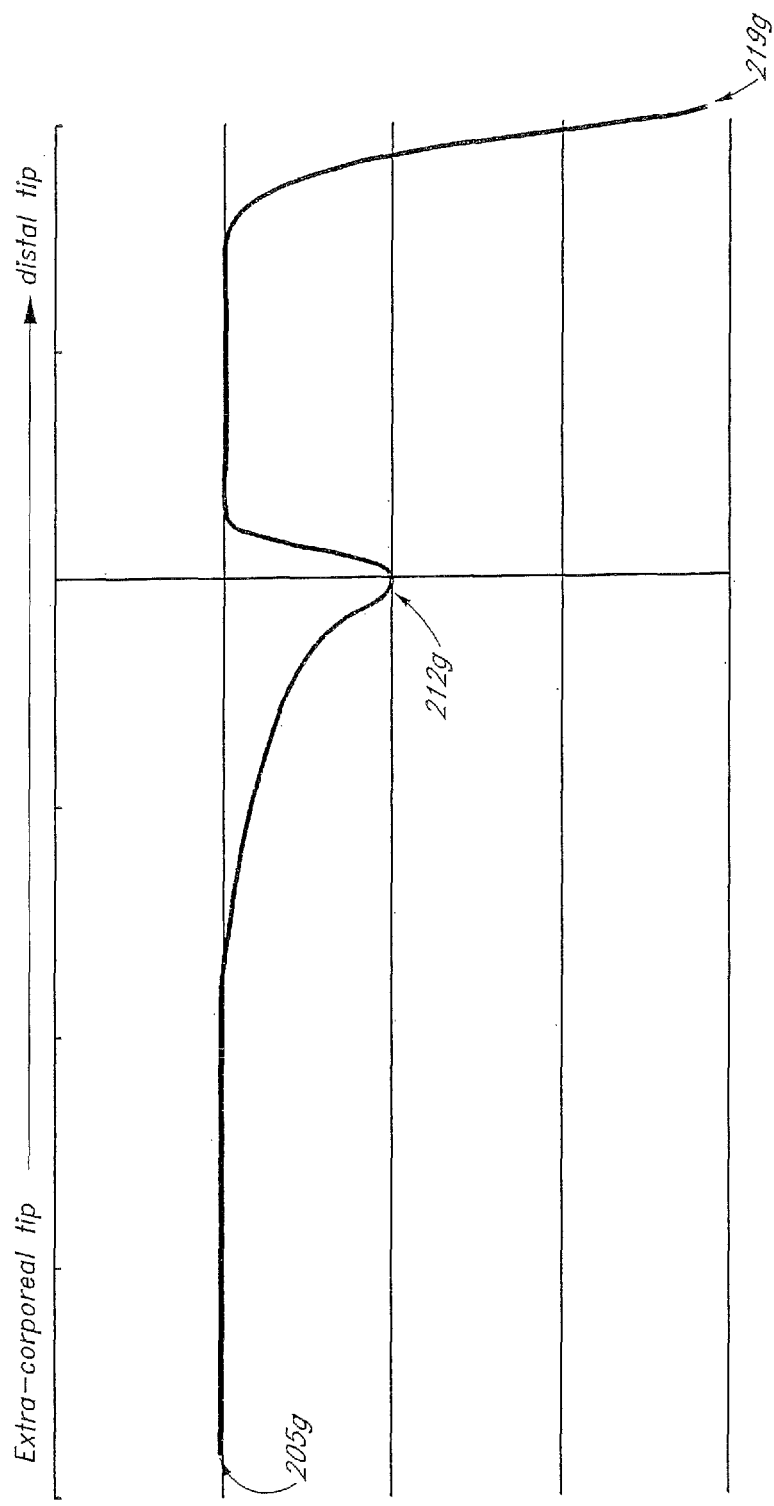
Figure 9H:
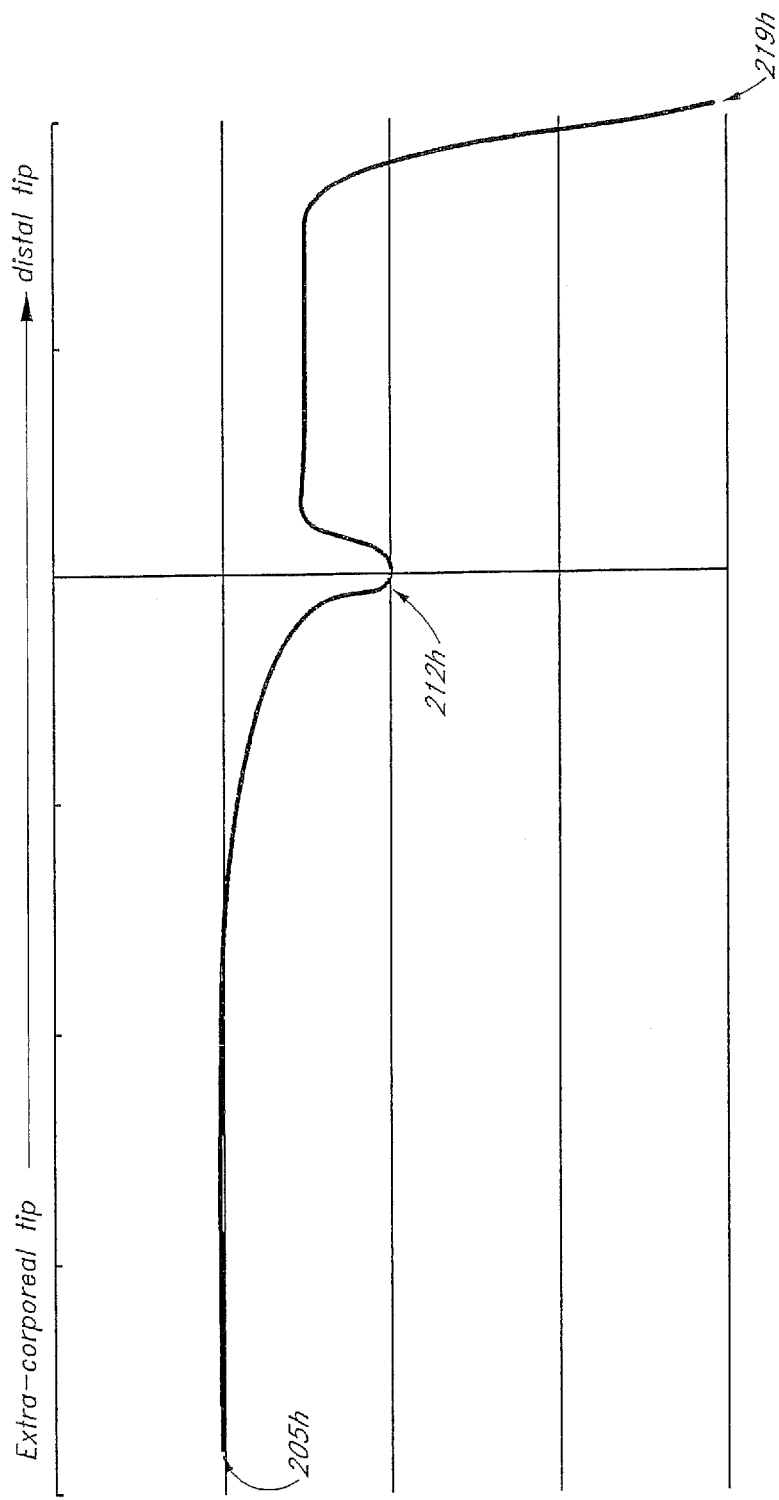
Figure 9I:
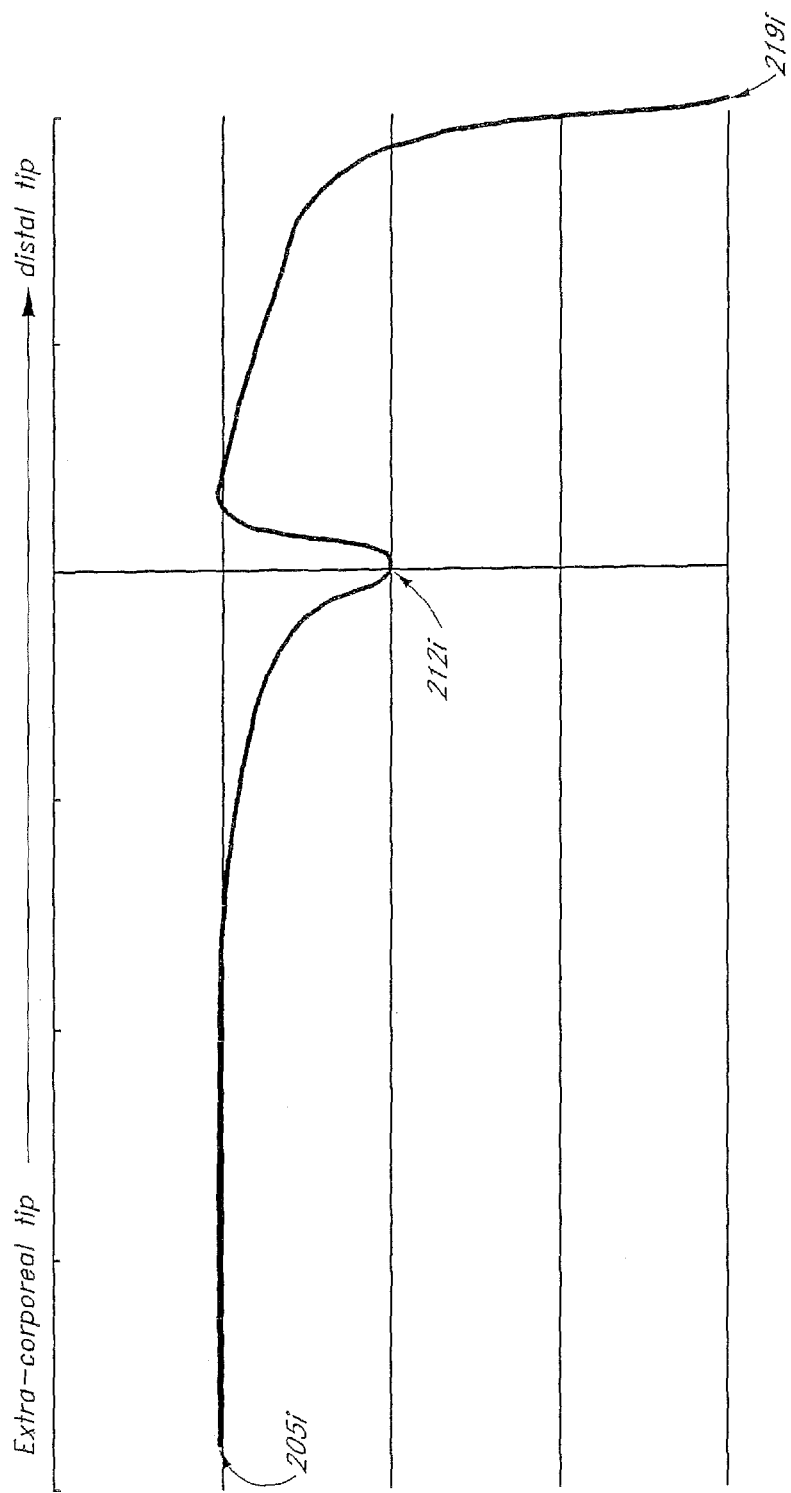
Figure 9J:
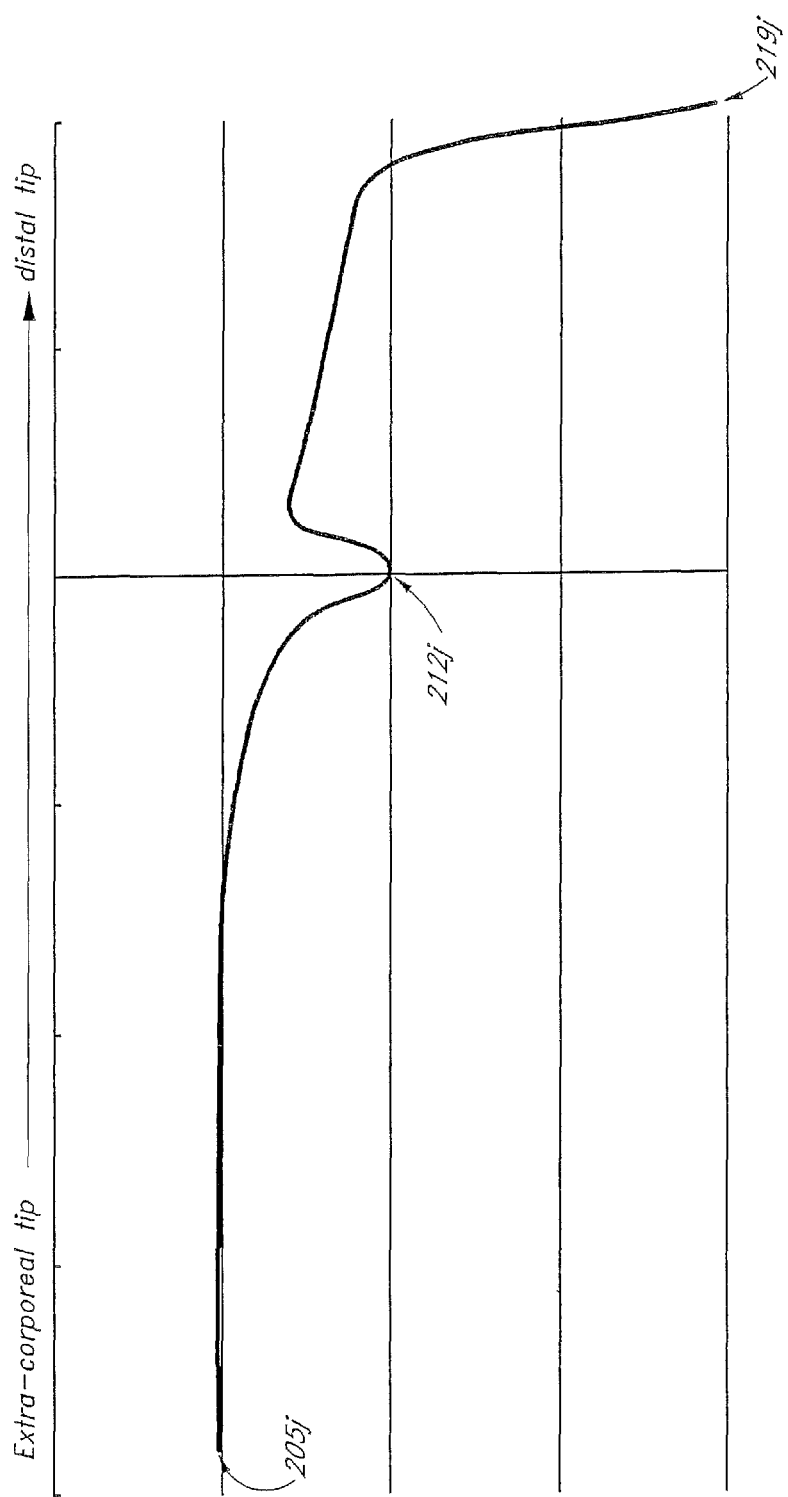
Figure 9K:
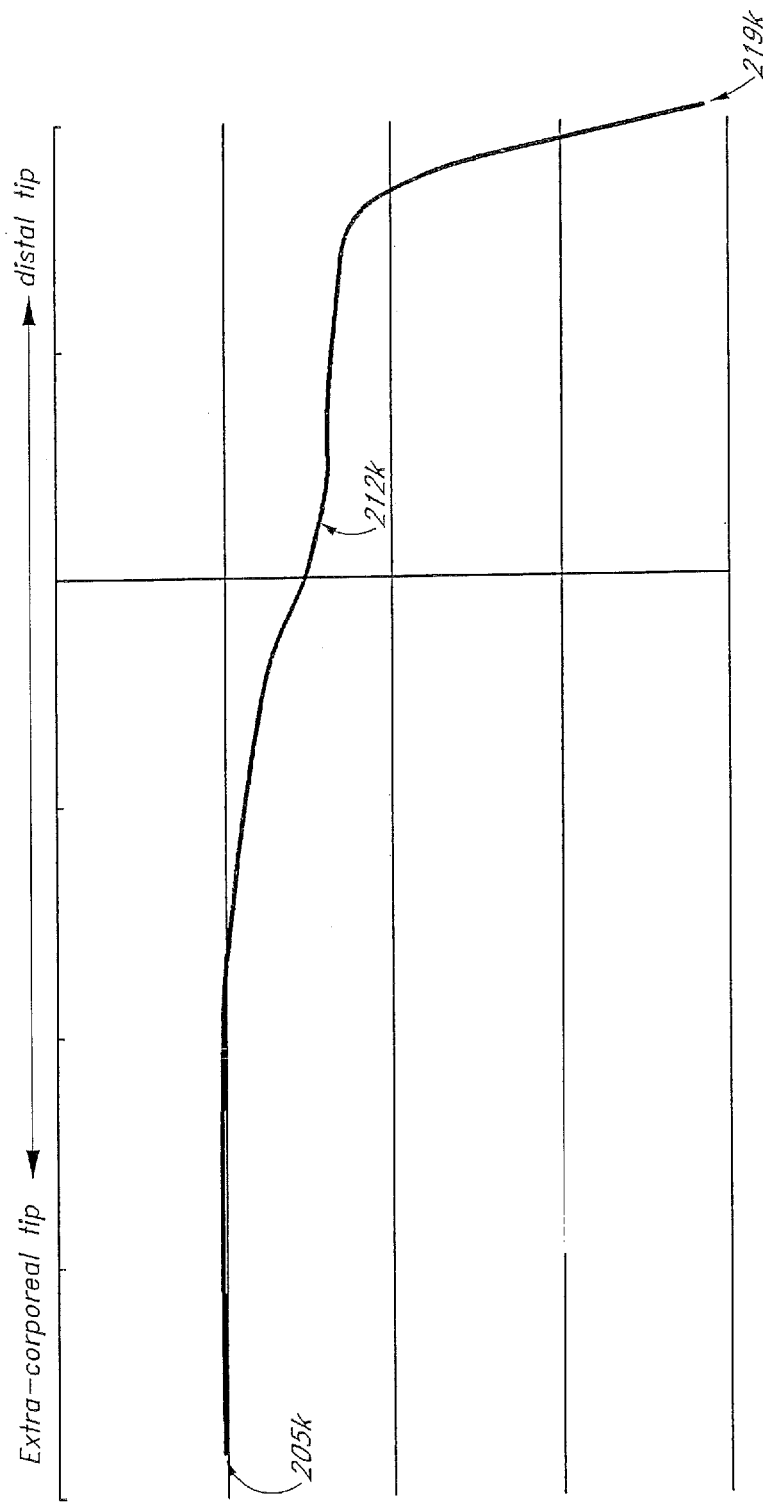
Figure 9L:
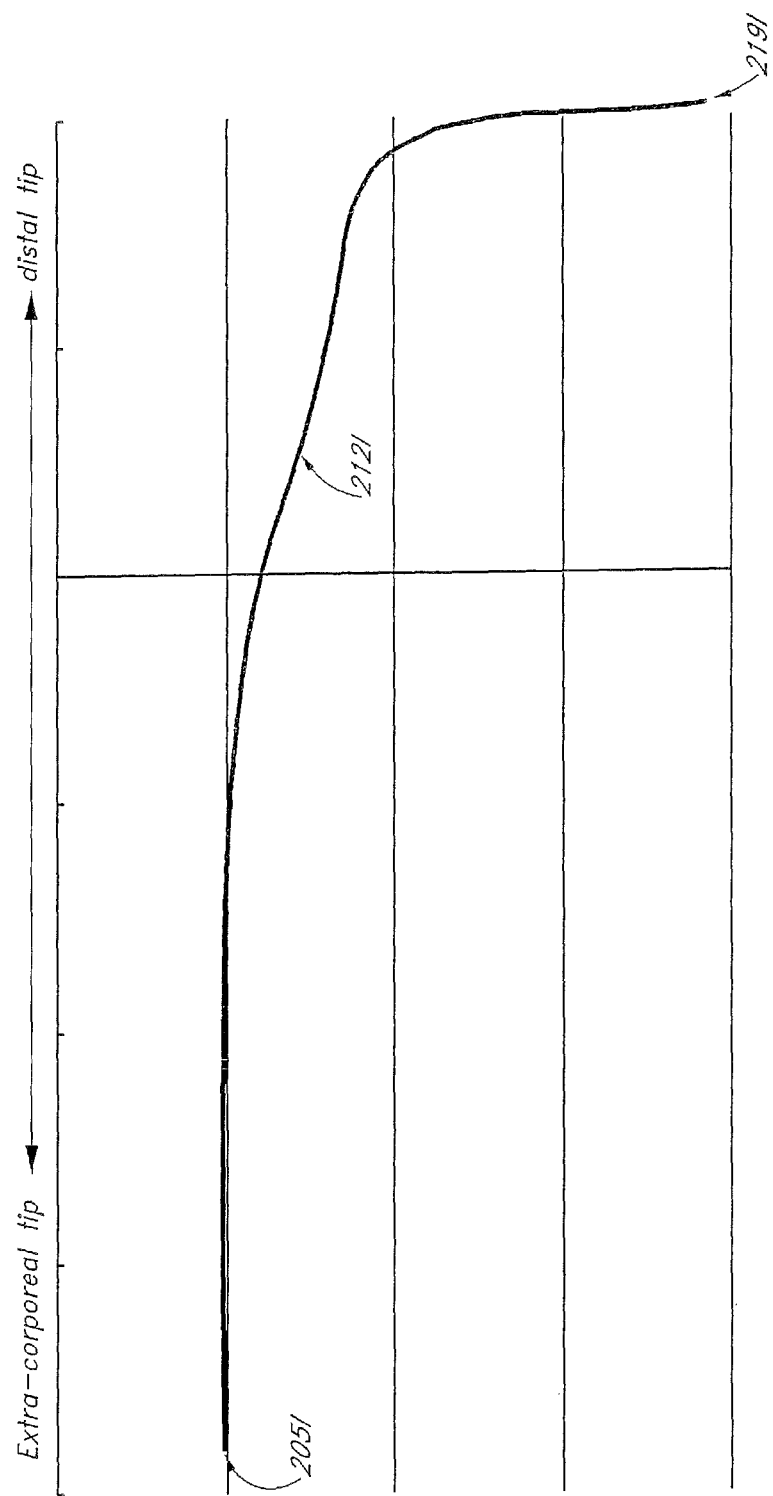

Referring now to FIG. 8, in certain clinical scenarios, the target treatment segment may be rigid and/or tortuous and may not respond to straightening attempts. Therefore, it would desirable for the balloon to adapt to vessel tortuosity. In one embodiment, the inflatable segment (i.e., the portion of the device 300 along which the balloon 302 is mounted) may include a more flexible, distal segment 340 (or joint), which allows for the inflatable segment to bend and provide flexibility, and a less flexible, proximal segment 330. The flexible segment 340 will not impact the balloon inflation functionality.

Referring now to FIGS. 9A-9L, in certain clinical scenarios, insertion or advancement of the guide wire device requires a minimum of catheter shaft back-bone support (stiffness). This guide wire characteristic is required for segments of the guide wire device such as the device shaft and the proximal part of the distal tip. FIGS. 9A-9L illustrate the stiffness characteristics of the balloon segment 212a-212l relative to the stiffness proximal and distal to the balloon segment 212a-212l, according to various alternative embodiments of the guide wire device. The stiffness/flexibility along each embodiment is designated, from a proximal end 205a-205l to a distal end 219a-219l. In the graphs, the upward direction designates more stiffness (i.e., less flexibility), and the lower direction designates less stiffness (i.e., more flexibility). In all the embodiments shown, the balloon segment 212a-212l may be described as a transition zone or transition segment between a proximal portion and a distal portion. Also, in all embodiments, there is a drop-off in stiffness (increased flexibility) in the balloon segment 212a-212l relative to the proximal portion. In some embodiments, such as those shown in FIGS. 9A-9D and 9G-9J, flexibility is greater in the balloon segments 212a-212d, 212g-212j of the guide wire devices than in the areas of the devices immediately proximal and distal to the balloon segments 212a-212d, 212g-212j. In alternative embodiments, such as those shown in FIGS. 9E, 9F, 9K and 9L, flexibility is greater in the balloon segments 212e, 212f, 212k, 212l of the guide wire devices than in the areas of the devices immediately proximal to the balloon segments 212e, 212f, 212k, 212l, but the portions of the devices immediately distal to the balloon segments 212e, 212f, 212k, 212l are either as flexible as, or more flexible than, the balloon segments 212e, 212f, 212k, 212l. In other alternative embodiments, other flexibility profiles may be possible. In general, however, it may be advantageous to have a balloon segment 212a-212l of a guide wire device that is positioned between a relatively proximal portion and a relatively stiff distal section, where the balloon segment 212a-212l is more flexible than at least the proximal portion.

In some embodiments, the removable inflation handle may integrate a torque system that provides torqueing of the guide wire device during operation if desired.

Figure 10:
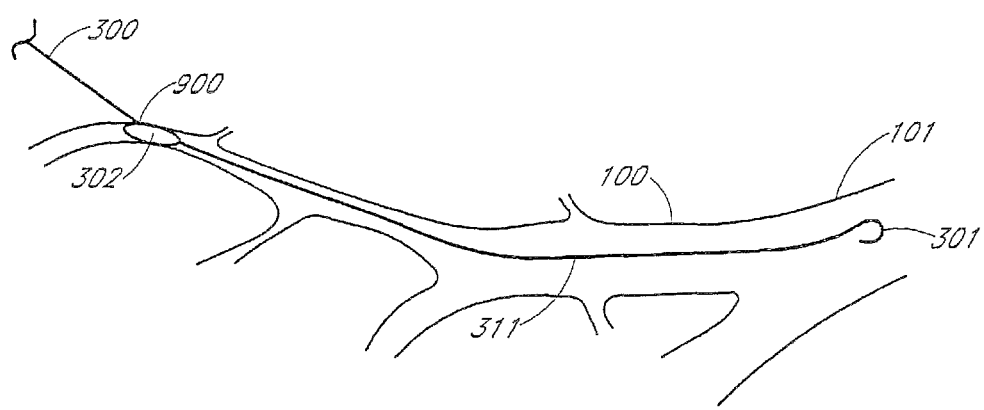
FIG. 10 is a diagrammatic illustration of a femoral artery, iliofemoral segment and aorta portion, illustrating the relative length of a portion of a guide wire device, with the device in position across an iliofemoral segment, according to one embodiment.

Referring now to FIG. 10, in certain clinical scenarios, it is necessary to provide occlusion at the level of the femoral arteriotomy 900, for example with an inflatable occlusion balloon 302 of a guide wire balloon device 300, while maintaining position of the distal tip 301 of the device 300 in the aorta 101. It is therefore desirable for the distal end 311 of the device 300 to be of sufficient length to extend through the iliofemoral 100 segment and be safely positioned (during femoral occlusion) in the aorta 101, as shown in FIG. 10. In one embodiment of the guide wire device 300, the outer diameter of the device 300 may be between about 0.014 and about 0.038 inches. In one embodiment, the length of the distal tip 311 of the device 300 may be between about 20 cm and about 50 cm. Optionally, the distal tip 311 may include a J-tip 301, as shown, and/or other features (not shown) beyond the balloon 302, similar to conventional guide wires, if desired.

Figure 11:
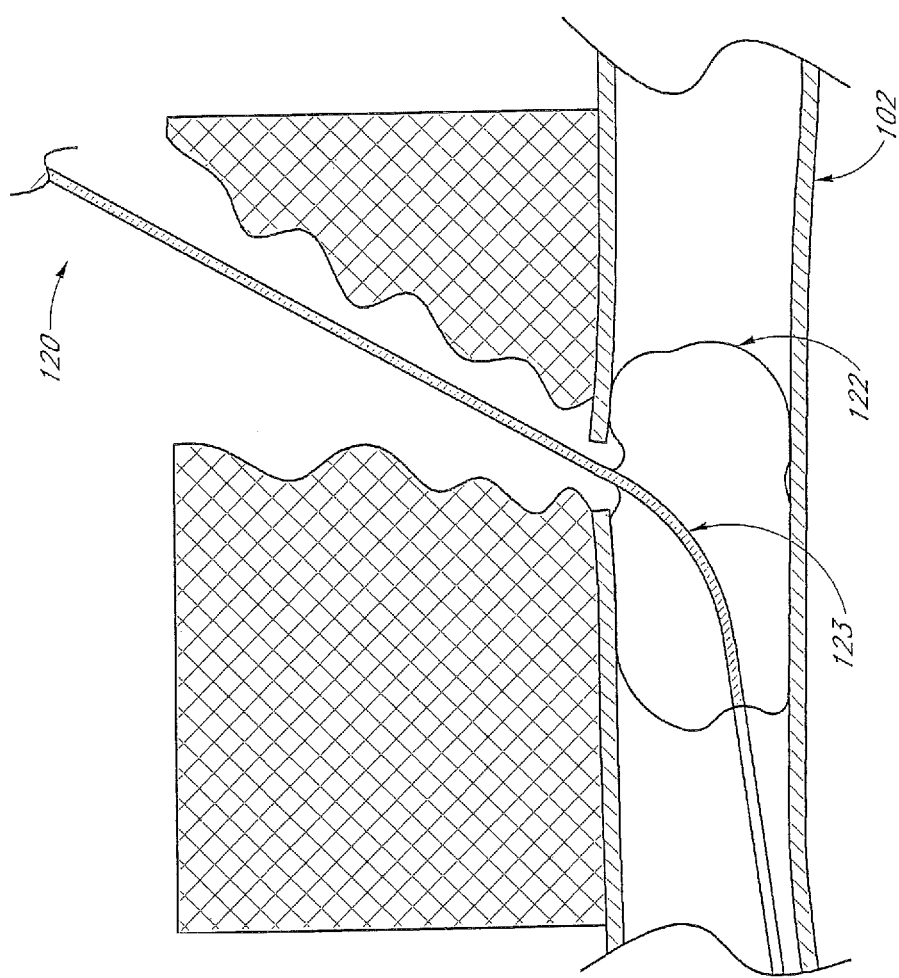
FIG. 11 is a diagrammatic illustration of a femoral artery access site and a side view of a portion of a guide wire device passed through an access site in the artery, where the guide wire device has a flexible distal end, extending across a nonlinear path at the vascular access site, according to one embodiment.

As shown in FIG. 11, in certain embodiments, a distal portion and/or balloon portion 123 of the guide wire device 120 may be capable of bending at sites of procedural bends such as the site of percutaneous catheter insertion. The embodiment shown in FIG. 11 may have a similar "flexibility profile" to those shown in FIGS. 9A-9E, where the portion of the device 120 between the proximal and distal ends of the balloon 122 is more flexible than the shaft of the device 120 immediately proximal and immediately distal to the balloon.

Figure 12:
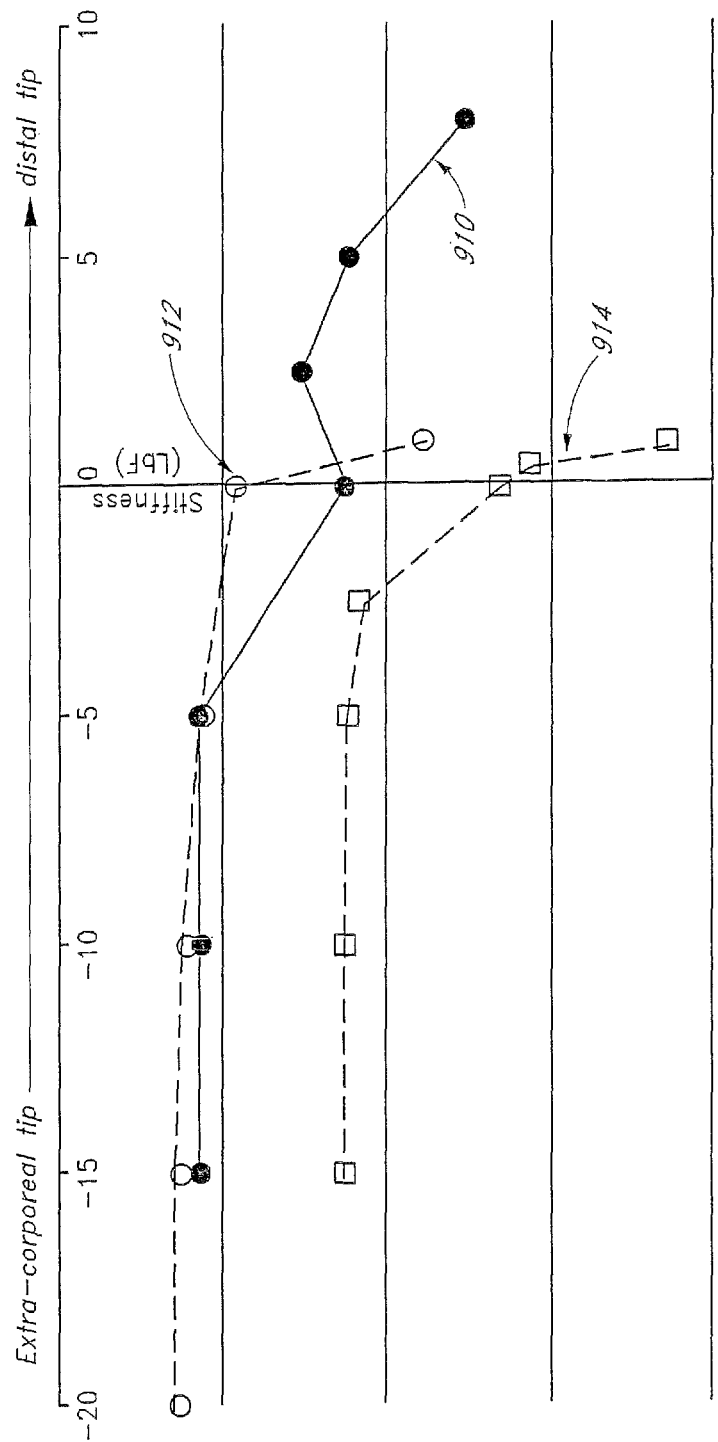
FIG. 12 is a chart illustrating experimental results comparing the stiffness characteristics of a guide wire device according to one embodiment with existing products.

Referring now to FIG. 11, several catheter characteristics such as pushability, trackability, and adaptability to vessel tortuosities are directly related to stiffness patterns of the catheter along its shaft. To determine the appropriate stiffness patterns for the guide wire device described herein, the following experiment was performed. The device disclosed herein was compared to the Guardwire balloon system (Medtronic PercuSurge, 0.014") and the Guideright guide wire (St. Jude, 0.038"). Each device was inserted into a catheter fixture, and the region of interest was aligned with the fixture. After the Instron was calibrated with regard to push force, deflection, and position, the Instron was advanced to cause a 5 mm deflection at the region of interest. Deflection force (LbF, N) and position of deflection (distance from inflatable segment) were recorded. The procedure was then repeated for each additional region of interest. The experimental results are illustrated in FIG. 12, where the solid line 910 represents the flexibility profile of the exemplary embodiment of the device 120 described herein, the dashed line 912 represents the profile of the Guardwire device, and the dashed line 914 represents the profile of the Guideright device.

Two catheters, the guide wire device disclosed herein and Guardwire, showed comparable stiffness profiles at the distal tip. The guide wire device, however, showed a different stiffness profile marked by the segmental decrease in stiffness at the balloon segment (position 0) relative to the proximal catheter shaft and the distal tip. This functionality lends a special flexibility feature to the balloon and allows for balloon occlusion at sites of significant tortuosity (where complications are expected), and/or at sites of procedure induced bends (such as transitions from tissue tract into arteriotomy).

Figure 13:
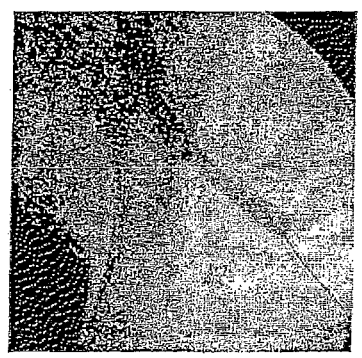
FIG. 13 shows an angiogram of a guide wire device according to one embodiment, illustrating the device's ability to occlude blood flow in a blood vessel.
Figures 14A, 14B:
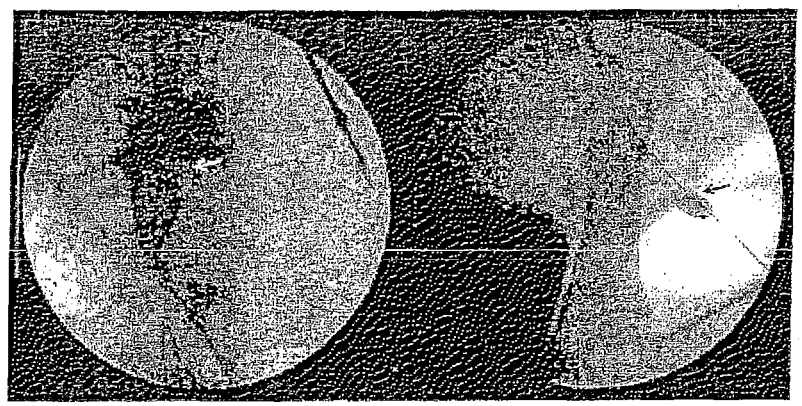
FIGS. 14A and 14B show angiographic images of the guide wire device of FIG. 13 extending from an iliofemoral segment to an aorta.

Referring now to FIGS. 13, 14A and 14B, the utility of the guide wire device was successfully tested in the sheep and showed that the intended design of decreased stiffness at the balloon segment allowed for balloon occlusion at sites of significant tortuosity (where complications are expected), and/or at sites of procedure induced bends (such as transitions from tissue tract into arteriotomy). FIG. 13 shows an angiogram of the sheep femoral artery at the site of 18Fr arteriotomy, showing the guide wire device's ability to occlude blood (contrast) flow at the site of percutaneous catheter insertion (arteriotomy). FIG. 14B is an angiographic image showing a clinical scenario where an occlusion at the femoral arteriotomy is required. In this scenario, as shown in FIG. 14A, it would be desirable for the J-tip of the distal tip to be of sufficient length to extend through the iliofemoral segment and be safely positioned (during femoral occlusion) in the aorta.

Figure 15:
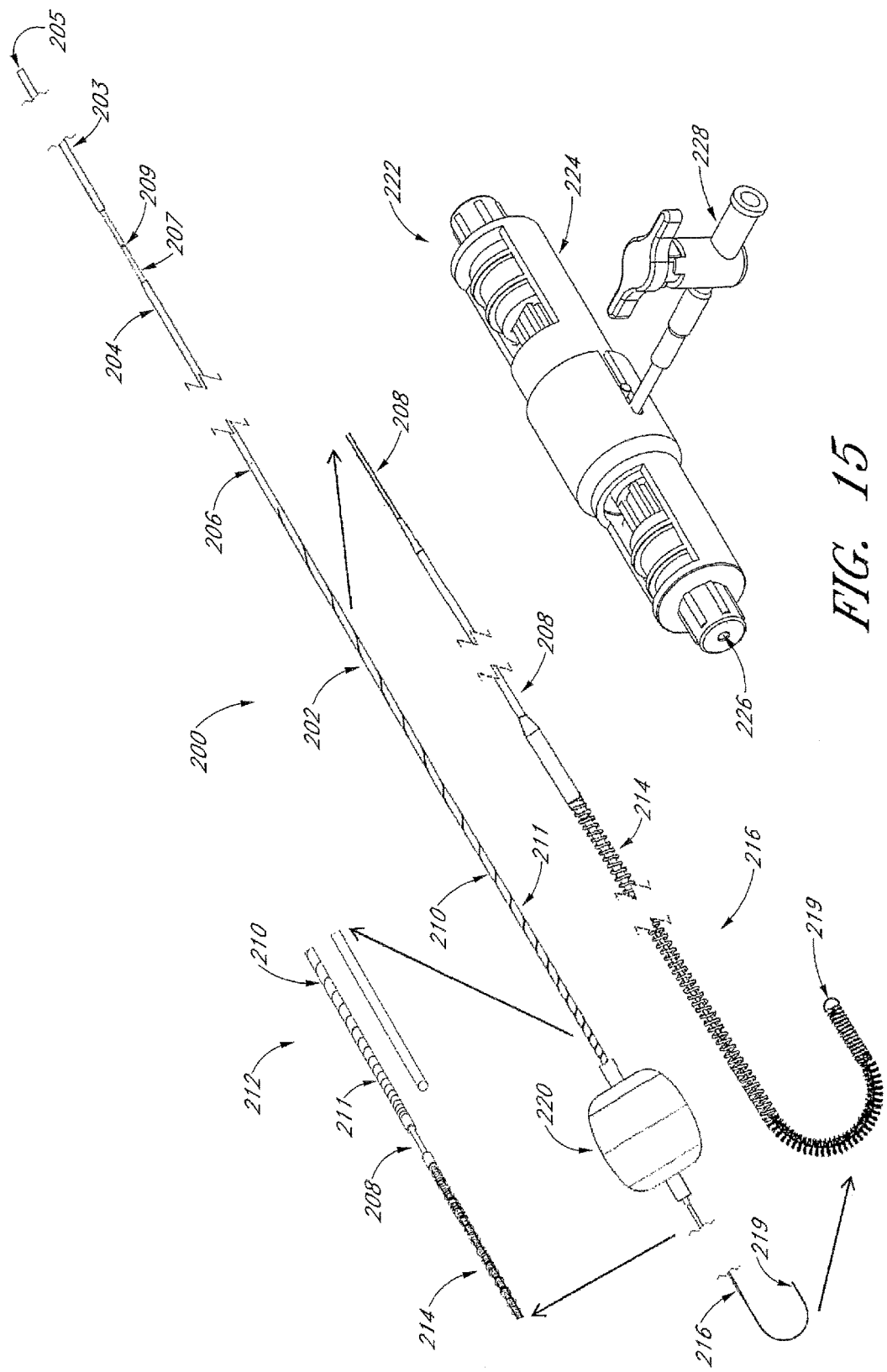
FIG. 15 is a perspective view of a guide wire balloon system, including close-up views of an inflation device, a balloon section of a guide wire device, and a core wire and distal tip of the guide wire device, according to one embodiment.

Referring now to FIG. 15, in another embodiment, a guide wire balloon system 200 (or "guide wire system") for providing blood vessel occlusion, blood vessel injury stabilization and/or a device along which one or more treatment devices may be introduced during or after a large bore or other intravascular procedure may include a guide wire device 202 (or "guide wire balloon device") and an inflation device 222. Optionally, the system 200 may also include an inflation medium container/injection device (not shown), such as but not limited to a syringe, a pump or the like. The guide wire device 202 extends from a hubless proximal end 205 to a distal end 219 and includes an expandable member such as an inflatable balloon 220 closer to the distal end 219 than the proximal end 205. The guide wire device 202 may be described as having a valve portion 204 (or "proximal portion"), a middle portion 210, a balloon portion 212 (or "transition portion", "transition section" or "transition zone") and a flexible tip 216 (or "J-tip," "distal tip" or "distal portion"). These designations of the various portions of the guide wire device 202 are made for descriptive purposes only and do not necessarily connote specific demarcations or mechanical differences between the various portions, although in some embodiments, the various portions may have one or more unique characteristics.

The guide wire device 202 may further include a shaft 206 that extends from the valve portion 204 of the guide wire device 202 to at least a proximal end of the balloon 220. In one embodiment, the shaft 206 may be a hypotube, made of Nitinol, stainless steel, or some other metal, and may include a spiral cut 211 along part of its length to increase flexibility, as will be described in greater detail below. Inside the shaft 206, within the valve portion 204, there may reside an inflation hypotube 207 (or "inner tube") with an inflation port 209, through which inflation fluid may be introduced. A valve cap 203 may be slidably disposed over the proximal end of the inflation hypotube 207, such that it may be moved proximally and distally to close and open, respectively, the inflation port 209. As best seen in the bottom magnified view of FIG. 15, a core wire 208 may be disposed within the shaft 206 along at least part of the middle portion 210 and may extend through the balloon portion 212 and in some embodiments through at least part of the distal tip portion 216. A coil 214 may be wrapped around part of the core wire 208 and may also extend beyond the core wire 208 to the extreme distal end 219. Various aspects and features of the shaft 206, inflation hypotube 207, core wire 208, coil 214, etc. will be described in further detail below.

The inflation device 222, which is also described in more detail below, may generally include a handle 224, a wire lumen 226 for inserting the guide wire device 202, and a locking inflation port 228. The handle 224 may be movable from a first position in which the guide wire device 202 may be inserted into the lumen 226 to a second position in which the handle 224 locks onto the shaft 206 and the valve cap 203. The handle may also be moveable from a valve-open position, in which inflation fluid may be passed into the inflation port 209 of the guide wire device 202, to a valve-closed position, in which the inflation fluid is trapped inside the balloon 220 and guide wire device 202. These positions and other aspects of a method for using the inflation device 222 will be described further below.

In one embodiment, the guide wire device 202 may have varying amounts of stiffness along its length, typically being stiffest at the proximal end 205 and most flexible at the distal end 219. The proximal/valve portion 204 and a proximal portion of the middle portion 210 of the guide wire device 202 are typically the stiffest portions of the device and will have sufficient stiffness to allow the device 202 to be advanced through a sheath and into a blood vessel, typically against the direction of blood flow (i.e., retrograde advancement). Along the middle portion 210, the device 202 may be relatively stiff at a most proximal end and quite flexible at a distal end (within, or adjacent the proximal end of, the balloon 220). This change in stiffness/flexibility may be achieved using any of a number of suitable mechanical means. In the embodiment shown, for example, the shaft 206 includes a spiral cut 211 along its length, where the spacing between the cuts becomes gradually less along the middle portion 210 from proximal to distal. In other words, the "threads" of the spiral cut are closer together distally. In alternative embodiments, increasing flexibility of the shaft 206 from proximal to distal may be achieved by other means, such gradually thinning the wall thickness of the shaft, using different materials along the length of the shaft or the like.

In the embodiment of FIG. 15, the spiral cut 211 may be configured such that the shaft 206 has a relatively constant stiffness along a the valve portion 204 and a proximal part of the middle portion 210. As the shaft 206 approaches the proximal end of the balloon 220, the stiffness may fall off abruptly. In other words, the stiff shaft 206 has a significant drop-off in stiffness immediately proximal to the balloon 220. This type of stiffness/flexibility profile is in direct contrast to the typical prior art balloon catheter, which simply becomes more flexible at a gradual, consistent rate over its length. The unique stiffness profile of the guide wire device 202 may be advantageous, because maintaining significant stiffness along most of a proximal length of the device 202 provides for enhanced pushability against blood flow, while a significantly more flexible portion immediately proximal to, within, and distal to the balloon 220 will help to prevent injury to the vessel through which the device 202 is being advanced. A stiffer proximal portion 204 and middle portion 210 may also help temporarily straighten out a tortuous blood vessel, which may facilitate stabilizing and/or treating an injury in the vessel.

The top portion of FIG. 15 is a close up of the balloon section 212 of the guide wire device 202, with the balloon 220 removed. In this embodiment, the shaft 206 extends into a portion of the balloon section 212, with the spiral cut getting tighter, and then ends, leaving a small portion of the core wire 208 exposed. Inflation fluid exits from the distal end of the shaft 206 to inflate the balloon 220. The shaft 206 thus forms an inflation lumen (not visible in FIG. 15), and in the embodiment with the spiral cut 211, a coating or sleeve may be used to seal the shaft 206 to prevent inflation fluid from escaping the shaft 206 through the spiral cut 211. For example, a polymeric coating may be used, such as a shrink wrap coating, sprayed-on coating, dip coating, or the like. In alternative embodiments, the shaft 206 may end at the proximal end of the balloon 206 or may continue through the entire length of the balloon 220 and include one or more inflation ports in its sidewall. A distal portion of the core wire 208 is wrapped by the core wire 214. In these or other alternative embodiments, core wire 214 may stop at a distal end of the balloon 220 or alternatively extend all the way through the balloon 220. A number of various embodiments of the balloon section 212 will be described below in greater detail.

Referring now to the bottom close-up of FIG. 15, the core wire 208 may, in some embodiments, have a varying diameter at one or more points along its length. In alternative embodiments, it may have a continuous diameter. In the embodiment shown, for example, the core wire 208 has a relatively small diameter proximally, widens to a wider diameter, widens again to a widest diameter, and contracts gradually to a smallest diameter the flexible, J-tip portion 216. As will be described in greater detail below, the proximal end of the core wire 208 (not visible in FIG. 15) may also be widened, flattened or otherwise shaped to facilitate attaching the proximal end to an inner wall of the shaft 206 via gluing, welding, soldering or the like. The widest diameter section of the core wire 208, in this embodiment, is located where the distal end of the balloon 220 is mounted onto the core wire 208. This widest portion thus helps provide strength at an area of stress of the device 202. In some embodiments, the proximal end of the core wire 208 is attached to an inner surface of the shaft 206 by any suitable means, such as by welding, soldering, gluing or the like. In some embodiments, the attachment point of the core wire 208 to the shaft 206 is proximal to the area along the shaft 206 where the spiral cut 211 begins. Alternatively, the core wire 208 may be attached at any other suitable location.

As illustrated in the bottom close-up of FIG. 15, in one embodiment, the diameter of the core wire 208 gets smaller and smaller distally along the length of the flexible J-tip portion 216, thus forming the most flexible, J-curved, distal portion of the guide wire device 202. In alternative embodiments, the core wire 208 may end proximal to the extreme distal end 219 of the guide wire device 202, and the coil 214 may continue to the distal end 219. In other alternative embodiments, the distal tip 216 may be straight, may include two core wires 208, may include more than two core wires 208, may be straightenable and/or the like. In the embodiment shown, the core wire includes a flat portion through the curve of the J-shape of the tip 216 and is attached to the coil 214 at the distal end 219 via a weld (or "weld ball"). The distal, curved portion of the J-tip is designed to be atraumatic to blood vessels through which it is advanced, due to its flexibility and shape.

The distal J-tip 216 of the guide wire device 202 may include special properties and/or features allowing for retrograde (against blood flow) insertion, maneuvering, and/or placement. For example, the "J-tip" shape of the distal tip 216 allows it to be advanced against blood flow without accidentally advancing into and damaging an arterial wall.

Additionally, the distal tip 216 has a proximal portion through which the core wire 208 extends and a distal portion that is more flexible and includes only the coil 214. This provides for a slightly stiffer (though still relatively flexible) proximal portion of distal tip 216 and a more flexible (or "floppy") distal portion of distal tip 216, thus providing sufficient pushability while remaining atraumatic. The extreme distal end 219 may also have a blunt, atraumatic configuration, as shown. In various embodiments, the distal tip 216 may also include a tip configuration, flexibility, radiopacity, rail support, core material, coating, and/or extension characteristics that enhance its function. Alternatively or in addition, device length considerations and/or overall shaft stiffness may be modified accordingly.

The core wire 208, the shaft 206 and the coil 214 may be made of any of a number of suitable materials, including but not limited to stainless steel, Nitinol, other metals and/or polymers. Each of these components may also have any suitable size and dimensions. For example, in one embodiment, the shaft 206 has an outer diameter of approximately 0.035 inches (approximately 0.9 mm). The guide wire device 202 may also have any suitable overall length as well as lengths of its various parts. Generally, the distal tip 216 will have a length that allows it to extend into an aorta when the balloon is inflated anywhere within an iliofemoral artery. In other words, the distal tip 216 may be at least approximately as long as the average iliofemoral artery. In various embodiments, for example, the distal tip 216 (measured from the distal end 219 of the device 202 to a distal end of the balloon 220) may be at least about 15 cm long, and more preferably at least about 20 cm long, and even more preferably between about 20 cm and about 25 cm long, or in one embodiment about 23 cm long. In various embodiments, the balloon section 212 of the device 202 may have a length of between about 10 mm and about 15 mm, or in one embodiment about 12 mm. In various embodiment, the middle section 210 of the device 202 may have a length of between about 70 cm and about 90 cm, and more preferably between about 75 cm and about 85 cm, or in one embodiment about 80 cm. And finally, in some embodiments, the valve section 204 may have a length of between about 10 cm and about 3 mm, or in one embodiment about 5 cm. Therefore, in some embodiments, the overall length of the device 202 might be between about 85 cm and about 125 cm, and more preferably between about 95 and about 115 cm, and even more preferably between about 105 cm and about 110 cm. Of course, other lengths for the various sections and for the device 202 overall are possible. For example, in some embodiments, the distal tip 216 may be longer than 25 cm, and in various embodiments, the overall length of the guide wire device 202 may range from may be longer than 115 cm. It may be advantageous, however, for ease of use and handling, to give the guide wire device 202 an overall length that is shorter than most currently available catheter devices. For an ipsilateral approach, the device 202 should generally have a length such that it is possible for the proximal portion 204 to extend at least partially out of the patient with the balloon 220 positioned within the iliofemoral artery and the distal end 219 residing in the aorta.

The balloon 220 of the guide wire balloon device 202 is generally a compliant balloon made of any suitable polymeric material, such as polyethylene terephthalate (PET), nylon, polytetrafluoroethylene (PTFE) or the like. The balloon 220 may be inflatable to any suitable diameter outside and inside the body. In one embodiment, for example, the balloon 220 may be inflatable within a blood vessel to a diameter of between about 6 mm and about 12 mm. In alternative embodiments, the balloon 220 may be semi-compliant or noncompliant. In some embodiments, the balloon 220 and/or portions of the device 202 immediately proximal and distal to the balloon 220 may include one or more radiopaque markers, to facilitate visualization of the balloon outside a patient's body using radiographic imaging techniques and thus facilitate placement of the balloon 220 in a desired location. The balloon 220 may be inflated, according to various embodiments, by any suitable inflation fluid, such as but not limited to saline, contrast solution, water and air.

Figure 16:
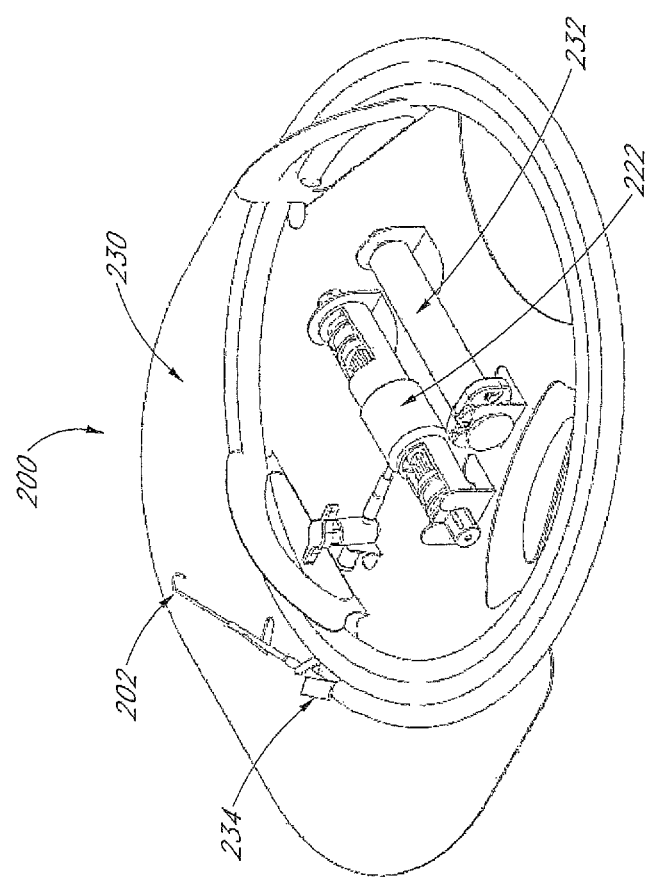
FIG. 16 is a perspective view of the system of FIG. 15 partially packaged in a kit with other components, according to one embodiment.

With reference now to FIG. 16, the guide wire balloon system 200 is shown in kit form, with one embodiment of a packaging component. The guide wire device 202 and inflation device 222 are shown, along with a guide wire balloon packaging card 230, a syringe 232 (for example 10 mL syringe with clips) for inflating the balloon 220, and a guide wire balloon sheath valve introducer 234. The sheath valve introducer 234 is generally a funnel-shaped device for facilitating introduction of the J-tip 216 into a vascular sheath through which the device 202 is to be introduced. In various embodiments, the system 200 or kit may include fewer or more components.

Figure 17D:
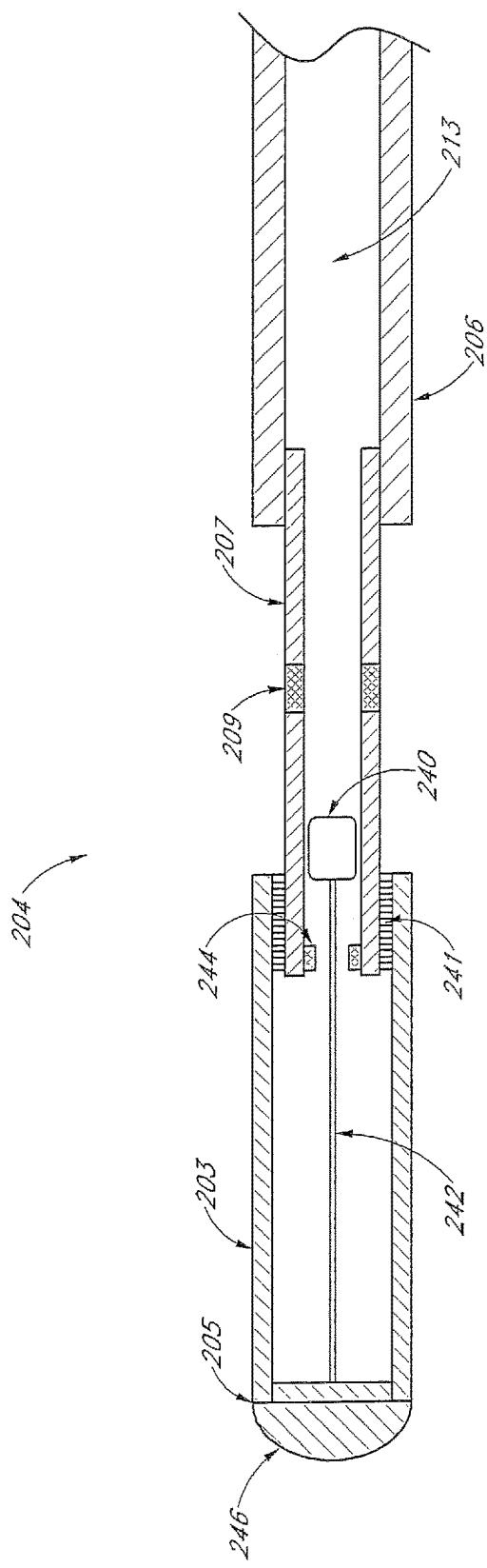
Figure 18:
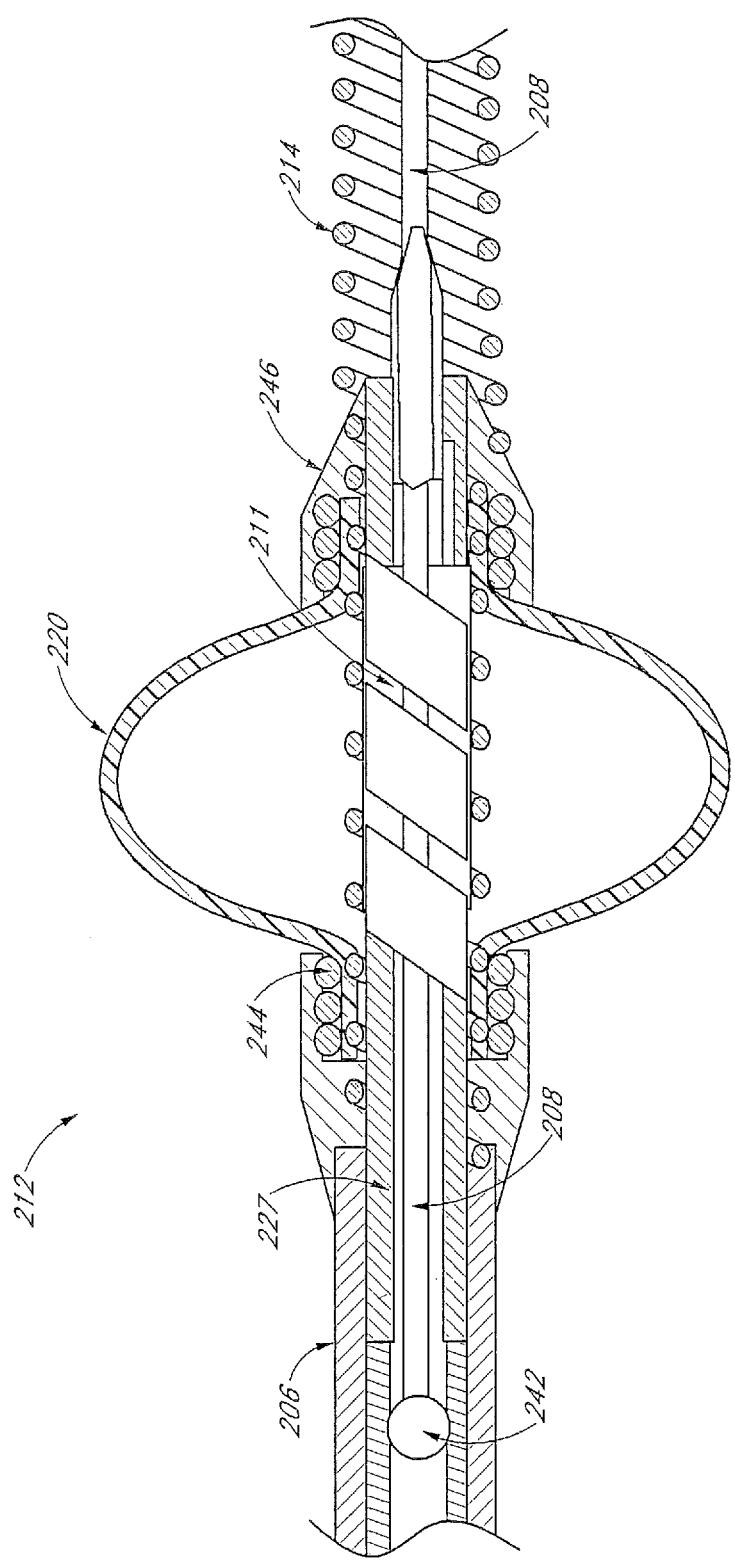

Referring now to FIGS. 17A-17D, further details of the guide wire device 202 are shown. FIG. 17A shows the entire length of the guide wire device 202, though it may not be drawn to scale. FIG. 17B shows a close-up view of the J-tip portion 216, including the core wire 208, coil 214 and distal end 219. For simplicity, the core wire 208 is shown as transitioning from a larger diameter proximally to a smaller, constant diameter distally. Alternatively, however, the core wire 208 may transition to a gradually smaller and smaller diameter distally.

FIGS. 17C and 17D show the inner workings of one embodiment of the valve portion 204. As mentioned previously, in at least some embodiments, the proximal end 205 and valve/proximal portion 204 of the guide wire device 202 are hubless, meaning that no hub or other obstruction is located on these portions to interfere with the advancement of one or more additional devices over the proximal end 205. The inflation device 222 is, of course, attached to inflate or deflate the balloon 220, but once the balloon 220 is inflated, the inflation device 222 may be removed, leaving the balloon 220 inflated and the proximal end 205 (located outside the patient's body) free for advancement of one or more additional devices.

In the embodiment shown, the valve portion 204 includes a proximal portion of the shaft 206, which forms an inflation lumen 213, and the valve cap 203, which is slidably disposed over the inflation hypotube 207 and abuts the proximal end of the shaft 206. In this embodiment, the valve cap 203 has a different wall thickness than that of the shaft 206. The valve cap 203 may be made of the same material as the shaft 206 or, in alternative embodiments, a different material, such as but not limited to Nitinol, stainless steel, other metals or polymers. The inflation hypotube 207, which is fixedly attached to an inner surface of the proximal end of the shaft 206, may also be made of Nitinol, stainless steel or any other suitable material, and may be the same material as the shaft 206 and the valve cap 203 in one embodiment. The inflation hypotube 207 also includes the inflation port 209, as described previously. In one embodiment, a silicone ring 241 (or "coating") may be positioned on an inner surface of the valve cap 203 at or near its distal end. The silicone ring 241 may form a seal between the valve cap 203 and the inflation hypotube 207, thus preventing the escape of inflation fluid between the two.

The valve portion 204 may also include a proximal end cover 246 attached to the proximal end 205 of the valve cap 203. A post 242 (or "wire") may be attached to the proximal end cover 246, and a flow regulator 240 may be attached to the post 242. Finally, the valve portion 204 may also include a stop member 244 on an inside surface of the inflation hypotube 207 at or near its proximal end. The stop member 244 may stop the flow regulator 240 from being drawn too far proximally and thus being pulled out of the inflation hypotube 207.

These components of the valve portion 204 effectively form a two-part valve, where inflation fluid is blocked from escaping externally by the valve cap 203 and is blocked internally by the flow regulator 240. The valve portion 204 may work as follows. Referring to FIG. 17C, to close the valve, the valve cap 203 is advanced distally to cover the inflation port 209 and abut the proximal end of the shaft 206. In this valve-closed configuration, the flow regulator 240 is positioned distal to the inflation port 209, thus blocking inflation fluid from entering the inflation hypotube 207 from the inflation lumen 213. Thus, again, inflation fluid is prevented from entering or exiting the inflation lumen 213 by the flow regulator 240 and the valve cap 203.

Referring now to FIG. 17D, to open the valve, the valve cap 203 may be moved proximally to expose the inflation port 209 and to move the flow regulator 240 proximal to the inflation port 209. At this point, with the valve portion 204 in the valve-open position, the inflation device 222 may be used to pass contrast solution, saline solution, air, water or other inflation medium through the inflation port 209 and into the inflation lumen 213 of the shaft 206 to inflate the balloon 220. When the balloon 220 is inflated, the valve cap 203 may be once again advanced distally to the valve-closed position, thus covering the inflation port 209 and blocking the inflation hypotube 207 with the flow regulator 240. If desired, the inflation device 222 may then be removed from the guide wire device 202, and one or more therapeutic devices may be passed over the hubless proximal end 205 of the device 202. In one embodiment, the inflation device 222 may be used to advance and retract the valve cap 203, as will be described further below.

Referring to FIGS. 18-25, balloon segments of various alternative embodiments of guide wire balloon devices are shown. In general, in all the embodiments described in FIGS. 18-25, various structural configurations are included to provide a desired flexibility/stiffness profile immediately proximal to the balloon, between the two ends of the balloon, and immediately distal to the balloon. In the embodiment shown in FIG. 18, for example, the balloon segment 212 includes a balloon 220, an shaft 206 proximal to the balloon 220, an extension 227 extending distally from the shaft 206 and on which the balloon 220 is mounted, a core wire 208 extending through the extension 227 and attached to the shaft 206 via an attachment member 242, and a coil 214 wrapped around the core wire 208 and a portion of the extension 227. The extension 227 fits within the distal end of the shaft 206. The balloon 220 may be mounted to the extension 227 via one or more threads 224 and epoxy 246 or other form of adhesive. The extension 227 includes a spiral cut 211, which increases its flexibility. The core wire 208 may have a varying diameter along its length, for example a widened section to close off the inner lumen of the extension 227 to prevent air or other inflation fluid from escaping distally out of the balloon 220. The proximal end of the core wire 208 may be attached to the shaft 206 by any suitable attachment member 242 or attachment means. For example, attachment member 242 may be a weld, glue, other adhesive, anchor or the like.

Figure 19:
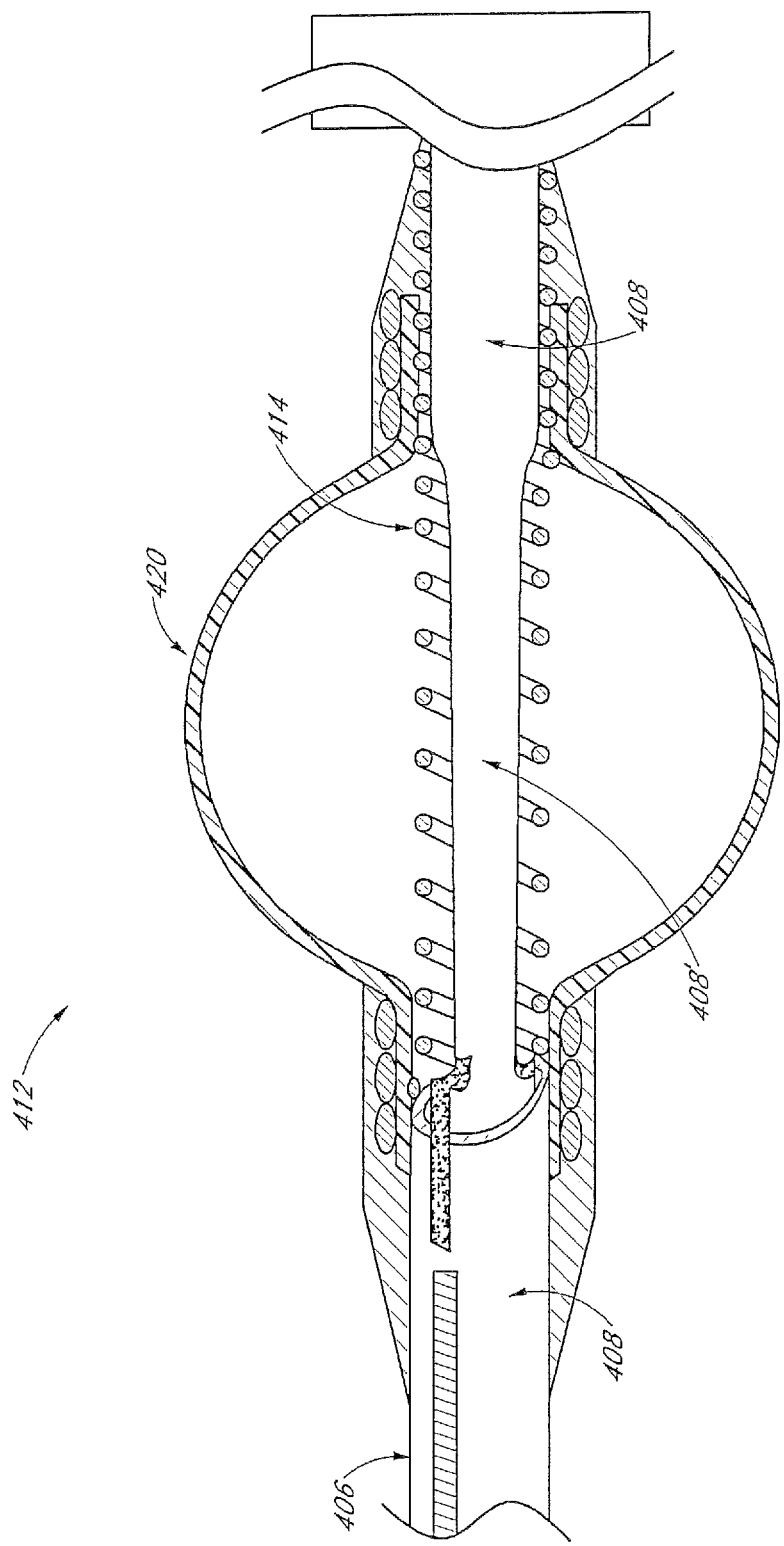

With reference to FIG. 19, in an alternative embodiment, a balloon segment 412 of a guide wire balloon device may include a balloon 420, a shaft 406, a core wire 408 with a thinner balloon section 408' and a coil 414 around at least part of the core wire 408. The shaft 406 may, for example, be a hypotube. A flattened proximal end of the core wire 408 may be attached to the shaft 406 by any suitable means, such as welding, gluing, soldering or the like. Coil 414 provides extra support to the balloon segment 412.

Figure 20:
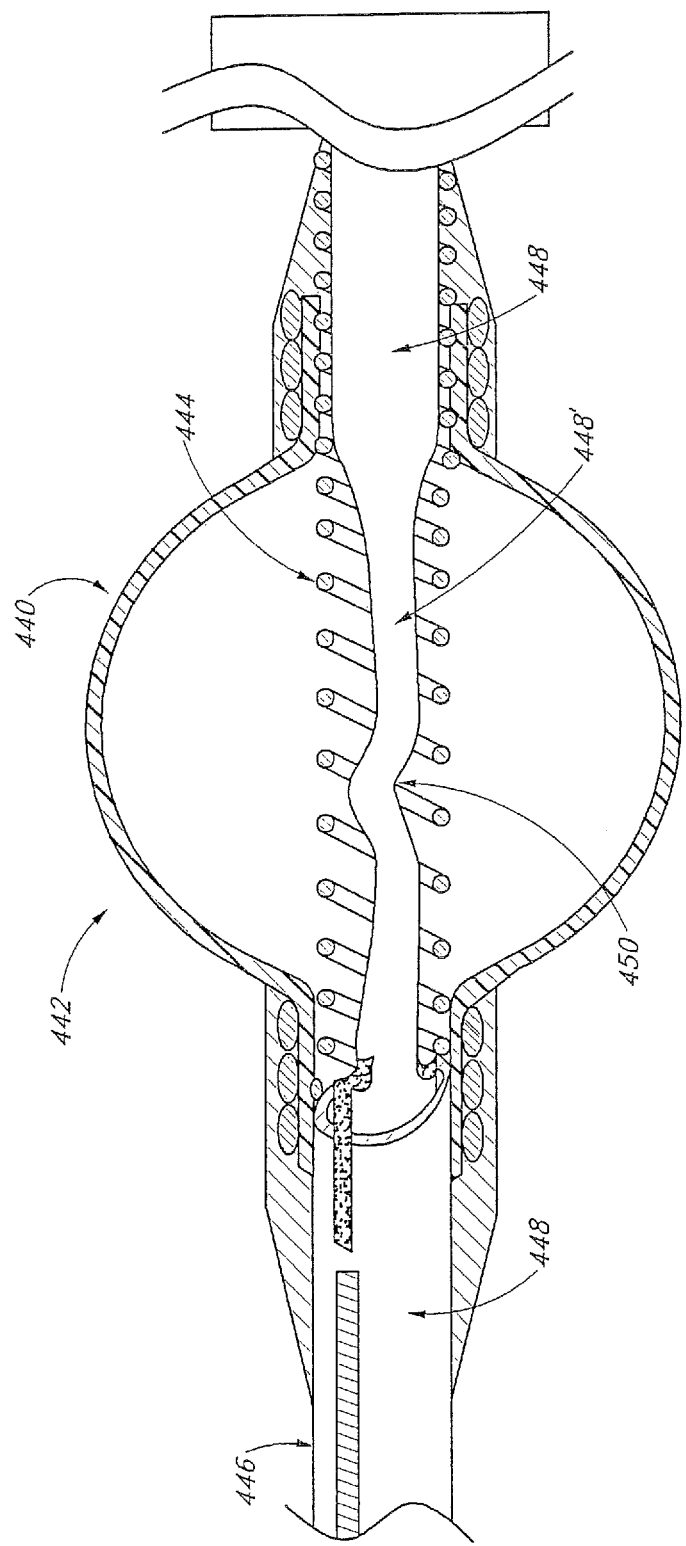

In another alternative embodiment, and with reference now to FIG. 20, a balloon segment 442 of a guide wire balloon device may include a balloon 440, a shaft 446, a core wire 448 with a thinner balloon section 448' and a coil 444 around at least part of the core wire 448. In this embodiment, the thinner balloon section 448' may include a bend 450 (or fold), which may help provide stress relief when the balloon segment 442 is bent during use. A flattened proximal end of the core wire 448 may be attached to the shaft 446 by any suitable means, such as welding, gluing, soldering or the like. Coil 444 provides extra support to the balloon segment 442.

Figure 21:
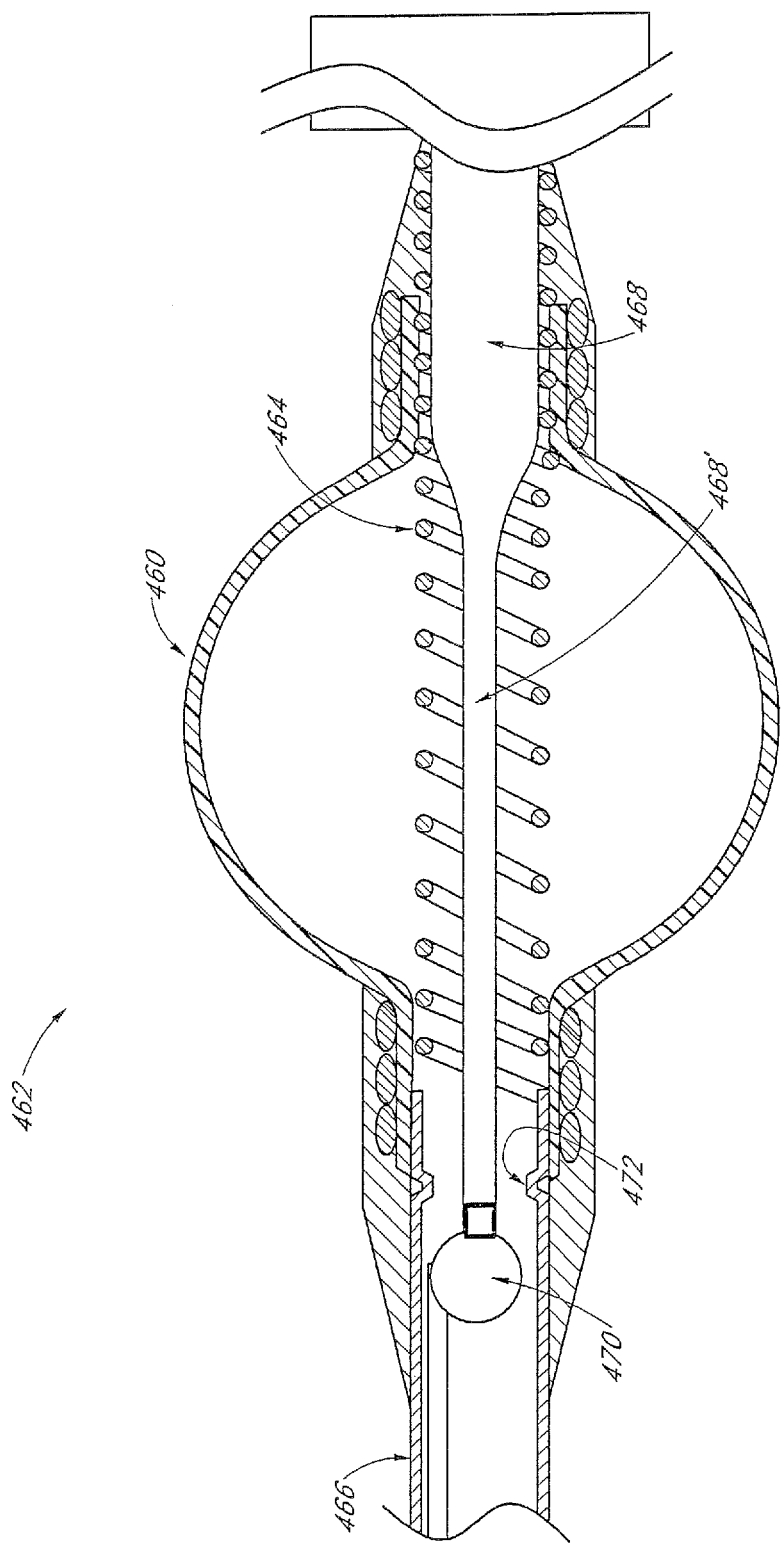

Referring to FIG. 21, in another alternative embodiment, a balloon segment 462 of a guide wire balloon device may include a balloon 460, a shaft 466, a core wire 468 with a thinner balloon section 468' and a coil 464 around at least part of the core wire 468. In this embodiment, a proximal end of the core wire 468, which may be part of the thinner balloon section 468', may include (or be attached to) a ball-shaped member 470. Shaft 466 may include an inward facing stop member 472. Together, the ball-shaped member 470 and the stop member 472 act as a joint, allowing the balloon segment to flex at the joint and thus accommodate bending during use. Coil 464 provides extra support to the balloon segment 462.

Figure 22:
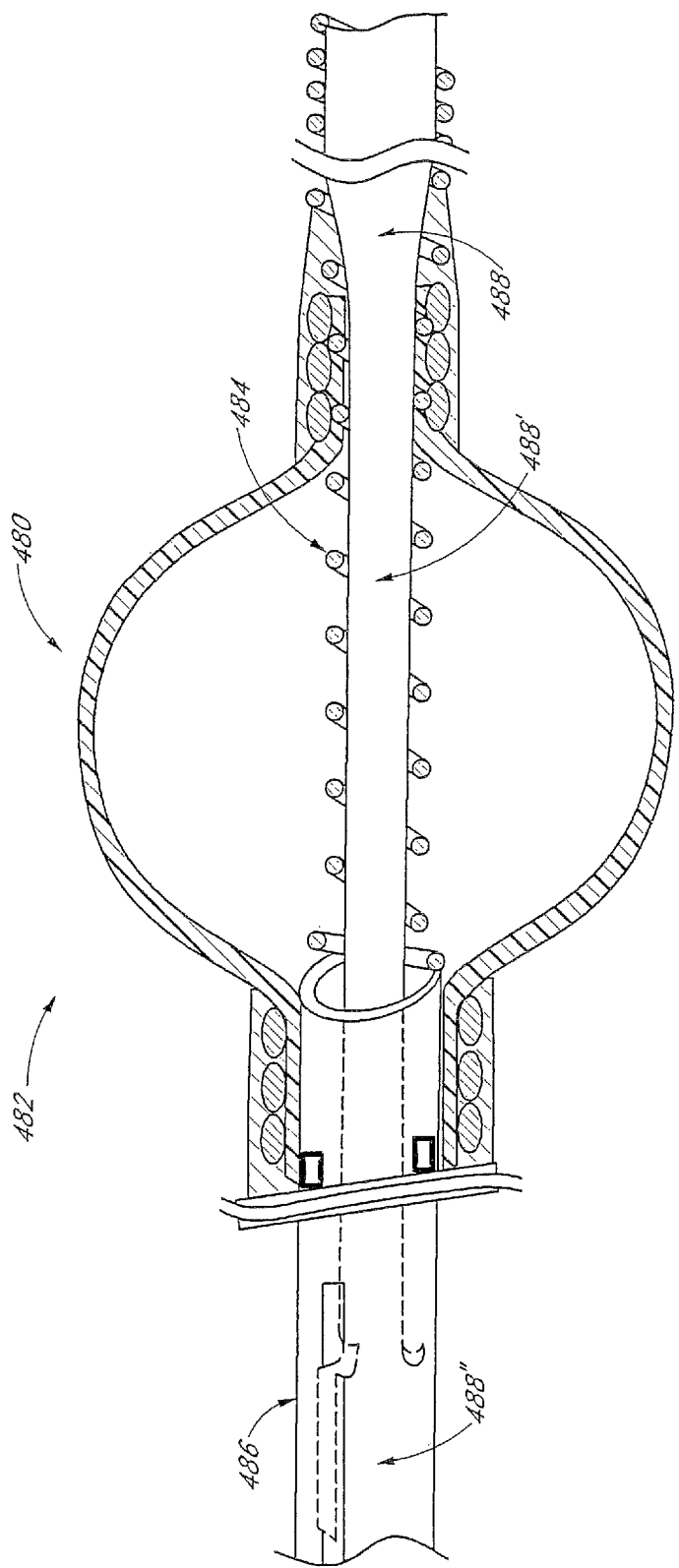

Referring to FIG. 22, in another alternative embodiment, a balloon segment 482 of a guide wire balloon device may include a balloon 480, a shaft 486, a core wire 488 with a thinner balloon section 488' and a coil 484 around at least part of the core wire 488. In this embodiment, a proximal end of the core wire 488" may be flattened to facilitate attachment to shaft 486 via welding, gluing, soldering or the like. The thinner balloon section 488' may continue up to the proximal end 488". Coil 484 provides extra support to the balloon segment 482.

Figure 23:
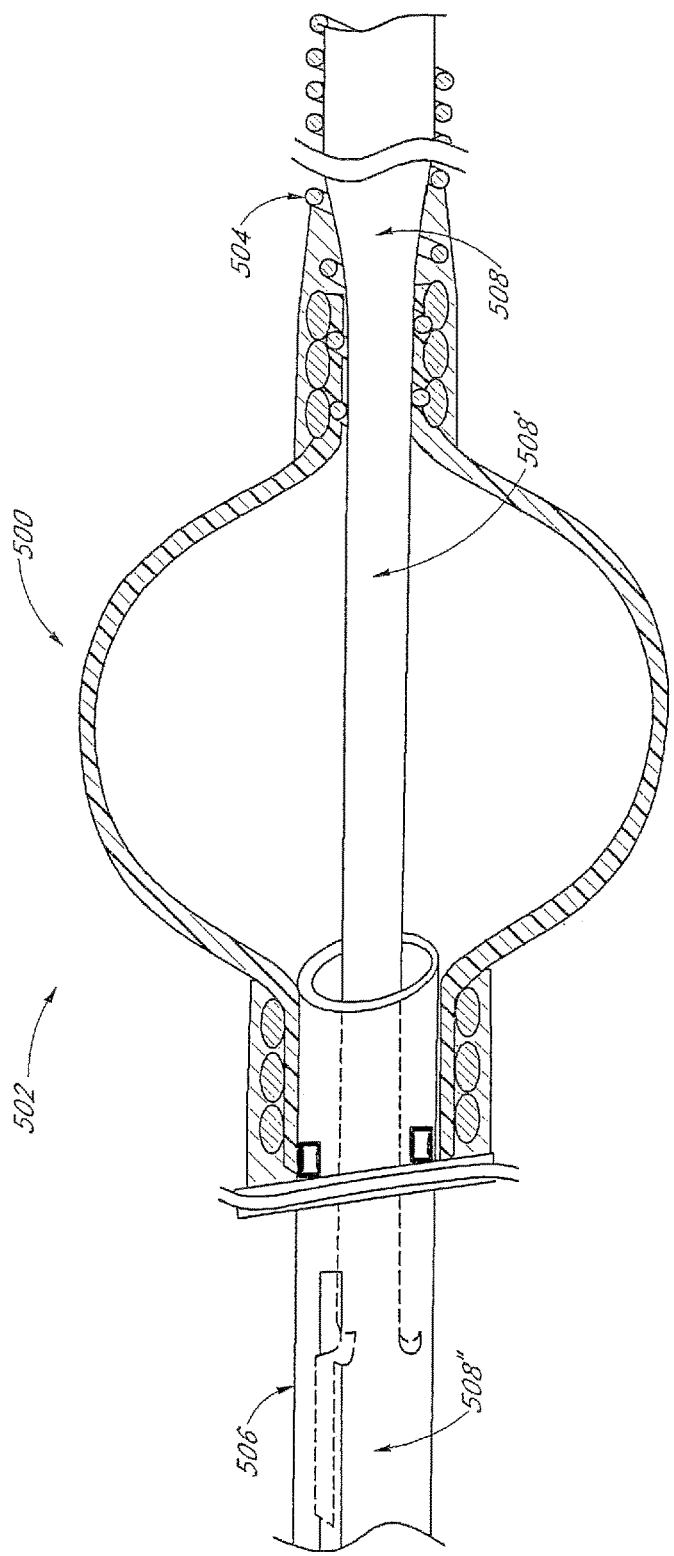

Referring to FIG. 23, in another alternative embodiment, a balloon segment 502 of a guide wire balloon device may include a balloon 500, a shaft 506, a core wire 508 with a thinner balloon section 508' and a coil 504 around at least part of the core wire 508. In this embodiment, as in the previously described embodiment, a proximal end of the core wire 508" may be flattened to facilitate attachment to shaft 506 via welding, gluing, soldering or the like. The thinner balloon section 508' may continue up to the proximal end 508". Unlike the previous embodiment, in this embodiment, the thinner balloon section 508' is not covered with the coil 504. This will make the thinner balloon section 508' more flexible than in the previously described embodiment.

Figure 24:
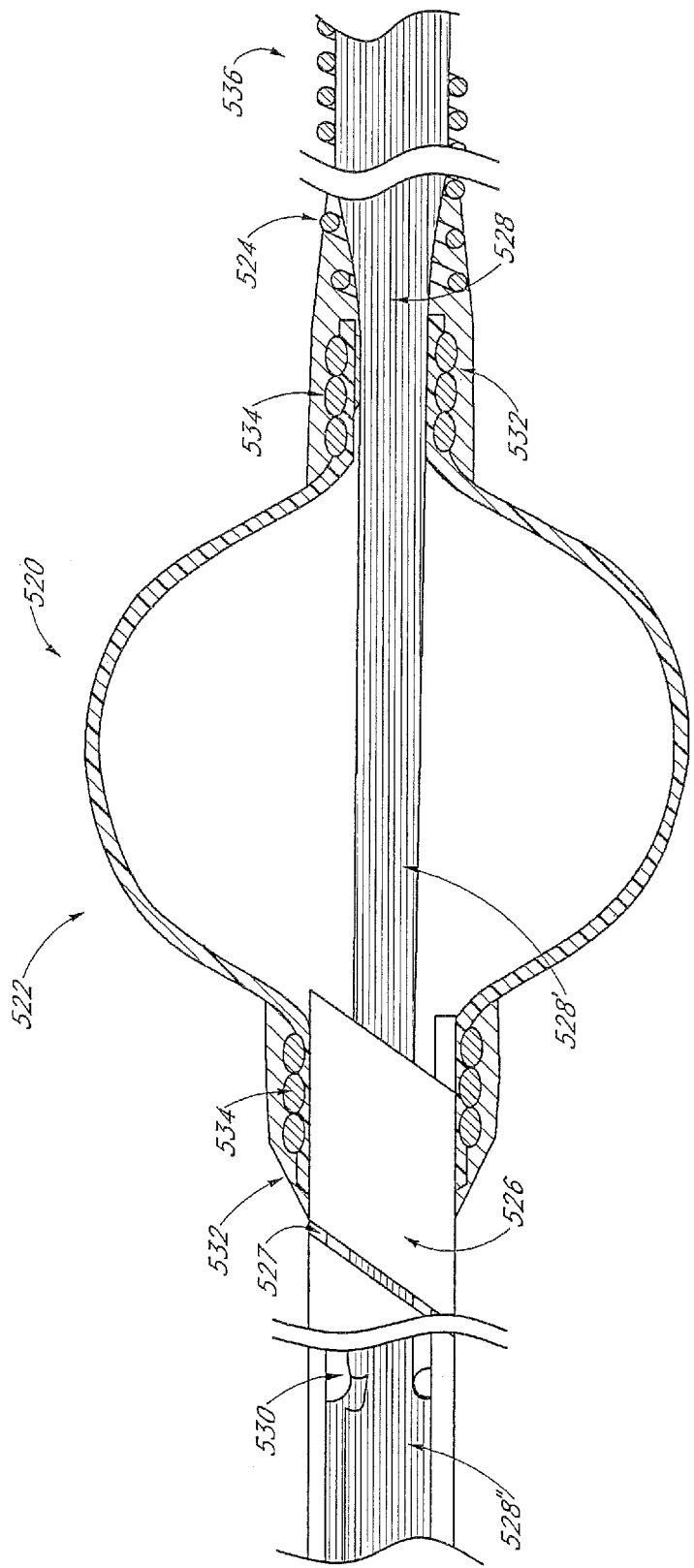

With reference now to FIG. 24, in yet another alternative embodiment, the balloon segment 522 may include a balloon 520, a shaft 526 having a spiral cut 527 along at least a portion of its length proximal to a proximal end of the balloon 520, a core wire 528 extending from the distal tip 536 and through the extension balloon segment 522 and attached to the shaft 526 proximally, and a coil 524 disposed over at least a portion of the core wire 528 distal to the balloon 520. The core wire 528 may include a thinner balloon section 528' underlying the balloon 520 and a flattened proximal end 528", which may facilitate attachment to the shaft 526 via welding, gluing, soldering or the like. As in most or all embodiments, the shaft 526 forms an inflation lumen 530 for inflating the balloon 520. Due to the spiral cut 527, the shaft 526 will typically be coated or covered with a sheath, such as a polymeric coating or sheath, to prevent inflation fluid (air, saline, etc.) from leaking through spiral cut 527. The balloon 520 may be mounted to the shaft 526 proximally and to the core wire 528 distally via threads 534 and epoxy 532 or other form of adhesive.

Referring now to FIG. 25, in another alternative embodiment, the balloon segment 542 may include a balloon 540, a shaft 546 proximal to the balloon 540, an extension tube 556 extending distally from the shaft 206 and on which the balloon 540 is mounted, a core wire 548 extending through the extension 556 and attached to the shaft 546 via welding, gluing, soldering or the like of a flattened proximal end 548" to the shaft 546, and a coil 544 wrapped around a portion of the core wire 548 distal to the balloon 540. The extension tube 556 attaches to the proximal end of the shaft 546 by fitting around its outer surface. In one embodiment, the extension tube 556 may be made of polyamide or other flexible plastic. The balloon 540 may be mounted to the extension tube 556 via one or more threads 554 and epoxy 552 or other form of adhesive. The core wire 548 may have a varying diameter along its length, such as a thinner balloon section 548' and a wider proximal end 548". The wider proximal end 548" may be attached to the shaft 546 by any suitable attachment means.

The foregoing examples of balloon sections of various embodiments of a guide wire balloon device are provided for exemplary purposes only and should not be considered as an exhaustive list or as limiting the scope of the claims of this application. Various features and elements described above may be interchanged or eliminated and/or other features may be added in alternative embodiments.

Referring now to FIGS. 26A-26F, further detail of the inflation device 222 is shown. As shown in FIG. 26A, the inflation device 222 may include one or more markings 223, for example to show which direction the parts of the device 222 may be moved to release or secure the guide wire device, to open or close the valve, etc. As shown in FIG. 26B, the inflation device 22 may suitably include a high pressure luer 250a, 250b, extension tubing 252, O-ring seal 254, a handle body main portion 256, a handle body cap 258, a flared hypotube 260, a one-way stopcock/luer 262, a handle outer shell slider 264, a handle outer shell main portion 266, an outer shell pin 268, a handle luer cap 270, and a non-vented luer cap 272. In various alternative embodiments, one or more of these components may be changed, replaced with another like component, repositioned, etc., without departing from the scope of an inflation device as described in the claims. In various embodiments, the components of the inflation device 222 may be made of one or more polymers, metals or combinations thereof. Some or all of the various components will be described in further detail below, in relation to an exemplary method for using the device 222.

FIGS. 26C-26F are top, perspective, side and end-on views of the inflation device 222, respectively, according to one embodiment. The inflation device 22 may have any of a number of suitable configurations and dimensions. For example, it may be advantageous to have an inflation device 222 that can be easily held in one hand, so a user may use his/her other hand for holding a syringe or other inflation medium carrying/injecting device coupled with the inflation device 222. The inflation device 222 may also have a size selected such that a user may grip the outer shell slider 264 with one hand and the outer shell main portion 266 with the other hand, to move the two portions 264, 266 away from and towards one another to open and close the valve of the guide wire balloon device. In some embodiments, for example, an outer diameter of the outer shell slider 264 may be between about 20 mm and about 30 mm, or more preferably between about 24 mm and about 25 mm. In some embodiments, the inflation device 222 may have an overall length from one end of the luer cap 270 to an opposite end of the non-vented luer cap 272 of between about 120 mm and about 150 mm, or more preferably between about 130 mm and about 140 mm. These and other dimensions may be different in alternative embodiments and are thus provided here for exemplary purposes only.

Figure 27A:
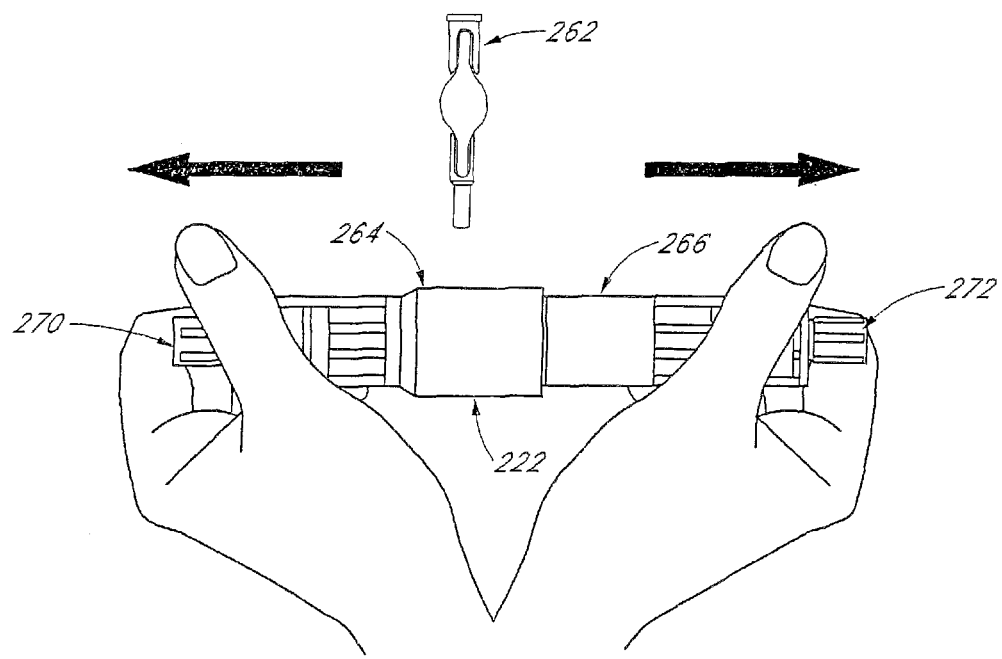
FIGS. 27A and 27B are top views of an inflation device and the hands of a user, illustrating a method for using the inflation device, according to one embodiment.
Figure 27B:
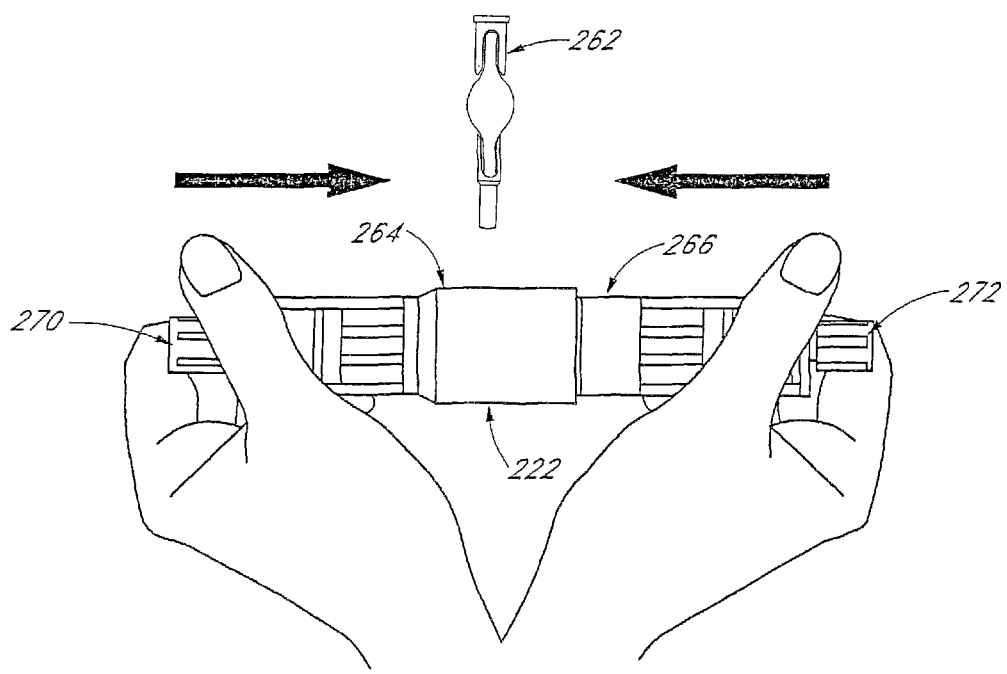

Referring now to FIGS. 27A and 27B, a method for using the inflation device 222, according to one embodiment, will be described. First, the proximal end of a guide wire balloon device (not shown in these figures) may be passed into the inflation device via the wire lumen 226 on the handle luer cap 270 (inflation port 226 visible in FIG. 15). In one embodiment, the proximal end of the guide wire device may be advanced into the inflation device 222 until it contacts a stop. To lock the inflation device 222 onto the guide wire device, the two slide members 250a, 250b that make up the high pressure luer 250a, 250b may be moved towards one another within the outer shell slider 264 and the outer shell main portion 266, as designated by the words "SECURE" and the accompanying arrows marked on the outer shell slider 264 and the outer shell main portion 266. Next, as in FIG. 27A, the outer shell slider 264 and outer shell main portion 266 may be moved apart from one another to open the valve of the guide wire balloon device (i.e., to expose the inflation port 209 shown in FIGS. 15, 17C and 17D). This may optionally be designated, for example, by markings 223, such as the "VALVE OPEN" marking and arrows shown in FIG. 26A. At this point (or, alternatively, at any time before this point), an inflation medium carrying and injection device, such as but not limited to a syringe, pump or the like, may be attached to the stopcock/luer 262, and inflation medium may be introduced into the guide wire to inflate the balloon. In some embodiments, for example, approximately 2-3 mL of diluted contrast solution (e.g., about 50% contrast and about 50% saline) may be used to inflate the balloon. In other embodiments, more or less fluid and/or some other fluid may be used, such as saline, undiluted contrast, water, air or the like.

Next, as illustrated in FIG. 27B, once the balloon of the guide wire device (or other expandable member) is inflated, the outer shell slider 264 and outer shell main portion 266 may be moved toward one another to close the valve of the guide wire balloon device, thus locking the inflation medium inside the balloon so that it maintains its inflated configuration. The slide members 250a, 250b of the high pressure luer 250a, 250b may next be moved away from one another to unlock the inflation device 222 from the guide wire device, and the inflation device 222 may then be removed from the guide wire device. At this point, the guide wire device has its balloon (or other expandable member) locked in the expanded/inflated configuration and has a hubless proximal end, over which one or more additional devices (such as vessel treatment devices) may be passed.

Once a vascular repair procedure is complete, or whenever the user wants to deflate the balloon of the guide wire device, the user may reattach the inflation device 222 to the guide wire device and repeat the steps outlined above, except that the inflation fluid is withdrawn instead of injected. This process may be repeated as many times as desired, for example to reposition the balloon of a guide wire balloon device within an iliofemoral artery, aorta and/or femoral artery one or more times. Alternatively, the user can reopen the valve positioned at the proximal end of the guide wire, which allows the inflation fluid to release through the valve opening resulting in the deflation of the balloon.

Figure 28:
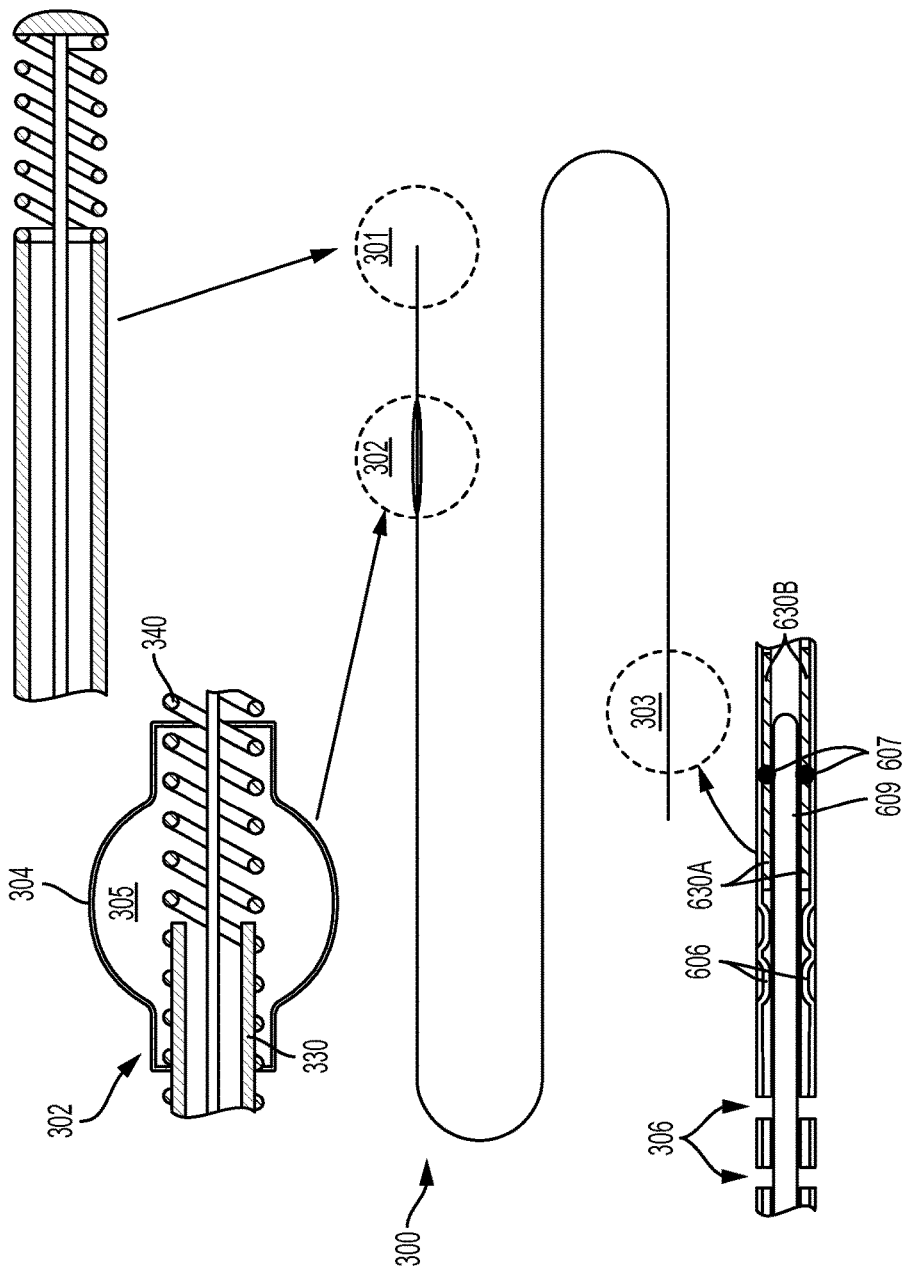
FIG. 28 is a side view of an exemplary guide wire balloon device, along with close-up, cross-sectional views of a distal tip, balloon section and valve section of the device, according to one embodiment.
Figure 29A:
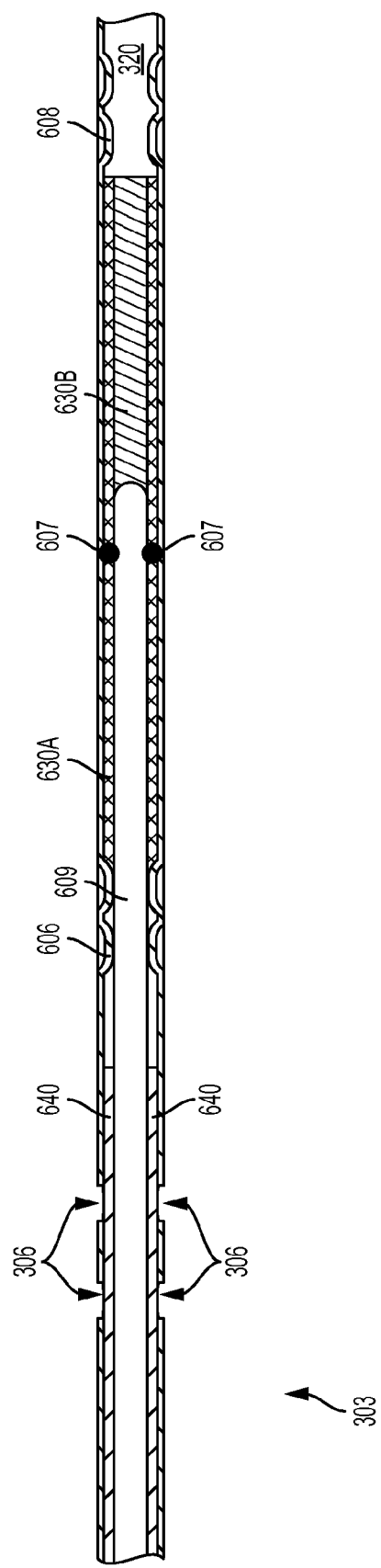
FIGS. 29A and 29B are cross-sectional side views of an alternative embodiment of a valve section (fluid regulator/valve), shown in a valve-closed configuration (FIG. 29A) and a valve-open configuration (FIG. 29B), which may be included in a guide wire device, such as the guide wire device shown in FIG. 28.
Figure 29B:
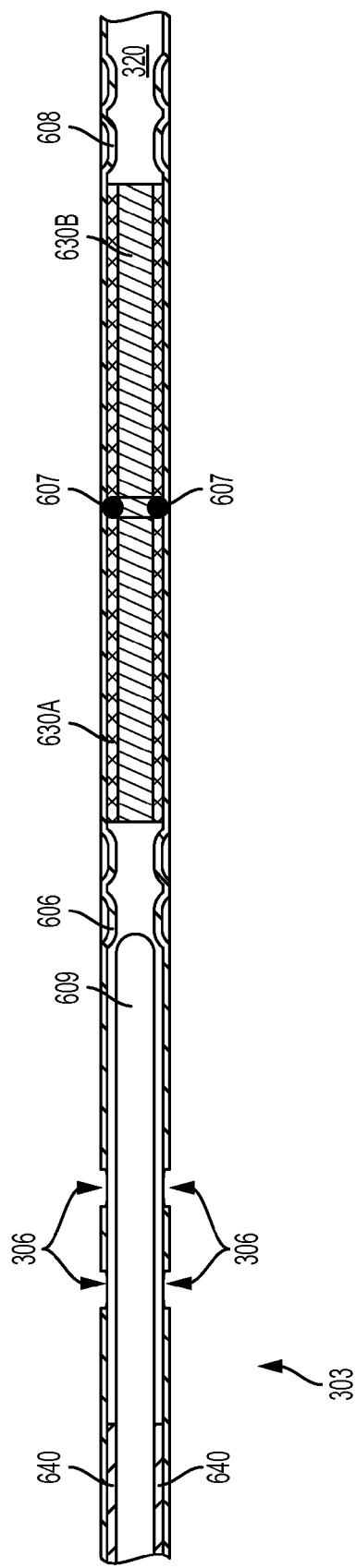

Turning to FIGS. 28, 29A and 29B, another exemplary embodiment of a fluid regulator (valve) system is shown that includes an internal piston 609 that may be directed to engage and disengage in a fluid-tight manner an internal sealing member 607 within the proximal end 303 of the guide wire shaft, for example, when piston 609 is moved axially relative to the guide wire shaft. For example, as shown in FIGS. 28 and 29A, the piston 609 may be advanced distally until the piston 609 engages the sealing member 607 in a distal position by passing through the sealing member 607 and effectively blocking the inner diameter of the sealing member, preventing flow out of the catheter and through the sealing member 607. Thus, in the distal position, the lumen 320 of the guide wire shaft may be substantially sealed or closed, for example, after delivering sufficient fluid into the lumen 320 to inflate the balloon 302, providing the valve in a closed position. Conversely, as shown in FIG. 29B, the piston 609 may be retracted proximally until the piston 609 reaches a position proximal to an outlet or side port 306 in a side wall of the proximal end 303 of the tubular member. The internal lumen 320 may communicate with the external environment adjacent the proximal end 303 through the outlet 306 when the piston 609 is retracted to the proximal position such that fluid may be delivered into or evacuated from the lumen 320, for example, to inflate or deflate the balloon 302 (not shown), where the valve is in an open position.

Figure 30:
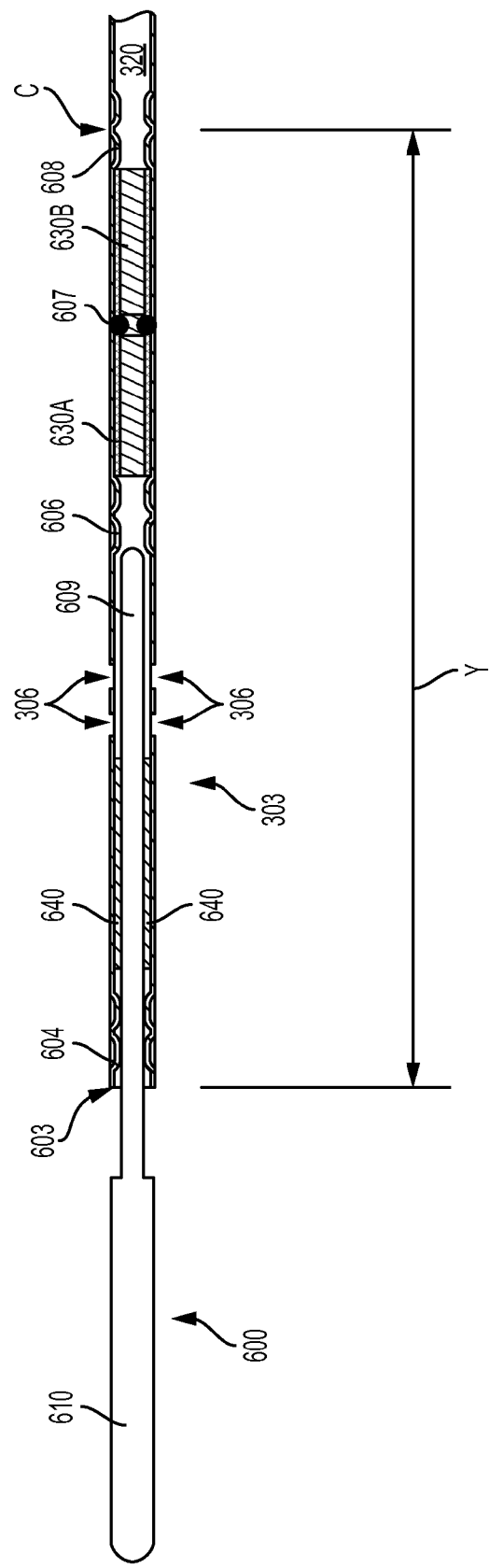
FIG. 30 is a cross-sectional side view of a piston assembly inserted at the proximal end of a guide wire device, such as the guide wire device shown in FIG. 28.

In one aspect, the sealing member 607 can comprise an O-ring that is held stationary in the lumen of the guide wire. The O-ring can be constrained between a pair of small collars or sleeves inside of the lumen 320, or in another aspect, the O-ring can be constrained by providing an indentation or crimp in the guide wire on one or both sides of the O-ring to hold it in place. In yet another aspect, the collar can comprise a pair of hypotubes 630A and 630B, or stainless steel tubes, as shown in FIG. 30. The collars or hypotubes can restrain movement of the O-ring inside of the lumen of the guide wire. In another embodiment, the O-ring can be constrained in a groove machined in the internal lumen 320. In yet another embodiment, the O-ring can be constrained by crimps or swaged features both proximally and distally of the O-ring formed in the body of the guide wire shaft 303. As mentioned above, the sealing member 607 is opened and closed by sliding the piston 609 in and out of the inner diameter of the sealing member 607, such as an O-ring. The O-ring can be kept static within the inner lumen 320 of the guide wire while the piston moves in and out of the inner diameter of the O-ring to close and open the valve, respectively. The inner diameter of the O-ring sealing member 607 should be less than the outer diameter of the guide wire shaft at that position in the guide wire, i.e., at the proximal end 303. Thus, the inner diameter of the sealing member 607 should be smaller than the outer diameter of the guide wire, which in some embodiments can be about 0.035 inches. For example, the inner diameter of the sealing member 607 can have a range from about 0.004 inches to about 0.040 inches, or in another embodiment, can have a range from about 0.004 inches to about 0.035 inches, or in yet another instance, the inner diameter of the sealing member 607 can be about 0.010 inches. The O-ring used for the valve can comprise any material that is known in the art for use with a guide wire or catheter and, in particular, can comprise EPDM (ethylene propylene diene monomer) or, in another aspect, can comprise silicone, rubber, Viton, nitrile, polyurethane, PVC, or thermoplastic elastomers, such as styrene-ethylene/butylene-styrene (SEBS), styrene-butadiene-styrene (SBS), styrene-ethylene/propylene-styrene (SEPS), thermoplastic polyolefins (TPO), among others.

The O-ring sealing member can be loaded into the lumen 320 of the guide wire utilizing a loading process that can include an O-ring loading tool. The first hypotube, or the distally-positioned hypotube 630B, can be placed on the tool, which looks like a wire that can fit inside of the guide wire lumen, followed next by the O-ring, and another hypotube, or the proximally-positioned hypotube 630A. The hypotubes 630A and 630B and the O-ring 607 can then be inserted into the lumen 320 of the guide wire by advancing the loading tool into the lumen 320. The loading tool can be advanced distally into the lumen 320 until it abuts a distal crimp in the lumen 320. A distal crimp 608 formed in the guide wire can act as a positive stop against the distal hypotube 630B.

The adjacent hypotubes 630A and 630B can have a slightly larger inner diameter than the O-ring 607 in order to hold the O-ring 607 in place, thus, essentially having an inner diameter sized to maintain the O-ring within the lumen 320 of the guide wire. In one aspect, the hypotubes 630A and 630B can have an inner diameter in the range of about 0.005 inches to about 0.035 inches and, in another aspect, can have a range from about 0.005 inches to about 0.034 inches, and in yet another aspect can have an inner diameter of approximately 0.017 inches. The outer diameter of the hypotubes 630A and 630B should be slightly less than the inner diameter of the guide wire shaft 320 at the position of the hypotubes 630A and 630B and can be in the range of about 0.006 inches to about 0.035 inches or, in another aspect, can have an outer diameter of about 0.025 inches. The hypotubes 630A and 630B can have a length between about 0.004 inches and about 1 inch and, in one aspect, a length of about 0.100 inches. It is preferred that both hypotubes have the same length, but is not necessary. The hypotubes can be any material that is appropriate for its use adjacent the O-ring and, in one aspect, can be a stainless steel tube. It is preferred that the hypotubes 630A and 630B are made out of a rigid or semi-rigid material in order to properly restrain movement of the O-ring and, in one aspect, can be any metal, ceramic or plastic material. In one embodiment, the hypotubes can be of polyimide, polyether ether ketone, polyether block amide, or other polymers that have a high durometer and rigid stiffness.

The hypotubes 630A and 630B can be kept in place by any method known in the art, such as by swaging, providing an adhesive to adhere the hypotubes in place, laser welding, providing a crimp, or any other appropriate process. In one aspect, the hypotubes 630A and 630B can be held in place by providing indentations or crimps in the guide wire. A middle crimp, or a second indentation 606, and a distal crimp 608, or a first indentation, can be provided on either end of the hypotubes 630A and 630B, as shown in FIG. 30. The second crimp 606 can be placed proximal to the proximally-positioned hypotube 630A and helps to hold the hypotubes in place, while the distal crimp 608 can be placed distal to the distally-positioned hypotube 630B and can also hold the hypotubes in place but it can also be used to aid in positioning the O-ring 607 between the two hypotubes. A crimp can be used to either restrict the inner diameter of the proximal end of the shaft 320 or to hold something in place, like the hypotubes, or both. The crimping of the wire can reduce the diameter of the wire. In one aspect, the inner diameter of the lumen 320 containing the crimp can range from about 0.006 inches to about 0.035 inches and, in another aspect can range from about 0.006 inches to about 0.034 inches, and in still another aspect can range from about 0.0225 inches to about 0.0275 inches. In yet another aspect, each end of the hypotube can have a different diameter crimp. In one preferred embodiment, the middle crimp 606 proximal to hypotube 630A can have a diameter of about 0.0215 inches while the distal crimp 608, distal to hypotube 630B, can have a diameter of about 0.0165 inches. However, the middle and distal crimps 606 and 608 can have different values than those indicated or can have values that are identical to one another. In adding the crimp marks to the wire, they can either be added manually using a crimp tool or by an automated process, using standard procedures known in the art. The crimp marks can comprise two crimp marks or indentations in the wire, with a middle section therebetween which is not indented. In the case of the distal crimp 608, it is preferred to have the center section C of the distal crimp 608 at a set distance from the proximal end 603 of the wire, as shown in FIG. 30. This ensures that the placement of the O-ring sealing member 607 will be positioned properly. In one aspect, the center C of the distal crimp 608 can be positioned at about 0.95 inches to about 0.97 inches from the proximal end 603 of the wire, as shown by distance Y in FIG. 30. Thus, if the distal crimp 608 is placed too far distal along the wire, then the O-ring 607 may not be positioned properly within the lumen of the guidewire.

The proximal end 303 of the guide wire can be provided with a valve handle assembly, or piston assembly 600, which can be used to slide the piston 609 back and forth axially in and out of the lumen of the guide wire and in and out of the inner diameter of the sealing member 607. The piston assembly 600, can include a handle 610 with an integrated piston portion or piston 609 of smaller diameter. The distal end of the piston 609 can be provided with a rounded tip or edge for easier insertion through the inner diameter of the O-ring when closing the valve. When the piston assembly 600 is moved in the proximal position, as shown in FIG. 29B, the one or more side ports 306 in the body of the guide wire are exposed such that they are no longer covered up or blocked by the piston 609; this is the valve open position. When the piston assembly 600 is in its closed position, as shown in FIG. 29A, the sealing member 607 is engaged by the piston to prevent fluid from escaping from the lumen 320 to the one or more side ports 306 and the valve is closed by the inner piston 609. In one aspect, there is at least one side port 306 and, in another aspect, there can be any number of side ports as are necessary for fluid flow. In yet another aspect, there can be up to 8 side ports positioned in the proximal end of the guide wire. The one or more side ports 306 can be provided in the body of the guide wire at a proximal end and if there are more than one, the ports can be equidistantly spaced from one another or they can be placed in any position that is most appropriate for fluid flow through and into the inner lumen 320 of the guide wire and into the open valve. In one aspect, the side ports can be laser cut holes into the guide wire such that the laser cut holes provide low restriction to fluid flow therethrough for inflation and deflation of the balloon, and it can be further electropolished such that the holes are burn-free allowing the O-ring to be loaded into the lumen of the guide wire without getting cut or damaged. The diameter of these side port holes can be any diameter that is appropriate for proper fluid flow therethrough and can range from about 0.0005 inches to about 0.03 inches, and in another aspect, can be from about 0.0005 inches to about 0.0265 inches, and in still another aspect, can be about 0.007 inches in diameter.

In order for the piston assembly 600 to be movable within the lumen 320 of the guide wire, it can be provided with a frictional element, such as a spring element 640, that collapses when placed into the lumen 320 of the guide wire and acts to push against the inner diameter of the guide wire to provide a certain level of friction. The amount of friction can be adjusted by the bend angle on the frictional element, by the thickness of the spring members, and/or by the modulus of the material chosen for the frictional element. The spring element 640 can be made by splitting the wire of the piston, such as creating a "w" shaped wire, or from a separate piece of material, such as a split tube, for example, that is welded onto the wire of the piston 609, such that it acts as a spring to create friction between the spring element and the guide wire lumen to prevent the valve from being inadvertently opened or closed. A "w" shaped wire can be formed in the wire of the piston, such that the straight piston is bent at a section of the wire to make several bends resembling the peaks and valleys of the letter w. Fewer or additional bends may be added to decrease or increase the amount of friction. Alternatively, other materials or elements can be used as a friction element such as elastomeric materials, another O-ring, or multiple O-rings, for example.

Figure 31A:
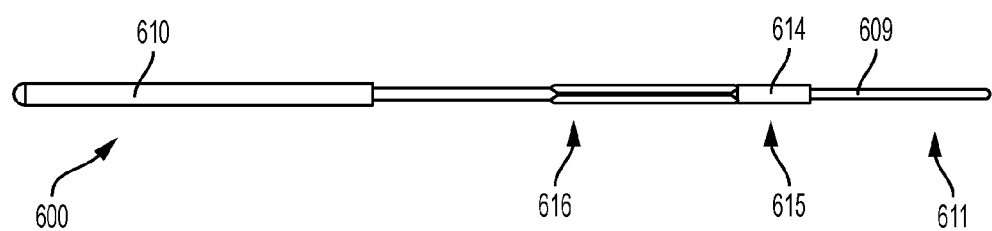
FIG. 31A is a side view of a piston assembly with a split tube attached to a piston of the piston assembly, prior to forming the split tube into a frictional element.

In one embodiment, the frictional element 640 can be formed by adding a separate element, or split tube, welded onto the piston 609, which can then be bent after it is attached to the piston 609 to provide the frictional element 640. Alternatively, a separate tube can first be bent into shape and then attached to the piston. The frictional element may also be bonded or crimped onto the piston. Where a split tube 614 is welded onto the piston 609 of the piston assembly 600 prior to shaping it in the bent configuration, it can be welded at a location on the piston assembly 600 that is on the piston near the distal end 611 of the piston 609, as seen in FIG. 31A. In one aspect, the split tube 614 can be welded by laser beam welding. The split tube 614 can be welded at a distal end 615 of the split tube 614 positioned a certain distance from the distal end 611 of the piston 609 such that the split end 616 of the tube is positioned a certain distance from the handle 610. The split end 616, in one embodiment, can be formed by splitting a tube in half such that two leaves or wings 612 are created. In another aspect, the split tube 614 can be attached at a position that is about 0.250 inches proximal to the distal end 611 of the piston 609. In yet another aspect, the split tube 614 can be welded at a position that is between about 0.010 inches to about 6 inches from the distal end 611. The diameter of the split tube 614 can be slightly larger than that of the piston and, in one aspect, the diameter of the split tube can be about 0.017 inches. The split tube 614 outer diameter, not including the formed frictional portion, can be slightly smaller than the inner diameter or lumen of the guide wire to allow it to slide freely in and out of the lumen without interference. The wings 612 of the frictional element, once formed or shaped, are larger than the inner diameter of the guide wire so that it can cause friction upon axially shifting the piston in the lumen.

In one embodiment, the diameter of the piston 609 can be about 0.015 inches and the diameter of the handle 610 can be about 0.0320 inches. In another embodiment, the diameter of the piston can range between about 0.005 inches to about 0.035 inches, or in another aspect from 0.005 inches to about 0.034 inches. The diameter of the handle 610 can range between about 0.005 inches to about 0.04 inches, and in another aspect can range from about 0.005 inches to about 0.038 inches. The piston 609 can be provided integrated with the handle 610 such that there is a reduction in diameter from the handle to the piston and, in one aspect, this reduction can be about 50%. The piston can also be electropolished to aid in minimizing wear upon the O-ring each time the piston is inserted into the inner diameter of the O-ring. The distal end of the piston, i.e., the end being inserted into the inner diameter of the O-ring, can be provided as a fully rounded end. The piston can also be electropolished, ground smooth, lapped or chemically polished to provide a smooth surface, e.g., a burr-free surface, to slide smoothly without cutting the O-ring each time it is opened and closed. The length of the piston assembly 600, can have a length that is long enough to be inserted into the lumen 320 of the guide wire and advance distally through the lumen 320 and through the inner diameter of the O-ring an appropriate distance to provide a closed state of the valve. In one aspect, the length of the piston assembly 600 can be about 1.355 inches, where the handle 610 can be about 0.50 inches in length and the piston 609 can be about 0.855 inches in length. In a preferred embodiment, the length of the piston 609 can be greater than the length of the handle 610, where these two lengths can range from about 0.010 inches to about 6 inches. Alternatively, the handle 610 can be longer than the piston 609. In another preferred embodiment, the diameter of the piston can be less than the diameter of the handle. Alternatively, the handle can have a smaller diameter than the piston. In one aspect, the piston 609 can comprise at least 50% of the length of the piston assembly and, in a preferred aspect, at least 60% of the piston assembly, and still more preferred, at least 63% of the piston assembly. In one embodiment, the handle 610 can comprise 37% of the piston assembly 600 while the piston 609 can comprise about 63% of the piston assembly. The handle and piston can be formed as one unit and can be formed out of stainless steel, however, other materials of construction appropriate for use with the guide wire can be provided. It is preferred that the diameter of the handle provides a similar profile as the guide wire shaft or lumen, e.g., has a similar diameter, or still more preferred that the diameter of the handle is slightly smaller than the diameter of the lumen so as not to catch on catheters or other devices sliding over it, in order to prevent the valve from being inadvertently opened or closed. It is preferred that the diameter of the piston is compatible with the O-ring inner diameter, and is still more preferred that the diameter of the piston is slightly larger than the inner diameter of the O-ring, for example, by at least 0.0005 inches, in order to form a seal, yet not too large where it could tear the O-ring. In one aspect, the O-ring inner diameter is 0.010 inches and the piston outer diameter is about 0.015 inches.

The length of the split tube 614 can be shorter than the overall length of the piston 609 extending distal from the handle 610. In one aspect, the length of the split tube can be about 0.35 inches, with the leaves or wings 612 having a length of about 0.25 inches. In another aspect, the length of the split tube can vary between about 0.030 inches to about 6 inches and the length of the wings can vary between about 0.020 inches to about 6 inches, or in another aspect the length of the wings can vary between about 0.020 inches to about 5.950 inches. Any length of the wings is appropriate that can be made into the frictional element. In one aspect, the length of the wings can comprise at least about 10% of the overall length of the split tube, in another aspect, at least about 60% of the overall length of the split tube, and in yet another aspect, can comprise at least about 70% of the overall length of the split tube, and in still another aspect, at least about 71% of the overall length of the split tube.

Figure 31B:
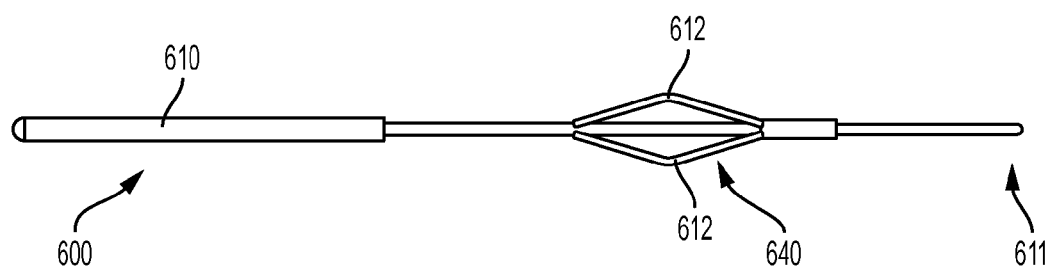
FIG. 31B is a side view of the piston assembly of FIG. 31A, where the split tube has been formed into the frictional element.

One method of forming the frictional element includes attaching the split tube, which can comprise two leaves or wings, and placing the split tube and piston on a bending tool between two pins. The leaves or wings of the split tube can then be spread such that the wings can catch on the two pins and can be spread apart and away from the piston to stick outward in a V-shape. The piston is then shifted in a manner that further separates the wings of the split tube and brings them in contact with a second set of pins. The second set of pins can bring the outward ends of the wings together while at the same time bending the mid-section of the wings around the first set of pins to result in a diamond-shape orientation of the wings. This diamond-shape orientation can result in the frictional element of the piston, as shown in FIG. 31B. Alternatively, other methods for forming bends in a wire or tube may be employed.

Another method of forming a frictional element is to machine, stamp, etch or laser cut a flat or curved piece of metal, and form it into a spring. This formed sheet metal component can then be attached to the piston and pushed onto the inner diameter of the guide wire shaft to provide friction. In one embodiment, a frictional element can be formed from a flat sheet of sheet metal. The sheet metal can have a hole cut in the middle of it and bend along bend lines, where the hole remains as a centerpoint. When bent, the sheet metal can look like a backwards 'C.' This bent sheet metal can then be attached to the piston, by inserting the piston through the hole of the bent sheet metal. In other embodiments, a plurality of sheet metal parts can be bent and formed without cutting a hole in the middle and can be attached to the piston.

One benefit of utilizing the frictional element-split tube design is that the bends in the split tube are located symmetrical to one another such that upon inserting the piston into the lumen 320 of the guide wire the frictional element provides for a centering of the piston in the lumen 320. If a w-wire is used, it may sometimes provide an off-center positioning of the piston due to its w-orientation of the bends, i.e., non-symmetrical bends on either side of the wire.

The spring element 640 in a relaxed, uncollapsed state can be seen in FIG. 31B, prior to it being introduced into the lumen 320. When the piston and piston assembly 600 are placed inside of the lumen 320 of the guide wire, the spring element 640 can collapse inside of the lumen 320, as seen in FIG. 30.

At the proximal end 602 of the guide wire, can be provided another crimp or third indentation 604. This crimp, or proximal crimp 604, can provide a positive stop on opening the sealing member 307, i.e., proximally withdrawing the piston 609 from the lumen 320, which interacts with the frictional element 640 such that it catches on the proximal end of the frictional element 640 and prevents the frictional element 640 and handle from being pulled out of the lumen 320 upon withdrawing the piston 609 in a proximal direction. This proximal crimp 604 can provide a narrowed or smaller diameter than that of the guide wire and, in one aspect, can provide a reduced diameter of about 0.006 inches to about 0.035 inches, or in another aspect from about 0.006 inches to about 0.034 inches. In yet another aspect, the reduced diameter can be about 0.0275 inches or less. In still another aspect, the proximal crimp 604 can have a diameter of about 0.0225 inches. The piston 609 becomes visible upon opening valve because the diameter of the piston 609 is less than the diameter of the piston assembly 600 such that a difference in thickness between the two becomes visible. Upon closing the valve, i.e., moving the piston 609 in a distal direction further into the lumen 320 and into the inner diameter of the O-ring, the handle 610 and, in particular, the larger diameter of the handle in comparison to the piston, can provide a positive stop against the guide wire shaft upon closing the valve due to a stepped portion on the handle (not shown in Figures). When the diameter of the handle is similar to the diameter of the guide wire shaft, this can allow for a smooth transition between the two in the closed position to allow devices to pass over the proximal end of the guide wire. As previously mentioned, the difference in the diameter of the handle and the piston (e.g., for instance, where the handle diameter is greater than the piston diameter) can provide a visual feedback that the valve is in an open state. When the piston shaft is no longer visible, then the valve is in a closed state. In another aspect, the piston can be marked, plated, covered in colored heat shrink, or painted a different color to improve contrast to show that it is in an open state.

Turning to FIGS. 32A and 32B, another embodiment of a fluid regulator (valve) system is shown that includes the sealing member (e.g., O-ring) 607 attached to the piston 609, and reciprocating distally past the fill port(s) 306 to seal it in the closed position, i.e., covering/blocking the fill ports 306 with the piston 609 to prevent any fluid from escaping or entering, and shifted proximally of the fill port(s) 306 to allow fluid flow. In this embodiment, the O-ring can move with the piston and can also act as a friction element.

Some benefits of having the piston assembly at the proximal-most end of the guide wire is that the there is a visual indication whether the valve is in a closed or open position based upon the position of the piston assembly. For instance, when the valve is in an opened position, the piston assembly is pulled proximally away from the guide wire such that it exposes the piston and exposes one or more side ports 306. When the piston assembly is in this extended position, as shown in FIG. 29B or 32B, a certain distance of the piston 609 is exposed. In one aspect, at least about 4 millimeters of the piston tube 609 are visible. When in the closed position, the piston is not visible outside of the lumen such that the user understands that the valve is closed. Another benefit of a valve system with a frictional element, is that the friction element of the piston assembly requires a certain force be exerted upon the proximal end to slide the handle proximal to the valve and thus, accidental opening or closing of the valve is prevented. The piston assembly allows for the user to easily open and close the valve manually and to do so multiple times, as necessary.

In addition, the sealing member 607 can have a small profile such that the outer diameter of the sealing member is smaller than the guide wire outer diameter. The small diameter and the way in which the O-ring is constrained on either end by a small hypotube sleeve allows for the profile of the O-ring as the sealing element to remain small. The integrated piston and design of the friction element allows for a small profile where the piston has an end integrated into a handle that substantially matches the outer diameter of the guide wire. Moreover, the piston 607 provided in the guide wire can be robust enough such that it allows other devices, such as introducers, to be passed over the valve. As the piston is integrated with the handle as a single unit, i.e., as the piston assembly, it can all be ground from stainless steel or other high strength metal or alloy to improve its robustness. The proximal end of the handle can be provided with a smooth rounded tip and the distal end of the handle can further provide a smooth transition to the main body of the guide wire when in the closed position, hence minimizing any sharp edges when passing other devices over the proximal end of the handle and guide wire assembly. Furthermore, the integrated frictional element can help to center the piston into the O-ring and to center the handle to the guide wire body to help maintain them coaxial to one another.

Other benefits are that when the valve is in the open position, there are minimal flow restrictions to any fluid that is introduced to allow for adequate inflation and deflation of the balloon. Multiple ports in the guide wire can help to reduce flow restrictions into the lumen of the guide wire. Additionally, there is provided a visual feedback to the user to determine if the valve is in an opened state or a closed state. This can be provided by a stepped transition from the piston to the handle, which can be visible when the valve is in the open position, providing the necessary visual feedback when the valve is in the open position. Another benefit is in having the frictional element along the piston can prevent accidental opening and/or closing of the valve provided by a spring force to increase friction to keep the valve from accidentally opening or closing.

Further benefits include the ability to open and close the valve manually by a user, even a user that is wearing gloves or a covering on the hands. Special tools are not required to open and close the valve. The amount of friction provided by the frictional element can be adjusted to allow for ease of opening and closing, yet to prevent an accidental opening or closing. Additionally, providing a stationary O-ring valve allows for multiple actuation of the valve with minimal wear upon the valve. Providing the valve in an open position where the piston is not engaged with the O-ring can minimize the effects of compression on the O-ring during storage. Alternatively, a non-stationary O-ring valve can also be provided upon the end of a piston, which can also provide for multiple actuation of the valve with minimal wear upon the valve.

The method of inflating the balloon provided herein also applies to the alternative valve embodiment provided above and in FIGS. 28-31B. In order to inflate the balloon, the sealing member 607 can first be opened by sliding or withdrawing the piston assembly 600 in a proximal direction to expose the piston 609 as well as exposing the holes 306 and opening the sealing member 607, as shown in FIG. 29B. The balloon can then be inflated as already provided herein and in order to maintain the inflation of the balloon, the valve should be closed, as shown in FIG. 29A. To close the valve, the piston assembly 600 can be advanced in a distal direction until the piston 609 is no longer visible. This ensures that the distal end of the piston 609 has passed through the inner diameter of the sealing member, e.g., O-ring, closing off the valve, as well as blocking off the holes 306 and preventing any fluid from exiting therethrough. The piston assembly 600 can remain in this position until it is necessary to deflate the balloon, then the piston assembly can be withdrawn once more in the proximal direction to expose the piston at the proximal end of the guide wire and to slide the piston proximally out of the O-ring inner diameter to open the valve allowing the fluid to escape through the holes and O-ring and thus deflating the balloon. The side ports or holes 306 do not need to be completely exposed in order to allow for fluid to escape therethrough. There can be enough of a gap provide between the piston and, in particular, between the piston and the frictional element that even if the piston is not withdrawn completely to expose the holes, the gap between the piston and the holes is adequate to provide for fluid to escape therethrough. Similarly, the balloon can be inflated in a like manner in the embodiments of FIGS. 32A and 32B, only the method of closing and opening the valve varies.

Elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives thereof.

What is claimed is:

1. A device for use during an intravascular procedure, the device having a valve for closing and opening fluid flow through a lumen of the device, the device comprising:
    an elongate body having a proximal end, a distal end and a lumen extending longitudinally through at least part of the elongate body, the elongate body comprising:
        a proximal portion; and
        a flexible distal portion;
    a sealing member having an inner diameter and an outer diameter positioned in the lumen of the elongate body at the proximal portion of the elongate body;
    a piston assembly for insertion into the lumen of the elongate body at the proximal end, the piston assembly having a handle with an integral piston, the piston extending through the inner diameter of the sealing member when the valve is in a closed state and the piston retracted axially from the inner diameter of the sealing member in a proximal direction when the valve is in an open state;
    a frictional element connected to an outer diameter of the piston, wherein the frictional element is larger than an inner diameter of the lumen in a relaxed state and partially collapses into a collapsed state upon placement in the lumen, wherein the frictional element pushes against the inner diameter of the elongate body to provide friction upon axial movement of the piston within the lumen; and
    an inflatable balloon attached to the elongate body and in communication with the lumen, wherein the device allows fluid to be advanced through the lumen of the elongate body and through the inner diameter of the sealing member to inflate and deflate the inflatable balloon when the valve is in the open state.

2. The device as in claim 1, wherein the frictional element comprises a pair of symmetrical wings.

3. The device as in claim 1, wherein the sealing member is constrained within the lumen by a pair of collars positioned on either side of the sealing member.

4. The device as in claim 3, wherein the pair of collars are a pair of hypotubes.

5. The device as in claim 4, wherein the pair of hypotubes have an inner diameter ranging between about 0.005 inches to about 0.035 inches.

6. The device as in claim 4, wherein the pair of hypotubes have an inner diameter that is less than an outer diameter of the sealing member.

7. The device as in claim 3, wherein each collar is held in place by an indentation placed in the elongate body adjacent each collar, the indentations narrowing the inner diameter of the lumen at the indentation.

8. The device as in claim 7, wherein a middle indentation is placed in the elongate body adjacent a proximally-positioned hypotube and a distal indentation is placed in the elongate body adjacent a distally-positioned hypotube.

9. The device as in claim 8, wherein the middle indentation is positioned proximal of the proximally-positioned hypotube and the distal indentation is positioned distal of the distally-positioned hypotube.

10. The device as in claim 1, wherein the sealing member is an O-ring.

11. The device as in claim 10, wherein the O-ring has an inner diameter ranging between about 0.004 inches and about 0.035 inches.

12. The device as in claim 1, wherein the elongate body has at least one side port that communicates with the lumen to provide for passage of a fluid.

13. The device as in claim 12, wherein the elongate body has at least 8 side ports.

14. The device as in claim 1, wherein the sealing member is configured to lock inflation fluid inside the lumen when the valve is in a closed position, to allow an inflation device to be removed, thus leaving a hubless proximal end over which one or more devices may be advanced.

15. The device as in claim 1, wherein the piston is movable between a proximal position and a distal position, and the valve is closed when the piston is in the distal position.

16. The device as in claim 1, wherein the distal portion comprises:
    a proximal section having a first flexibility; and
    a J-tip at the distal end of the elongate body having a second flexibility that is greater than the first flexibility.

17. The device as in claim 16, wherein the proximal section has a length of at least about 15 cm, and wherein the J-tip has a length of at least about 5 cm.

18. The device as in claim 1, wherein the distal portion has a length of at least about 20 cm.

19. The device as in claim 1, wherein the distal portion has a length approximately equal to an average length of an iliofemoral artery.

20. The device as in claim 1, wherein a proximal indentation is formed in the elongate body at the proximal portion to prevent the piston from being withdrawn completely from the lumen.

21. The device as in claim 1, wherein the elongate body further comprises a transition portion between the proximal portion and the distal portion, and wherein the distal portion comprises a core wire wrapped in a coil, and wherein the core wire extends through the transition portion and into the proximal portion.

22. The device as in claim 1, wherein the proximal portion comprises a tube with a spiral cut along a portion of its length nearer its distal end, wherein the spiral cut has decreasing spacing toward the distal end.

23. The device of claim 1, further comprising an expandable member secured to the elongate body and in communication with the lumen of the elongate body, and wherein the device is configured to couple with an inflation device to allow for inflation and deflation of the expandable member.

24. A vascular guide wire system, comprising:
    an elongate body comprising a proximal portion, a flexible distal portion, and a lumen extending longitudinally through at least part of the elongate body;
    an inflatable balloon attached to the elongate body and in communication with the lumen;

a valve assembly having an open position for inflating and deflating the inflatable balloon and a closed position for maintaining fluid within the lumen, the valve assembly comprising:
a sealing member on the proximal portion of the elongate body, the sealing member having an inner diameter and an outer diameter, the outer diameter sized smaller than an inner diameter of the lumen;
a piston assembly for insertion into the lumen of the elongate body, the piston assembly having a handle, an integral piston portion, the piston portion configured for insertion into the inner diameter of the sealing member to provide the closed position of the valve assembly and further having a frictional element attached to an outer diameter of the piston portion, wherein the frictional element is larger than an inner diameter of the lumen in a relaxed state and partially-collapses into a collapsed state upon placement in the lumen, wherein the frictional element pushes against the inner diameter of the elongate body to provide friction upon axial movement of the piston within the lumen;
a proximal collar and a distal collar placed on either side of the sealing member inside of the lumen to maintain the sealing member in position; and
a first indentation formed on the elongate body proximal to the proximal collar and a second indentation formed on the elongate body distal to the distal collar.

25. The guide wire system as in claim 24, wherein an inflation device is configured to couple with the elongate body and allow for inflation of the inflatable balloon when the valve assembly is in an open position.

26. The guide wire system as in claim 25, wherein the piston assembly is movable in an axial direction, and wherein the valve assembly is configured to lock inflation fluid inside the lumen when in the closed position, to allow the inflation device to be removed, thus leaving a hubless proximal end of the elongate body, over which one or more devices may be advanced.

27. The guide wire system as in claim 25, further comprising an inflation medium injection device selected from the group consisting of a syringe and a pump.

28. The guide wire system as in claim 24, wherein the distal portion of the elongate member comprises a J-tip and has a length of at least about 20 cm.

29. The guide wire system as in claim 24, wherein a proximal end of the elongate body is hubless.

30. The guide wire system as in claim 24, wherein the elongate body further comprises a transition portion between the proximal portion and the distal portion, and wherein the distal portion of the elongate member comprises a core wire wrapped in a coil, and wherein the core wire extends through the transition portion and into the proximal portion.

* * * * *